United States Patent
Lowe, III et al.

(10) Patent No.: US 9,504,670 B2
(45) Date of Patent: Nov. 29, 2016

(54) SPIRO-LACTAM NMDA RECEPTOR MODULATORS AND USES THEREOF

(71) Applicant: Aptinyx Incorporated, Evanston, IL (US)

(72) Inventors: John A. Lowe, III, Stonington, CT (US); M. Amin Khan, Evanston, IL (US)

(73) Assignee: Aptinyx, Inc., Evanston, IL (US)

( * ) Notice: Subject to any disclaimer, the term of this patent is extended or adjusted under 35 U.S.C. 154(b) by 0 days.

(21) Appl. No.: 14/932,579

(22) Filed: Nov. 4, 2015

(65) Prior Publication Data

US 2016/0289240 A1    Oct. 6, 2016

Related U.S. Application Data

(63) Continuation of application No. 14/764,395, filed as application No. PCT/US2014/013619 on Jan. 29, 2014.

(60) Provisional application No. 61/757,903, filed on Jan. 29, 2013.

(51) Int. Cl.
   *A61K 31/397*    (2006.01)
   *C07D 487/10*    (2006.01)

(52) U.S. Cl.
   CPC ........... *A61K 31/397* (2013.01); *C07D 487/10* (2013.01)

(58) Field of Classification Search
   CPC .......................... A61K 31/397; C07D 487/10
   USPC ....................................... 514/210.2; 548/409
   See application file for complete search history.

(56) References Cited

U.S. PATENT DOCUMENTS

| | | |
|---|---|---|
| 4,904,681 A | 2/1990 | Cordi et al. |
| 4,959,493 A | 9/1990 | Ohfume et al. |
| 5,061,721 A | 10/1991 | Cordi et al. |
| 5,086,072 A | 2/1992 | Trullas et al. |
| 5,166,136 A | 11/1992 | Ward et al. |
| 5,168,103 A | 12/1992 | Kinney et al. |
| 5,350,769 A | 9/1994 | Kasai et al. |
| 5,523,323 A | 6/1996 | Maccecchini |
| 5,605,911 A | 2/1997 | Olney et al. |

(Continued)

FOREIGN PATENT DOCUMENTS

| | | |
|---|---|---|
| CN | 101066945 A | 11/2007 |
| CN | 101125817 A | 2/2008 |

(Continued)

OTHER PUBLICATIONS

Abbott AV et al., 'The Formalin Test: Scoring Properties of the First and Second Phases of the Pain Response in Rats,' Pain, Jan. 1995 (Jan. 1995), 60(1):91-102.

(Continued)

*Primary Examiner* — Kamal Saeed
*Assistant Examiner* — Janet L Coppins
(74) *Attorney, Agent, or Firm* — Goodwin Procter LLP

(57) ABSTRACT

Disclosed are compounds having enhanced potency in the modulation of NMDA receptor activity. Such compounds are contemplated for use in the treatment of conditions such as depression and related disorders. Orally available formulations and other pharmaceutically acceptable delivery forms of the compounds, including intravenous formulations, are also disclosed.

8 Claims, 2 Drawing Sheets

(56) References Cited

U.S. PATENT DOCUMENTS

| | | |
|---|---|---|
| 5,648,259 A | 7/1997 | Mallet et al. |
| 5,741,778 A | 4/1998 | Martin et al. |
| 5,763,393 A | 6/1998 | Moskal et al. |
| 5,804,550 A | 9/1998 | Bourguignon |
| 5,902,815 A | 5/1999 | Olney et al. |
| 5,952,389 A | 9/1999 | Fogel |
| 5,959,075 A | 9/1999 | Lok et al. |
| 6,007,841 A | 12/1999 | Caruso |
| 6,025,471 A | 2/2000 | Deghenghi |
| 6,107,271 A | 8/2000 | Moskal et al. |
| 6,147,230 A | 11/2000 | Shimamoto et al. |
| 6,197,820 B1 | 3/2001 | Sontheimer et al. |
| 6,521,414 B2 | 2/2003 | Melcher et al. |
| 6,541,453 B2 | 4/2003 | Oldham et al. |
| 6,635,270 B2 | 10/2003 | Hong et al. |
| 6,667,317 B2 | 12/2003 | Chenard et al. |
| 6,821,985 B2 | 11/2004 | Chenard et al. |
| 6,828,318 B2 | 12/2004 | Snape et al. |
| 7,273,889 B2 | 9/2007 | Mermelstein et al. |
| 7,884,080 B2 | 2/2011 | Aslanian et al. |
| 8,492,340 B2 | 7/2013 | Moskal |
| 2002/0103335 A1 | 8/2002 | Oldham et al. |
| 2003/0022253 A1 | 1/2003 | Moskal |
| 2003/0064921 A1 | 4/2003 | Millhauser et al. |
| 2003/0175734 A1 | 9/2003 | Kroes et al. |
| 2005/0037433 A1 | 2/2005 | Nakanishi et al. |
| 2005/0118286 A1 | 6/2005 | Suffin et al. |
| 2006/0063707 A1 | 3/2006 | Baudry et al. |
| 2006/0241046 A1 | 10/2006 | Olivera et al. |
| 2007/0087404 A1 | 4/2007 | Stahl et al. |
| 2007/0208001 A1 | 9/2007 | Zhuo et al. |
| 2009/0221544 A1 | 9/2009 | Stein et al. |
| 2010/0102616 A1 | 4/2010 | Yamasaki et al. |
| 2011/0306586 A1 | 12/2011 | Khan et al. |
| 2012/0295852 A1 | 11/2012 | Moskal |
| 2013/0005662 A1 | 1/2013 | Moskal |
| 2013/0035292 A1 | 2/2013 | Moskal et al. |
| 2013/0053325 A1 | 2/2013 | Moskal et al. |
| 2013/0310323 A1 | 11/2013 | Moskal |
| 2013/0316954 A1 | 11/2013 | Moskal |
| 2014/0107037 A1 | 4/2014 | Moskal |
| 2015/0051262 A1 | 2/2015 | Khan et al. |
| 2015/0105364 A1 | 4/2015 | Khan et al. |
| 2015/0336969 A1 | 11/2015 | Khan et al. |
| 2015/0368252 A1 | 12/2015 | Lowe, III et al. |
| 2015/0368253 A1 | 12/2015 | Lowe, III et al. |
| 2015/0368254 A1 | 12/2015 | Lowe, III et al. |
| 2015/0376195 A1 | 12/2015 | Lowe, III et al. |

FOREIGN PATENT DOCUMENTS

| | | |
|---|---|---|
| CN | 103974712 A | 8/2014 |
| CN | 104321071 A | 1/2015 |
| EP | 2542254 A1 | 1/2013 |
| EP | 2771021 A0 | 5/2013 |
| JP | 2013519683 A | 5/2013 |
| JP | 2014520072 A | 8/2014 |
| RU | 2039035 C1 | 7/1995 |
| WO | WO-9632105 A1 | 10/1996 |
| WO | WO-97/43306 A1 | 11/1997 |
| WO | WO-99/24584 A1 | 5/1999 |
| WO | WO-99/51985 A1 | 10/1999 |
| WO | WO-00/28090 A2 | 5/2000 |
| WO | WO-01/36685 A2 | 5/2001 |
| WO | WO-01/96606 A2 | 12/2001 |
| WO | WO-01/98367 A2 | 12/2001 |
| WO | WO-02/47535 A2 | 6/2002 |
| WO | WO-02/072609 A2 | 9/2002 |
| WO | WO-03/010540 A1 | 2/2003 |
| WO | WO-2005/020973 A2 | 3/2005 |
| WO | WO-2007103719 A2 | 9/2007 |
| WO | WO-2009/039390 A2 | 3/2009 |
| WO | WO-2009/105718 A1 | 8/2009 |
| WO | WO-2010/015545 A1 | 2/2010 |
| WO | WO-2010/033757 A1 | 3/2010 |
| WO | WO 2010033757 A1 * | 3/2010 ........... C07D 471/20 |
| WO | WO-2010/065709 A2 | 6/2010 |
| WO | WO-2010/102616 A1 | 9/2010 |
| WO | WO-2011/003064 A2 | 1/2011 |
| WO | WO-2011/044089 A2 | 4/2011 |
| WO | WO-2011/100585 A1 | 8/2011 |
| WO | WO-2012/149389 A2 | 11/2012 |
| WO | WO-2013/001448 A1 | 1/2013 |
| WO | WO-2013014448 A1 | 1/2013 |
| WO | WO-2013/063120 A2 | 5/2013 |
| WO | WO-2014/011590 A2 | 1/2014 |
| WO | WO-2014/120784 A1 | 8/2014 |
| WO | WO-2014/120786 A1 | 8/2014 |
| WO | WO-2014/120789 A1 | 8/2014 |
| WO | WO-2014/120800 A1 | 8/2014 |

OTHER PUBLICATIONS

Abramets, II, 'Neurophysiological and Neurochemical Aspects of the Effects of Antidepressants and Mood Stabilizers,' Neurophysiol, Jan. 2008 (Jan. 2008), 40(1):64-78.

Alonso E et al., 'Spiro-Beta-Lactams as Beta-Turn Mimetics. Design, Synthesis, and NMR Conformational Analysis,' J Org Chem, Sep. 21, 2001 (Sep. 21, 2001), 66(19):6333-8.

Anonymous, Database Accession No. 1031928-30-9, Database Registry [Online] Chemical Abstracts Service, Columbus, Ohio, US; Jul. 1, 2008 (Jul. 1, 2008), XP002668992.

Anonymous, Database Accession No. 1053605-89-2, Database Registry [Online] Chemical Abstracts Service, Columbus, Ohio, US; Sep. 28, 2008 (Sep. 28, 2008), XP002668993.

Anonymous, NCBI Submission NM_000149, 'Homo Sapiens Fucosyltransferase 3 (galactoside 3(4)-L-fucosyltransferase, Lewis Blood Group)(FUT3), Transcript Variant 1, mRNA,' 1990 (1990), Retrieved from the internet; <<URL:http://www.ncbi.nlm.nih.gov/nuccore/148277008>>, pp. 1-5.

Anonymous, NCBI Submission NM_001276, 'Homo Sapiens Chitinase 3-like 1 (cartilage glycoprotein-39)(CHI3L1), mRNA,'1989 (1989), Retrieved from the internet; <URL:http://www.ncbi.nlm.nih.gov/nuccore/144226250>, pp. 1-5.

Anonymous, NCBI Submission NM_030979.1, 'Homo Sapiens poly(A) Binding Protein, Cytoplasmic 3 (PABPC3), mRNA,' 2003 (2003), Retrieved from the internet; <URL:http://www.ncbi.nlm.nih.gov/nuccore/13569957>, pp. 1.

Anonymous, NCBI Submission NM_173216, 'Homo Sapiens ST6 beta-galactosamide alpha-2,6-sialyltransferase 1 (ST6GAL1), transcript variant 1, mRNA,' 1989 (1989), Retrieved from the internet; <URL:http://www.ncbi.nlm.nih.gov/nuccore/27765090>, pp. 1-5.

Bennett GJ and Xie Y-K, 'A Peripheral Mononeuropathy in Rat That Produces Disorders of Pain Sensation Like Those Seen in Man,' Pain, Apr. 1988 (Apr. 1988), 33(1):87-107.

Bittermann H and Gmeiner P, 'Chirospecific Synthesis of Spirocyclic beta-Lactams and Their Characterization as Potent Type II beta-Turn Inducing Peptide Mimetics,' J Org Chem, Jan. 6, 2006 (Jan. 6, 2006), 71(1):97-102.

Bittermann H et al., 'A Highly Practical RCM Approach Towards a Molecular Building Kit of Spirocyclic Reverse Turn Mimics,' Chem Eur J, Aug. 16, 2006 (Aug. 16, 2006), 12(24):6315-22.

Burch RM et al., 'GLYX-13, An NMDA Receptor Glycine Site Functional Partial Agonist, Does Not Elicit Psychotomimetic Side Effects in Normal Human Volunteers at Doses Expected to be Therapeutic in Treatment-Resistant Major Depressive Disorder,' NCDEU, Jun. 16, 2010 (Jun. 16, 2010), Naurex, Inc., Evanston, IL (Publ), pp. 1 (Poster #unknown).

Burgdorf JS et al., 'Neurobiology of 50-kHz Ultrasonic Vocalizations in Rats: Electrode, Lesion, and Pharmacology Studies,' Behav Brain Res, Mar. 19, 2007 (Mar. 19, 2007) (ePub), 182(2):274-83.

Burgdorf JS et al., 'The Antidepressant and Anxiolytic Properties of GLYX-13: A Novel NMDA Receptor Glycine Site Functional Partial Agonist,' ACNP 2010 Meeting, Dec. 6, 2010 (Dec. 6, 2010), pp. 1 (Poster#198).

Burgdorf JS et al., 'The Effects of Selective Breeding for Differential Rates of 50-kHz Ultrasonic Vocalizations on Emotional Behavior in Rats,' Dev Psychobiol, Jan. 2009 (Jan. 2009), 51(1):34-46.

(56) References Cited

OTHER PUBLICATIONS

Burgdorf JS et al., 'The N-Methyl-D-Aspartate Receptor Modulator GLYX-13 Enhances Learning and Memory, in Young Adult and Learning Impaired Aging Rats,' Neurobiol Aging, May 14, 2009 (May 14, 2009) (ePub), 32(4):698-706.
Burgdorf JS et al., 'Uncovering the Molecular Basis of Positive Affect Using Rough-and-Tumble Play in Rats: A Role for the NMDA Receptor and Implications for Depression,' Neuroscience, Jul. 14, 2010, (Jul. 14, 2010) (ePub), 168(3):769-77.
Burgdorf JS et al., 'Uncovering the Molecular Basis of Positive Affect Using Rough-and-Tumble Play in Rats: A Role for the NMDA Receptor and Implications for Depression,' Neuroscience 38th Annual Meeting, Washington DC, Nov. 17, 2008 (Nov. 17, 2008), pp. 1-2 (Poster #393.1/UU11) [Electronically available Sep. 2008].
Careri M et al., 'Pentcopper(II) 12-Metallacrown-4 Complexes with alpha- and beta-Aminohydroxamic Acids in Aqueous Solution: A Reinvestigation,' J Inorg Chem, Jan. 15, 2003 (Jan. 15, 2003), 93(3-4):174-80.
Coates C et al., 'Product Class 9: Beta-Lactams,' *Science of Synthesis*, Georg Thieme Verlag KG, Stuttgart, DE (Pub), 2000 (2000), 21:609-46.
Cremonesi G et al., 'Enantiomerically Pure Polyheterocyclic Spiro-beta-Lactams from trans-4-Hydroxy-L-proline,' J Org Chem, Mar. 19, 2010 (Mar. 19, 2010), 75(6):2010-7.
Dalla Croce P and La Rosa C, 'Stereoselective Synthesis of N-Phenylsulfonyl Substituted Spiro-beta-Lactams,' Tetrahedron: Asymmetry, Mar. 26, 1999 (Mar. 26, 1999), 10(6):1193-9.
Dalla Croce P et al., 'Reaction of Mesoionic Compounds Deriving from Cyclic N-Acyl-alpha-amino Acids with N-(Phenylmethylene)benzenesulfonamide,' Tetrahedron, Jan. 1, 1999 (Jan. 1, 1999), 55(1):201-10.
del Pozo C et al., 'Diastereo- and Enantioselective Synthesis of Novel beta-Lactam-Containing 1,4-Benzodiazepines Through a Ketene-Imine Cycloaddition Reaction,' Eur J Org Chem, Jan. 19, 2004 (Jan. 19, 2004), 2004(3):535-45.
Duman RS, 'Pathophysiology of Depression: The Concept of Synaptic Plasticity,' Eur Psychiatry, Jul. 2002 (Jul. 2002), 17(Suppl 3):306-10.
Erick M Carreira and Lisbet Kvaerno, Classics in Stereoselective Synthesis, (1st ed. 2009), Wiley-Vch Verlag GmbH & Co. KGaA, Weinham, DE (Publ), pp. 19-102 ISBN: 978-3-527-32452-1.
European Patent Office, Supplementary European Search Report (Form 1503) for EP 09 81 5233 (Fink D), completed at Munich DE on Feb. 8, 2012 (Feb. 8, 2012) pp. 1-3.
European Patent Office, Supplementary European Search Report (Form 1503) for EP 10 82 2514 (Fink D), completed at Munich DE on Feb. 1, 2013 (Feb. 1, 2013) pp. 1-2.
Forni A, 'Two Diastereoisomers of 2-(Benzenesulfonyl)-5-benzoyl-1-oxo-3-phenyl-2,5-diazaspiro[3.4]octan-7-yl acetate,' Acta Crystallographica Sec C: Crystal Structure Commun, Sep. 1998 (Sep. 1998), C54(9):1320-2.
Foster AC and Fagg GE, 'Neurobiology: Taking Apart NMDA Receptors,' Nature, Oct. 1, 1987 (Oct. 1, 1987), 329(6138):395-6.
Golik U, 'Synthesis of Malonimide Derivatives as Potential Penicillin Analogs,' J Heterocycl Chem, Feb. 1972 (Feb. 1972), 9(1):21-4.
Grigg R et al., 'X=Y-ZH Systems as Potential 1,3-Dipoles. Part 46. Cascade 1,3-Dipolar Cycloaddition Reactions of Cephalosporin Imines,' Tetrahedron, Nov. 1995 (Nov. 1995), 51(48):13347-56.
Haring R et al., 'Binding Studies and Photoaffinity Labeling Identify Two Classes of Phencyclidine Receptors in Rat Brain,' Biochemistry, Sep. 8, 1987 (Sep. 8, 1987), 26(18):5854-61.
Haring R et al., 'Glycine-Like Modulation of N-Methyl-D-Aspartate Receptors by a Monoclonal Antibody that Enhances Long-Term Potentiation,' J Neurochem, Jul. 1991 (Jul. 1991), 57(1):323-32.
Haring R et al., 'Identification of Polypeptides of the Phencyclidine Receptor of Rat Hippocampus by Photoaffinity Labeling with [H3]Azidophencyclidine,' Biochemistry, Feb. 11, 1986 (Feb. 11, 1986), 25(3):612-20.
Haring R et al., 'Multiple Mode of Binding of Phencyclidines: High Affinity Association Between Phencyclidine Receptors in Rat Brain and a Monovalent Ion-Sensitive Polypeptide,' Biochem Biophys Res Commun, Jan. 30, 1987 (Jan. 30, 1987), 142(2):501-10.
Holderbach R et al., 'Enhanced Long-Term Synaptic Depression in an Animal Model of Depression,' Biol Psychiatry, Dec. 4, 2006 (Dec. 4, 2006) (ePub), 62(1):92-100.
International Searching Authority, International Search Report (ISA/210) for Application No. PCT/US08/77045, (Young LW), completed on Mar. 28, 2009 (Mar. 28, 2009) and mailed on Apr. 29, 2009 (Apr. 29, 2009), pp. 1-3.
International Searching Authority, International Search Report (ISA/210) for Application No. PCT/US09/57401, (Young LW), completed Dec. 6, 2009 (Dec. 6, 2009) and mailed Dec. 24, 2009 (Dec. 24, 2009), pp. 1-2.
International Searching Authority, International Search Report (ISA/210) for Application No. PCT/US09/66536, (Kang YJ), completed Aug. 9, 2010 (Aug. 9, 2010) and mailed Aug. 9, 2010 (Aug. 9, 2010), pp. 1-5.
International Searching Authority, International Search Report (ISA/210) for Application No. PCT/US2014/013619, (Wolf C), completed Mar. 6, 2014 (Mar. 6, 2014) and mailed Mar. 20, 2014 (Mar. 20, 2014), pp. 1-3.
International Searching Authority, International Search Report (ISA/210) for Application No. PCT/US2014/013621, (Wolf C), completed Feb. 27, 2014 (Feb. 27, 2014) and mailed Mar. 13, 2014 (Mar. 13, 2014), pp. 1-2.
International Searching Authority, International Search Report (ISA/210) for Application No. PCT/US2014/013623, (Wolf C), completed Mar. 3, 2014 (Mar. 3, 2014) and mailed Mar. 13, 2014 (Mar. 13, 2014), pp. 1-3.
International Searching Authority, International Search Report (ISA/210) for Application No. PCT/US2014/013626, (Rudolf M), completed Mar. 10, 2014 (Mar. 10, 2014) and mailed Mar. 18, 2014 (Mar. 18, 2014), pp. 1-4.
International Searching Authority, International Search Report (ISA/210) for Application No. PCT/US2014/013639, (Wolf C), completed Feb. 28, 2014 (Feb. 28, 2014) and mailed Mar. 13, 2014 (Mar. 13, 2014), pp. 1-3.
International Searching Authority, Written Opinion of Application No. PCT/US2008/077045 (ISA/237), (Young LW), completed Mar. 28, 2009 (Mar. 28, 2009) and issued Mar. 24, 2010 (Mar. 24, 2010), pp. 1-8.
International Searching Authority, Written Opinion of Application No. PCT/US2009/057401 (ISA/237), (Young LW), completed Dec. 6, 2009 (Dec. 6, 2009) and issued Mar. 22, 2011 (Mar. 22, 2011), pp. 1-6.
International Searching Authority, Written Opinion of Application No. PCT/US2009/066536 (ISA/237), (Kang YJ), completed Aug. 9, 2010 (Aug. 9, 2010) and issued Jun. 7, 2011 (Jun. 7, 2011), pp. 1-8.
International Searching Authority, Written Opinion of Application No. PCT/US2014/013619 (ISA/237), (Wolf C), completed Mar. 6, 2014 (Mar. 6, 2014) and issued Aug. 4, 2015 (Aug. 4, 2015), pp. 1-4.
International Searching Authority, Written Opinion of Application No. PCT/US2014/013621 (ISA/237), (Wolf C), completed Feb. 27, 2014 (Feb. 27, 2014) and issued Aug. 4, 2015 (Aug. 4, 2015), pp. 1-6.
International Searching Authority, Written Opinion of Application No. PCT/US2014/013623 (ISA/237), (Wolf C), completed Mar. 3, 2014 (Mar. 3, 2014) and issued Aug. 4, 2015 (Aug. 4, 2015), pp. 1-4.
International Searching Authority, Written Opinion of Application No. PCT/US2014/013626 (ISA/237), (Rudolf M, completed Mar. 10, 2014 (Mar. 10, 2014) and issued Aug. 4, 2015 (Aug. 4, 2015), pp. 1-6.
International Searching Authority, Written Opinion of Application No. PCT/US2014/013639 (ISA/237), (Wolf C), completed Feb. 28, 2014 (Feb. 28, 2014) and issued Aug. 4, 2015 (Aug. 4, 2015), pp. 1-4.
Johnson JA et al., 'The Preparation of a Double Metallahelicate Containing 28 Copper Atoms,' Angew Chem Int Ed Engl, Feb. 3, 2003 (Feb. 3, 2003), 42(5):546-9.

(56) References Cited

OTHER PUBLICATIONS

Johnson KM and Jones SM, 'Neuropharmacolgy of Phencyclidine: Basic Mechanisms and Therapeutic Potential,' Annu Rev Pharmacol Toxicol, 1990 (1990), 30:707-50.

Khasanov AB et al., 'Novel Asymmetric Approach to Proline-Derived Spiro-beta-Lactams,' J Org Chem., Aug. 20, 2004 (Aug. 20, 2004), 69(17):5766-9.

Kloog Y et al., 'Kinetic Characterization of the Phencyclidine-N-Methyl-d-asparate Receptor Interaction: Evidence for a Steric Blockade of the Channel,' Biochemistry, Feb. 9, 1988 (Feb. 9, 1988), 27(3):843-8.

Kloog Y et al., 'Mode of Binding of [3H]dibenzocycloalkenimine (MK-801) to the N-methyl-D-Aspartate (NMDA) Receptor and its Therapeutic Implication,' FEBS Letts, Mar. 28, 1988 (Mar. 28, 1988), 230(1-2):167-70.

Koller M and Urwyler S, 'Novel N-Methyl-D-aspartate Receptor Antagonists: A Review of Compounds Patented Since 2006,' Expert Opin Ther Pat, Nov. 8, 2010 (Nov. 8, 2010) (epub), 20(12):1683-702.

Kroes RA et al., 'Development of a Novel Glycobiologic Therapy for Glioblastoma,' Neuro-oncol, Oct. 2006 (Oct. 2006), 8(4):397-8, (Abstract #CB-14).

Kroes RA et al., 'Development of a Novel Glycobiology-Based Therapeutic for Glioblastoma,' J Neurochem, Nov. 10, 2006 (Nov. 10, 2006), 99(Suppl. 1):17 (Abstract #50).

Krystall JH et al., 'NMDA Agonists and Antagonists as Probes of Glutamatergic Dysfunction and Pharmacotherapies in Neuropsychiatric Disorders,' Harvard Rev Psychiatry, Sep.-Oct. 1999 (Sep.-Oct. 1999), 7(3):125-43.

Leander JD et al., 'Lack of Ketamine-Like Discriminative Effects of GLYX-13: A Novel NMDA Receptor Glycine Site Functional Partial Agonist with Antidepressant-Like Preclinical Effects,' ACNP 49th Annual Meeting, Dec. 2010 (Dec. 2010), Miami Beach, FL, Naurex, Inc., Evanston, IL (Pub) (Poster #218).

Li G-Q et al., 'N-Heterocyclic Carbene Catalyzed Ring Expansion of 4-Formyl-beta-lactams: Synthesis of Succinimide Derivatives,' Org Lett, Aug. 9, 2007 (Aug. 9, 2007) (ePub), 9(18):3519-21.

Lynch G et al., 'Synaptic Pasticity in Early Aging,' Ageing Res Rev, Aug. 28, 2006 (Aug. 28, 2006) (ePub), 5(3):255-80.

Macias A et al., 'Diastereoselective [2+2]-Cycloaddition Reactions of Unsymmetrical Cyclic Ketenes with Imines: Synthesis of Modified Prolines and Theoretical Study of the Reaction Mechanism,' J Org Chem, Oct. 1, 2004 (Oct. 1, 2004) Sep. 10, 2005 (Sep. 10, 2005)(ePub), 69(21):7004-12.

Macias A et al., 'Unusual Rearrangement of Spiro-beta-Lactams to 1,4-diazabicyclo[4,4,0]decanes and 1,4-diazabicyclo[4,3,0]nonanes. Synthesis of Conformationally Restricted Sigma-Receptor Ligands,' Tetrahedron Lett, Jun. 2004 (Jun. 2004), 45(24):4657-60.

Marcias A et al., 'Synthesis of Enantiopure Pyrrolidine-Derived Peptidomimetics and Oligo-beta-Peptides via Nucleophilic Ring-Opening of beta-Lactams,' J Org Chem, Sep. 29, 2006 (Sep. 29, 2006), 71(20):7721-30.

Mayer ML and Miller RJ, 'Excitatory Amino Acid Receptors, Second Messengers and Regulation of Intracellular Ca2+ in Mammalian Neurons,' Trends Pharmacol Sci, Jun. 1990 (Jun. 1990), 11(6):254-60.

McLeod MN et al., 'Chromium Potentiation of Antidepressant Pharmacotherapy for Dysthymic Disorder in 5 Patients,' J Clin Psychiatry, Apr. 1999 (Apr. 1999), 60(4):237-40.

Mishra H et al., 'Three-Dimensional Quantitative Structure-Activity Relationship and Comparative Molecular Field Analysis of Dipeptide Hydroxamic Acid Helicobacter pylori Urease Inhibitors,' Antimicrob Agents Chemother, Aug. 2002 (Aug. 2002), 46(8):2613-8.

Monahan JB et al., 'D-Cycloserine, a Positive Modulator of the N-Methyl-d-Asparate Receptor, Enhances Performance of Learning in Rats,' Pharmacol Biochem Behav, Nov. 1989 (Nov. 1989), 34(3):649-53.

Moskal JR and Burgdorf JS, 'The Antidepressant and Anxiolytic Properties of GLYX-13: A Novel NMDA Receptor Glycine Site Functional Partial Agonist,' ACNP 29th Annual Meeting, Dec. 7, 2009 (Dec. 7, 2009), Hollywood, FL, Naurex, Inc. Evanston, IL (Pub) (Poster #059).

Moskal JR and Schaffner AE, 'Monoclonal Antibodies to the Dentate Gyrus: Immunocytochemical Characterization and Flow Cytometric Analysis of Hippocampal Neurons Bearing a Unique Cell-Surface Antigen,' J Neurosci, Jul. 1986 (Jul. 1986), 6(7):2045-53.

Moskal JR et al., 'A Novel Approach to Unlocking the Therapeutic Potential of the NMDA Receptor,' Vital Signs e-Magazine, Sep. 2010 (Sep. 2010), pp. 1-2.

Moskal JR et al., 'GLYX-13: A Monoclonal Antibody-Derived Peptide that Acts as an N-Methyl-D-Aspartate Receptor Modulator,' Neuropharmacol, Jul. 26, 2005 (Jul. 26, 2005) (ePub), 49(7):1077-87.

Moskal JR et al., 'The Use of Antibody Engineering to Create Novel Drugs that Target N-Methyl-D-Aspartate Receptors,' Curr Drug Targets, Sep. 2001 (Sep. 2001), 2(3):331-45.

Moskal JR, 'The Anti-depressant and Anxiolytic Properties of GLYX-13: A Glycine-site Functional Partial Agonist (GFPA), a Novel Mechanism for Modulating NMDA,' ACNP 48th Annual Meeting, Dec. 7, 2009 (Dec. 7, 2009), Hollywood, FL, pp. 1-2 (Abstract).

Myers SM and Johnson CP, 'Management of Children with Autism Spectrum Disorders,' Pediatrics, Oct. 29, 2007 (Oct. 29, 2007) (ePub), 120(5):1162-82.

Narahashi T et al., 'Mechanisms of Action of Cognitive Enhancers on Neuroreceptors,' Biol Pharm Bull, Nov. 2004 (Nov. 2004), 27(11):1701-6.

Overman LE and Osawa T, 'A Convenient Synthesis of 4-Unsubstituted beta-Lactams,' J Am Chem Soc, Mar. 1985 (Mar. 1985), 107(6):1698-701.

Parac-Vogt TN et al., 'Pentacopper(II) Complexes of alpha-Aminohydroxamic Acids: Uranyl-Induced Conversion of a 12-Metallacrown-4 to a 15-Metallacrown-5,' J Inorg Biochem, Nov. 21, 2004 (Nov. 21, 2004) (ePub), 99(2):497-504.

Pittenger C et al., 'The NMDA Receptor as a Therapeutic Target in Major Depressive Disorder,' CNS Neurol Disord Targets, Apr. 2007 (Apr. 2007), 6(2):101-15.

Raghavan B et al., 'Allosteric Modulation of the Dopamine D2 Receptor by Pro-Leu-Gly-NH2 Peptidomimetics Constrained in Either a Polyproline II Helix or a Type II beta-Turn Conformation,' J Med Chem, Apr. 9, 2009 (Apr. 9, 2009), 52(7):2043-51.

Ransom RW and Stec NL, 'Cooperative Modulation of [3H]MK-801 Binding to the N-Methyl- d-Asparate Receptor-Ion Channel Complex by I-Glumate, Glycine, and Polyamines,' J Neurochem, Sep. 1988 (Sep. 1988), 51(3):830-6.

Rasmusson GH et al., '6-Substituted Penicillin Derivatives,' Tetrahedron Lett, 1973 (1973), 14(2):145-8.

Rautio J et al., 'Prodrugs: Design and Clinical Applications,' Nat Rev Drug Discov, Mar. 2008 (Mar. 2008), 7(3):255-70.

Schell MJ, 'The N-methyl D-aspartate Receptor Glycine Site and D-serine Metabolism: An Evolutionary Perspective,' Philos Trans R Soc Lond B Biol Sci, Jun. 29, 2004 (Jun. 29, 2004), 359(1446):943-64.

Shankar GM and Walsh DM, 'Alzheimer's Disease: Synaptic Dysfunction and A-beta,' Mol Neurodegen, Nov. 23, 2009 (Nov. 23, 2009), 4:48-61.

Siemion IZ et al., 'Conformational Preferences of the Sequential Fragments of the Hinge Region of the Human IgA1 Immunoglobulin Molecule,' Biophys Chem, Aug. 1988 (Aug. 1988), 31(1-2):35-44.

Simplício AL et a;., 'Prodrugs for Amines,' Molecules, Mar. 2008 (Mar. 2008), 13(3):519-47.

Stanton PK et al., 'Inhibition of the Production and Maintenance of Long-Term Potentiation in Rat Hippocampal Slices by a Monoclonal Antibody,' Proc Natl Acad Sci USA, Mar. 1987 (Mar. 1987), 84(6):1684-8.

Stanton PK et al., 'Neuroprotection by a Novel NMDAR Functional Glycine Site Partial Agonist, GLYX-13,' Neuroreport, Aug. 26, 2009 (Aug. 26, 2009), 20(13):1193-7.

(56) References Cited

OTHER PUBLICATIONS

Tanwar MK et al., 'Gene Expression Microarray Analysis Reveals YLK-40 to be a Potential Serum Marker for Malignant Character in Human Glioma,' Cancer Res, Aug. 1, 2002 (Aug. 1, 2002), 62(15):4364-8.
Thompson LT et al., 'Hippocampus-Dependent Learning Facilitated by a Monoclonal Antibody or D-Cycloserine,' Nature, Oct. 15, 1992 (Oct. 15, 1992), 359(6396):638-41.
Turturro A et al., 'Growth Curves and Survival Characteristics of the Animals Used in the Biomarkers of Aging Program,' J Gerentol A Biol Sci Med Sci, Nov. 1999 (Nov. 1999), 54A(11):B492-B501.
Various, *The NMDA Receptor,* (2nd ed. 1994), GL Collingridge and JC Watkins Eds., Oxford University Press, Inc., New York, New York US (Publ), pp. 1-479 ISBN: 0-19-262371-0.
Wood PL et al., 'Antinociceptive Action of GLYX-13: An N-Methyl-D-aspartate Receptor Glycine Site Partial Agonist,' Neuroreport, Jul. 2, 2008 (Jul. 2, 2008), 19(10):1061-3.
Wood PL, 'The NMDA Receptor Complex: A Long and Winding Road to Therapeutics,' IDrugs, Mar. 2005 (Mar. 2005), 8(3):229-35.
Wood SG et al., 'Tetrapeptide Inhibitors of the IgA1 Proteinases from Type I Neisseria gonorrhoeae,' J Med Chem, Oct. 1989 (Oct. 1989), 32(10):2407-11.
Zhang X-L et al., 'A NMDA Receptor Glycine Site Partial Agonist, GLYX-13, Simultaneously Enhances LTP and Reduces LTD at Schaffer Collateral-CA1 Synapses in Hippocampus,' Neuropharmacology, Aug. 29, 2008 (Aug. 29, 2008), 55(7):1238-50.
U.S. Appl. No. 14/764,395, Spiro-Lactam NMDA Modulators and Uses Thereof, filed Jul. 29, 2015, pending.
U.S. Appl. No. 15/049,577, Spiro-Lactam NMDA Modulators and Uses Thereof, filed Feb. 22, 2016, pending.
U.S. Appl. No. 14/764,402, Spiro-Lactam NMDA Modulators and Uses Thereof, filed Jul. 29, 2015.
U.S. Appl. No. 14/764,411, Spiro-Lactam NMDA Modulators and Uses Thereof, filed Jul. 29, 2015.
U.S. Appl. No. 14/764,419, Spiro-Lactam NMDA Modulators and Uses Thereof, filed Jul. 29, 2015.
U.S. Appl. No. 14/764,426, Spiro-Lactam NMDA Modulators and Uses Thereof, filed Jul. 29, 2015.
Singapore Search Report and Written Opinon issued for corresponding Singapore application No. 11201505860X, dated Apr. 18, 2016.
Singapore Search Report and Written Opinon issued for corresponding Singapore application No. 11201505942Y, dated Mar. 22, 2016.
Singapore Search Report and Written Opinon issued for corresponding Singapore application No. 11201505934X, dated Apr. 27, 2016.
Singapore Search Report and Written Opinon issued for corresponding Singapore application No. 11201505862T, dated Apr. 18, 2016.
Singapore Search Report and Written Opinon issued for corresponding Singapore application No. 11201505937S, dated May 5, 2016.

\* cited by examiner

SPIRO-LACTAM NMDA RECEPTOR MODULATORS AND USES THEREOF

CROSS REFERENCE TO RELATED APPLICATIONS

This application is a continuation application of U.S. application Ser. No. 14/764,395 filed Jul. 29, 2015, which is a National Stage Entry of International Application Serial No. PCT/US14/013619 filed Jan. 29, 2014, which claims the benefit of and priority to U.S. Provisional Application Ser. No. 61/757,903, filed on Jan. 29, 2013, each of which is incorporated by reference in their entirety.

BACKGROUND

An N-methyl-d-aspartate (NMDA) receptor is a postsynaptic, ionotropic receptor that is responsive to, inter alia, the excitatory amino acids glutamate and glycine and the synthetic compound NMDA. The NMDA receptor controls the flow of both divalent and monovalent ions into the postsynaptic neural cell through a receptor associated channel (Foster et al., Nature 1987, 329:395-396; Mayer et al., Trends in Pharmacol. Sci. 1990, 11:254-260). The NMDA receptor has been implicated during development in specifying neuronal architecture and synaptic connectivity, and may be involved in experience-dependent synaptic modifications. In addition, NMDA receptors are also thought to be involved in long term potentiation and central nervous system disorders.

The NMDA receptor plays a major role in the synaptic plasticity that underlies many higher cognitive functions, such as memory acquisition, retention and learning, as well as in certain cognitive pathways and in the perception of pain (Collingridge et al., The NMDA Receptor, Oxford University Press, 1994). In addition, certain properties of NMDA receptors suggest that they may be involved in the information-processing in the brain that underlies consciousness itself.

The NMDA receptor has drawn particular interest since it appears to be involved in a broad spectrum of CNS disorders. For instance, during brain ischemia caused by stroke or traumatic injury, excessive amounts of the excitatory amino acid glutamate are released from damaged or oxygen deprived neurons. This excess glutamate binds to the NMDA receptors which opens their ligand-gated ion channels; in turn the calcium influx produces a high level of intracellular calcium which activates a biochemical cascade resulting in protein degradation and cell death. This phenomenon, known as excitotoxicity, is also thought to be responsible for the neurological damage associated with other disorders ranging from hypoglycemia and cardiac arrest to epilepsy. In addition, there are preliminary reports indicating similar involvement in the chronic neurodegeneration of Huntington's, Parkinson's, and Alzheimer's diseases. Activation of the NMDA receptor has been shown to be responsible for post-stroke convulsions, and, in certain models of epilepsy, activation of the NMDA receptor has been shown to be necessary for the generation of seizures. Neuropsychiatric involvement of the NMDA receptor has also been recognized since blockage of the NMDA receptor $Ca^{++}$ channel by the animal anesthetic PCP (phencyclidine) produces a psychotic state in humans similar to schizophrenia (reviewed in Johnson, K. and Jones, S., 1990). Further, NMDA receptors have also been implicated in certain types of spatial learning.

The NMDA receptor is believed to consist of several protein chains embedded in the postsynaptic membrane. The first two types of subunits discovered so far form a large extracellular region, which probably contains most of the allosteric binding sites, several transmembrane regions looped and folded so as to form a pore or channel, which is permeable to $Ca^{++}$, and a carboxyl terminal region. The opening and closing of the channel is regulated by the binding of various ligands to domains (allosteric sites) of the protein residing on the extracellular surface. The binding of the ligands is thought to affect a conformational change in the overall structure of the protein which is ultimately reflected in the channel opening, partially opening, partially closing, or closing.

NMDA receptor compounds may exert dual (agonist/antagonist) effect on the NMDA receptor through the allosteric sites. These compounds are typically termed "partial agonists". In the presence of the principal site ligand, a partial agonist will displace some of the ligand and thus decrease $Ca^{++}$ flow through the receptor. In the absence of or lowered level of the principal site ligand, the partial agonist acts to increase $Ca^{++}$ flow through the receptor channel.

A need continues to exist in the art for novel and more specific/potent compounds that are capable of binding the glycine binding site of NMDA receptors, and provide pharmaceutical benefits. In addition, a need continues to exist in the medical arts for orally deliverable forms of such compounds.

SUMMARY

Provided herein, at least in part, are compounds that are NMDA modulators, for example, partial agonists of NMDA. For example, disclosed herein are compounds represented by the formula:

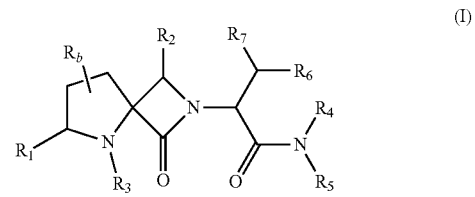

and pharmaceutically acceptable salts, stereoisomers, and N-oxides thereof, wherein $R_b$ is selected from the group consisting of H, halogen, hydroxyl, cyano and $C_1$-$C_6$ alkyl;

$R_1$ is H or $C_1$-$C_6$ alkyl;

$R_2$ is H or $C_1$-$C_6$ alkyl;

$R_3$ is selected from the group consisting of H, $C_1$-$C_6$ alkyl and a nitrogen protecting group;

$R_4$ and $R_5$ are independently H or $C_1$-$C_6$ alkyl, or $R_4$ and $R_5$ taken together with the nitrogen to which they are attached form a 4-, 5- or 6-membered heterocyclic or heteroaryl ring optionally substituted with one or more substituents selected from the group consisting of halogen, cyano, oxo, $C_1$-$C_6$ alkyl, —OH, $C_1$-$C_6$ alkoxy, and —N(R')R', wherein R' is independently selected for each occurrence from H or $C_1$-$C_6$ alkyl;

$R_6$ is selected from the group consisting of —OH, $C_1$-$C_6$ alkoxy, —OC(O)—$C_1$-$C_6$ alkyl, and —OC(O)phenyl; and $R_7$ is H or $C_1$-$C_6$ alkyl;

or in other embodiments, the variables set forth in formula (I) are defined as follows:

$R_b$ is selected from the group consisting of H, halogen, hydroxyl, cyano and $C_1$-$C_6$ alkyl (e.g., H);

$R_1$ is H or $C_1$-$C_6$ alkyl;

$R_2$ is H or $C_1$-$C_6$ alkyl;

$R_3$ is selected from the group consisting of H, $C_1$-$C_6$ alkyl and a nitrogen protecting group;

$R_4$ and $R_5$ are each independently selected from the group consisting of H, $C_1$-$C_6$ alkyl, X, and —$C_1$-$C_6$ alkylene-X, wherein X is selected from the group consisting of:
  (i) $C_3$-$C_6$ cycloalkyl;
  (ii) heteroaryl including from 5 to 6 ring atoms wherein 1, 2, or 3 of the ring atoms are independently selected from the group consisting of N, NH, N(C1-C3 alkyl), O, and S;
  (iii) heterocyclyl including from 3 to 6 ring atoms wherein 1, 2, or 3 of the ring atoms are independently selected from the group consisting of N, NH, N(C1-C3 alkyl), O, and S; and
  (iv) phenyl;

wherein $C_3$-$C_6$ cycloalkyl and heterocyclyl are each optionally substituted with from 1-3 substituents independently selected from the group consisting of halogen, cyano, oxo, $C_1$-$C_6$ alkyl, hydroxyl, $C_1$-$C_6$ alkoxy, and —N(R')R', wherein R' is independently selected for each occurrence from H and $C_1$-$C_6$ alkyl; and heteroaryl and phenyl are each optionally substituted with from 1-3 substituents independently selected from the group consisting of halogen, cyano, $C_1$-$C_6$ alkyl, hydroxyl, $C_1$-$C_6$ alkoxy, and —N(R')R';

or $R_4$ and $R_5$ together with the nitrogen to which they are attached form:
  heterocyclyl including from 4 to 6 ring atoms; wherein the heterocyclyl includes not more than two ring heteroatoms (including the nitrogen atom attached to $R_4$ and $R_5$), and the second ring heteroatom, when present, is independently selected from the group consisting of N, NH, N(C1-C3 alkyl), O, and S; and wherein the heterocyclyl is optionally substituted with from 1-3 substituents independently selected from the group consisting of halogen, cyano, oxo, $C_1$-$C_6$ alkyl, hydroxyl, $C_1$-$C_6$ alkoxy, and —N(R')R'; or
  heteroaryl including from 5 to 6 ring atoms; wherein the heteroaryl includes not more than four ring heteroatoms (including the nitrogen atom attached to $R_4$ and $R_5$), and each additional ring heteroatom, when present, is independently selected from the group consisting of N, NH, N(C1-C3 alkyl), O, and S; and wherein the heteroaryl is optionally substituted with from 1-3 substituents independently selected from the group consisting of halogen, cyano, $C_1$-$C_6$ alkyl, hydroxyl, $C_1$-$C_6$ alkoxy, and —N(R')R';

$R_6$ is selected from the group consisting of —OH, $C_1$-$C_6$ alkoxy, —OC(O)—$C_1$-$C_6$ alkyl, —OC(O)phenyl, and —N(R')R'; and $R_7$ is H or $C_1$-$C_6$ alkyl.

Also provided herein are pharmaceutically acceptable compositions comprising a disclosed compound, and a pharmaceutically acceptable excipient. For example, such compositions may be suitable for oral or intravenous administration to a patient.

In another aspect, a method of treating a condition selected from the group consisting of autism, anxiety, depression, bipolar disorder, attention deficit disorder, attention deficit hyperactivity disorder (ADHD), schizophrenia, a psychotic disorder, a psychotic symptom, social withdrawal, obsessive-compulsive disorder, phobia, post-traumatic stress syndrome, a behavior disorder, an impulse control disorder, a substance abuse disorder, a sleep disorder, a memory disorder, a learning disorder, urinary incontinence, multiple system atrophy, progressive supra-nuclear palsy, Friedrich's ataxia, Down's syndrome, fragile X syndrome, tuberous sclerosis, olivio-ponto-cerebellar atrophy, cerebral palsy, drug-induced optic neuritis, ischemic retinopathy, diabetic retinopathy, glaucoma, dementia, AIDS dementia, Alzheimer's disease, Huntington's chorea, spasticity, myoclonus, muscle spasm, Tourette's syndrome, epilepsy, cerebral ischemia, stroke, a brain tumor, traumatic brain injury, cardiac arrest, myelopathy, spinal cord injury, peripheral neuropathy, acute neuropathic pain, and chronic neuropathic, in a patient in need thereof is provided. Such methods may comprise administering to the patient a pharmaceutically effective amount of a disclosed compound or pharmaceutically acceptable salts, stereoisomers, N-oxides, and hydrates thereof.

In some embodiments, a contemplated method includes treating depression. For example, depression may include one or more of major depressive disorder, dysthymic disorder, psychotic depression, postpartum depression, seasonal affective disorder, bipolar disorder, mood disorder, or depression caused by a chronic medical condition. In other embodiments, a contemplated method may treat schizophrenia. Such schizophrenia may be, for example, paranoid type schizophrenia, disorganized type schizophrenia, catatonic type schizophrenia, undifferentiated type schizophrenia, residual type schizophrenia, post-schizophrenic depression, or simple schizophrenia.

DETAILED DESCRIPTION

Figure 1:
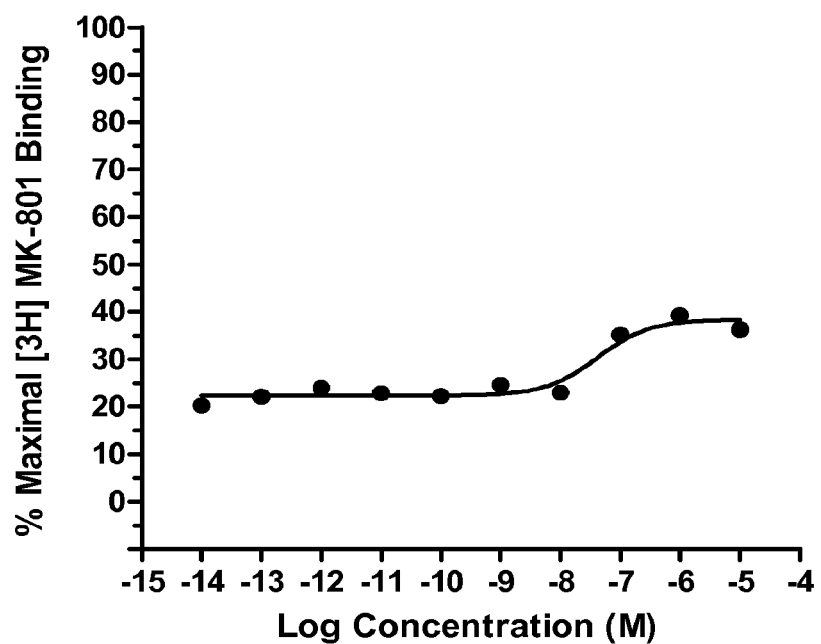
FIG. 1 shows the potentiation of [$^3$H]MK-801 binding in the presence of Compound X.

This disclosure is generally directed to compounds that are capable of modulating NMDA, e.g., NMDA antagonists or partial agonists, and compositions and/or methods of using the disclosed compounds.

Definitions

"Treating" includes any effect, e.g., lessening, reducing, modulating, or eliminating, that results in the improvement of the condition, disease, disorder and the like.

The term "alkenyl" as used herein refers to an unsaturated straight or branched hydrocarbon having at least one carbon-carbon double bond, such as a straight or branched group of 2-6 or 3-4 carbon atoms, referred to herein for example as $C_2$-$C_6$ alkenyl, and $C_3$-$C_4$ alkenyl, respectively. Exemplary alkenyl groups include, but are not limited to, vinyl, allyl, butenyl, pentenyl, etc.

The term "alkoxy" as used herein refers to a straight or branched alkyl group attached to an oxygen (alkyl-O—). Exemplary alkoxy groups include, but are not limited to, alkoxys of 1-6 or 2-6 carbon atoms, referred to herein as $C_1$-$C_6$ alkoxy, and $C_2$-$C_6$ alkoxy, respectively. Exemplary alkoxy groups include, but are not limited to methoxy, ethoxy, isopropoxy, etc.

The term "alkenyloxy" used herein refers to a straight or branched alkenyl group attached to an oxygen (alkenyl-O). Exemplary alkenoxy groups include, but are not limited to, groups with an alkenyl group of 3-6 carbon atoms, (also e.g. referred to as $C_3$-$C_6$ alkenyloxy). Exemplary "alkenoxy" groups include, but are not limited to allyloxy, butenyloxy, etc.

The term "alkynyloxy" used herein refers to a straight or branched alkynyl group attached to an oxygen (alkynyl-O)). Exemplary alkynyloxy groups include, but are not limited to, $C_3$-$C_6$ alkynyloxy, e.g., propynyloxy.

The term "alkyl" as used herein refers to a saturated straight or branched hydrocarbon, such as a straight or branched group of 1-6, 1-4, or 1-3 carbon atoms, referred to herein as $C_1$-$C_6$ alkyl, $C_1$-$C_4$ alkyl, and $C_1$-$C_3$ alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 3-methyl-2-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, etc. The term "haloalkyl" as used herein refers to a saturated straight or branched alkyl groups, in which one or more hydrogen atoms of the alkyl group are replaced with one or more independently selected halogens. The term "haloalkyl" encompasses alkyl groups in which all of hydrogen atoms of the alkyl group are replaced independently selected halogens (sometimes referred to as "perhalo" alkyl groups. Exemplary haloalkyl groups include, but are not limited to, $CH_2F$, $CH_2CH_2Cl$, $CF_3$, $CHFCH_2Cl$.

The term "alkynyl" as used herein refers to an unsaturated straight or branched hydrocarbon having at least one carbon-carbon triple bond, such as a straight or branched group of 2-6, or 3-6 carbon atoms, referred to herein as $C_2$-$C_6$ alkynyl, and $C_3$-$C_6$ alkynyl, respectively. Exemplary alkynyl groups include, but are not limited to, ethynyl, propynyl, butynyl, pentynyl, hexynyl, methylpropynyl, etc.

The term "bridged cycloalkyl", as used herein, is defined as a monocyclic 4- to 7-membered cycloalkyl group in which two non-adjacent atoms are linked by a $CH_2$ or $CH_2CH_2$ group. A "bridged cycloalkyl" may be fused to one or more phenyl, partially unsaturated, or saturated rings. Examples of bridged carbocyclic groups include but are not limited to bicyclo[2.2.1]heptane, bicyclo[2.2.2]octane, bicyclo[2.2.2]octene etc.

The term "carbonyl" as used herein refers to the radical —C(O)—. The term "cyano" as used herein refers to the radical —CN. The term "nitro" refers to the radical —$NO_2$. The term "H" refers to hydrogen.

The term "cycloalkoxy" as used herein refers to a cycloalkyl group attached to an oxygen (cycloalkyl-O—).

The term "cycloalkyl" as used herein refers to a monocyclic saturated or particularly unsaturated hydrocarbon group of for example 3-6, or 4-6 carbons, referred to herein, e.g., as "$C_{3-6}$ cycloalkyl" or "$C_{4-6}$ cycloalkyl," and derived from a cycloalkane. Exemplary cycloalkyl groups include, but are not limited to, cyclohexane, cyclohexene, cyclopentane, cyclobutane, cyclopropane or cyclopentane.

The terms "halo" or "halogen" as used herein refer to F, Cl, Br, or I.

The terms "heteroaryl" as used herein refers to a monocyclic aromatic 4-6 membered ring system containing one or more heteroatoms, for example one to three heteroatoms, such as nitrogen, oxygen, and sulfur. Where possible, said heteroaryl ring may be linked to the adjacent radical though carbon or nitrogen. Examples of heteroaryl rings include but are not limited to furan, thiophene, pyrrole, thiazole, oxazole, isothiazole, isoxazole, imidazole, pyrazole, triazole, pyridine, and pyrimidine.

The terms "heterocyclyl" or "heterocyclic group" are art-recognized and refer to saturated or partially unsaturated 4- to 7-membered ring structures, whose ring structures include one to three heteroatoms, such as nitrogen, oxygen, and sulfur. A heterocycle may be fused to one or more phenyl, partially unsaturated, or saturated rings. Examples of heterocyclyl groups include but are not limited to pyrrolidine, piperidine, morpholine, thiomorpholine, and piperazine.

The term "heterocyclylalkoxy" as used herein refers to a heterocyclyl-alkyl-O-group.

The term "heterocyclyloxyalkyl" refers to a heterocyclyl-O-alkyl-group.

The term "heterocycloxy" refers to a heterocyclyl-O— group. The term "cycloalkyloxy" refers to a cycloalkyl-O— group.

The term "heteroaryloxy" refers to a heteroaryl-O— group.

The terms "hydroxy" and "hydroxyl" as used herein refers to the radical —OH.

The term "oxo" as used herein refers to the radical =O.

The term "nitrogen protecting group" or "amino protecting group" is art-recognized and as used herein refers to a chemical moiety that is covalently linked to a nitrogen atom of an amino (primary or secondary) group and that temporarily blocks the reactivity of the amino group during a synthetic step and is selectively removed once the synthetic step is complete. Nitrogen protecting groups include, for example, 9-Fluorenylmethyloxycarbonyl (Fmoc), tert-butoxycarbonyl (Boc), carbobenzyloxycarbonyl (Cbz), p-methoxybenzyloxycarbonyl, acetyl, trifluoroacetyl, benzoyl, phthalimido, benzyl (Bn), p-methoxybenzyl, p-methoxyphenyl, 3,4-dimethoxybenzyl, triphenylmethyl, benzylidene, and p-toluenesulfonyl (Ts). In some embodiments, the nitrogen protecting group can have one of the following formulas: —C(O)O$R_{31}$ or —C(O)$R_{32}$ as defined herein.

As used in the present disclosure, the term "partial NMDA receptor agonist" generally refers to a compound that is capable of binding to a glycine binding site of an NMDA receptor; at low concentrations a NMDA receptor agonist acts substantially as agonist and at high concentrations it acts substantially as an antagonist. These concentrations are experimentally determined for each and every "partial agonist.

"Pharmaceutically or pharmacologically acceptable" include molecular entities and compositions that do not produce an adverse, allergic or other untoward reaction when administered to an animal, or a human, as appropriate. For human administration, preparations should meet sterility, pyrogenicity, general safety and purity standards as required by FDA Office of Biologics standards.

The term "pharmaceutically acceptable carrier" or "pharmaceutically acceptable excipient" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

The term "pharmaceutical composition" as used herein refers to a composition comprising at least one compound as disclosed herein formulated together with one or more pharmaceutically acceptable carriers.

"Individual," "patient," or "subject" are used interchangeably and include any animal, including mammals, preferably mice, rats, other rodents, rabbits, dogs, cats, swine, cattle, sheep, horses, or primates, and most preferably humans. The compounds of the invention can be administered to a mammal, such as a human, but can also be administered to other mammals such as an animal in need of veterinary treatment, e.g., domestic animals (e.g., dogs, cats, and the like), farm animals (e.g., cows, sheep, pigs, horses, and the like) and laboratory animals (e.g., rats, mice, guinea pigs, and the like). The mammal treated in the methods of the invention is desirably a mammal in which treatment e.g., of pain or depression is desired. "Modulation" includes antagonism (e.g., inhibition), agonism, partial antagonism and/or partial agonism.

In the present specification, the term "therapeutically effective amount" means the amount of the subject compound that will elicit the biological or medical response of a tissue, system, animal or human that is being sought by the researcher, veterinarian, medical doctor or other clinician. The compounds of the invention are administered in therapeutically effective amounts to treat a disease. Alternatively, a therapeutically effective amount of a compound is the quantity required to achieve a desired therapeutic and/or prophylactic effect, such as an amount which results in lessening a symptom of depression.

The term "pharmaceutically acceptable salt(s)" as used herein refers to salts of acidic or basic groups that may be present in compounds used in the present compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including but not limited to malate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that are acidic in nature are capable of forming base salts with various pharmacologically acceptable cations. Examples of such salts include alkali metal or alkaline earth metal salts and, particularly, calcium, magnesium, sodium, lithium, zinc, potassium, and iron salts. Compounds included in the present compositions that include a basic or acidic moiety may also form pharmaceutically acceptable salts with various amino acids. The compounds of the disclosure may contain both acidic and basic groups; for example, one amino and one carboxylic acid group. In such a case, the compound can exist as an acid addition salt, a zwitterion, or a base salt.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," depending on the configuration of substituents around the stereogenic carbon atom. The present invention encompasses various stereoisomers of these compounds and mixtures thereof. Stereoisomers include enantiomers and diastereomers. Mixtures of enantiomers or diastereomers may be designated "(±)" in nomenclature, but the skilled artisan will recognize that a structure may denote a chiral center implicitly.

The compounds of the disclosure may contain one or more chiral centers and/or double bonds and, therefore, exist as geometric isomers, enantiomers or diastereomers. The enantiomer and diastereomers may be designated by the symbols "(+)," "(−)." "R" or "S," depending on the configuration of substituents around the stereogenic carbon atom, but the skilled artisan will recognize that a structure may denote a chiral center implicitly. Geometric isomers, resulting from the arrangement of substituents around a carbon-carbon double bond or arrangement of substituents around a cycloalkyl or heterocyclic ring, can also exist in the compounds of the present invention. The symbol ⋯⋯⋯ denotes a bond that may be a single, double or triple bond as described herein. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers. Substituents around a carbon-carbon double bond alternatively can be referred to as "cis" or "trans," where "cis" represents substituents on the same side of the double bond and "trans" represents substituents on opposite sides of the double bond. The arrangement of substituents around a carbocyclic ring can also be designated as "cis" or "trans." The term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

The term "stereoisomers" when used herein consist of all geometric isomers, enantiomers or diastereomers. The present invention encompasses various stereoisomers of these compounds and mixtures thereof.

Individual enantiomers and diasteriomers of compounds of the present invention can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, (3) direct separation of the mixture of optical enantiomers on chiral liquid chromatographic columns or (4) kinetic resolution using stereoselective chemical or enzymatic reagents. Racemic mixtures can also be resolved into their component enantiomers by well-known methods, such as chiral-phase gas chromatography or crystallizing the compound in a chiral solvent. Stereoselective syntheses, a chemical or enzymatic reaction in which a single reactant forms an unequal mixture of stereoisomers during the creation of a new stereocenter or during the transformation of a pre-existing one, are well known in the art. Stereoselective syntheses encompass both enantio- and diastereoselective transformations. For examples, see Carreira and Kvaerno, *Classics in Stereoselective Synthesis*, Wiley-VCH: Weinheim, 2009.

The compounds disclosed herein can exist in solvated as well as unsolvated forms with pharmaceutically acceptable solvents such as water, ethanol, and the like, and it is intended that the invention embrace both solvated and unsolvated forms. In one embodiment, the compound is amorphous. In one embodiment, the compound is a single polymorph. In another embodiment, the compound is a mixture of polymorphs. In another embodiment, the compound is in a crystalline form.

The invention also embraces isotopically labeled compounds of the invention which are identical to those recited herein, except that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. For example, a compound of the invention may have one or more H atom replaced with deuterium.

Certain isotopically-labeled disclosed compounds (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances, Isotopically labeled compounds of the invention can generally be prepared by following procedures analogous to those disclosed in the e.g., Examples herein by substituting an isotopically labeled reagent for a non-isotopically labeled reagent.

The term "prodrug" refers to compounds that are transformed in vivo to yield a disclosed compound or a pharmaceutically acceptable salt, hydrate or solvate of the compound. The transformation may occur by various mechanisms (such as by esterase, amidase, phosphatase, oxidative and or reductive metabolism) in various locations (such as in the intestinal lumen or upon transit of the intestine, blood or liver). Prodrugs are well known in the art (for example, see Rautio, Kumpulainen, et al, Nature Reviews Drug Discovery 2008, 7, 255). For example, if a compound of the invention or a pharmaceutically acceptable salt, hydrate or solvate of the compound contains a carboxylic acid functional group, a prodrug can comprise an ester formed by the replacement of the hydrogen atom of the acid group with a group such as $(C_1-C_8)$alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di$(C_1-C_2)$ alkylcarbamoyl-$(C_1-C_2)$alkyl and piperidino-, pyrrolidino- or morpholino$(C_2-C_3)$alkyl.

Similarly, if a compound of the invention contains an alcohol functional group, a prodrug can be formed by the replacement of the hydrogen atom of the alcohol group with a group such as $(C_1-C_6)$alkanoyloxymethyl, 1-(($(C_1-C_6)$alkanoyloxy)ethyl, 1-methyl-1-(($(C_1-C_6)$alkanoyloxy)ethyl $(C_1-C_6)$alkoxycarbonyloxymethyl, N—$(C_1-C_6)$alkoxycarbonylaminomethyl, succinoyl, $(C_1-C_6)$alkanoyl, α-amino $(C_1-C_4)$alkanoyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1-C_6)alkyl)_2$ or glycosyl (the radical resulting from the removal of a hydroxyl group of the hemiacetal form of a carbohydrate).

If a compound of the invention incorporates an amine functional group, a prodrug can be formed, for example, by creation of an amide or carbamate, an N-acyloxyakyl derivative, an (oxodioxolenyl)methyl derivative, an N-Mannich base, imine or enamine. In addition, a secondary amine can be metabolically cleaved to generate a bioactive primary amine, or a tertiary amine can metabolically cleaved to generate a bioactive primary or secondary amine. For examples, see Simplicio, et al., *Molecules* 2008, 13, 519 and references therein.

Compounds

Disclosed compounds include those represented by the formula:

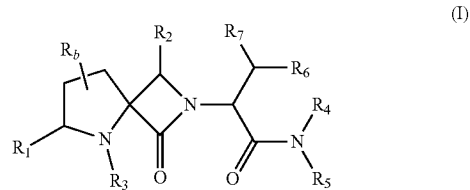

(I)

and pharmaceutically acceptable salts, stereoisomers, and N-oxides thereof, wherein $R_b$ is selected from the group consisting of H, halogen, hydroxyl, cyano and $C_1-C_6$ alkyl;

$R_1$ is H or $C_1-C_6$ alkyl;

$R_2$ is H or $C_1-C_6$ alkyl;

$R_3$ is selected from the group consisting of H, $C_1-C_6$ alkyl and a nitrogen protecting group;

$R_4$ and $R_5$ are independently H or $C_1-C_6$ alkyl, or $R_4$ and $R_5$ taken together with the nitrogen to which they are attached form a 4-, 5- or 6-membered heterocyclic or heteroaryl ring optionally substituted with one or more substituents selected from the group consisting of halogen, cyano, oxo, $C_1-C_6$ alkyl, —OH, $C_1-C_6$ alkoxy, and —N(R')R', wherein R' is independently selected for each occurrence from H or $C_1-C_6$ alkyl;

$R_6$ is selected from the group consisting of —OH, $C_1-C_6$ alkoxy, —OC(O)—$C_1-C_6$ alkyl, and —OC(O)phenyl; and $R_7$ is H or $C_1-C_6$ alkyl;

or in other embodiments, the variables set forth in formula (I) are defined as follows:

$R_b$ is selected from the group consisting of H, halogen, hydroxyl, cyano and $C_1-C_6$ alkyl (e.g., H);

$R_1$ is H or $C_1-C_6$ alkyl;

$R_2$ is H or $C_1-C_6$ alkyl;

$R_3$ is selected from the group consisting of H, $C_1-C_6$ alkyl and a nitrogen protecting group;

$R_4$ and $R_5$ are each independently selected from the group consisting of H, $C_1-C_6$ alkyl, X, and —$C_1-C_6$ alkylene-X, wherein X is selected from the group consisting of:
  (i) $C_3-C_6$ cycloalkyl;
  (ii) heteroaryl including from 5 to 6 ring atoms wherein 1, 2, or 3 of the ring atoms are independently selected from the group consisting of N, NH, N(C1-C3 alkyl), O, and S;

(iii) heterocyclyl including from 3 to 6 ring atoms wherein 1, 2, or 3 of the ring atoms are independently selected from the group consisting of N, NH, N(C1-C3 alkyl), O, and S; and (iv) phenyl;

wherein $C_3$-$C_6$ cycloalkyl and heterocyclyl are each optionally substituted with from 1-3 substituents independently selected from the group consisting of halogen, cyano, oxo, $C_1$-$C_6$ alkyl, hydroxyl, $C_1$-$C_6$ alkoxy, and —N(R')R', wherein R' is independently selected for each occurrence from H and $C_1$-$C_6$ alkyl; and heteroaryl and phenyl are each optionally substituted with from 1-3 substituents independently selected from the group consisting of halogen, cyano, $C_1$-$C_6$ alkyl, hydroxyl, $C_1$-$C_6$ alkoxy, and —N(R')R';

or $R_4$ and $R_5$ together with the nitrogen to which they are attached form:

heterocyclyl including from 4 to 6 ring atoms; wherein the heterocyclyl includes not more than two ring heteroatoms (including the nitrogen atom attached to $R_4$ and $R_5$), and the second ring heteroatom, when present, is independently selected from the group consisting of N, NH, N(C1-C3 alkyl), O, and S; and wherein the heterocyclyl is optionally substituted with from 1-3 substituents independently selected from the group consisting of halogen, cyano, oxo, $C_1$-$C_6$ alkyl, hydroxyl, $C_1$-$C_6$ alkoxy, and —N(R')R'; or heteroaryl including from 5 to 6 ring atoms; wherein the heteroaryl includes not more than four ring heteroatoms (including the nitrogen atom attached to $R_4$ and $R_5$), and each additional ring heteroatom, when present, is independently selected from the group consisting of N, NH, N(C1-C3 alkyl), O, and S; and wherein the heteroaryl is optionally substituted with from 1-3 substituents independently selected from the group consisting of halogen, cyano, $C_1$-$C_6$ alkyl, hydroxyl, $C_1$-$C_6$ alkoxy, and —N(R')R';

$R_6$ is selected from the group consisting of —OH, $C_1$-$C_6$ alkoxy, —OC(O)—$C_1$-$C_6$ alkyl, —OC(O)phenyl, and —N(R')R'; and $R_7$ is H or $C_1$-$C_6$ alkyl.

In some embodiments, $R_1$ is H. In other embodiments, $R_1$ is $C_1$-$C_6$ alkyl, e.g., $CH_3$.

In some embodiments, $R_2$ is H. In other embodiments, $R_2$ is $C_1$-$C_6$ alkyl, e.g., $CH_3$.

In some embodiments, $R_3$ is H.

In some embodiments, $R_3$ is a nitrogen protecting group. In some embodiments, $R_3$ has formula —C(O)OR$_{31}$, wherein R$_{31}$ is selected from the group consisting of: $C_1$-$C_6$ alkyl; $C_1$-$C_6$ haloalkyl; $C_2$-$C_6$ alkenyl; $C_2$-$C_6$ alkynyl; $C_3$-$C_{10}$ cycloalkyl, wherein the $C_3$-$C_{10}$ cycloalkyl is optionally substituted with from 1-3 independently selected $C_1$-$C_3$ alkyl; —CH$_2$—$C_3$-$C_{10}$ cycloalkyl wherein the $C_3$-$C_{10}$ cycloalkyl is optionally substituted with from 1-3 independently selected $C_1$-$C_3$ alkyl; —CH$_2$-phenyl, wherein the phenyl is optionally substituted with from 1-2 substituents independently selected from $C_1$-$C_3$ alkyl, $C_1$-$C_3$ haloalkyl, $C_1$-$C_3$ alkoxy, $C_1$-$C_3$ haloalkoxy, nitro, halo, SO$_2$Me, cyano, and —OC(O)CH$_3$; and —CH$_2$-pyridyl. In certain embodiments, $R_3$, is $C_1$-$C_6$ alkyl (e.g., tert-butyl). In other embodiments, $R_3$ has formula —C(O)R$_{32}$, wherein R$_{32}$ is selected from the group consisting of: H; $C_1$-$C_6$ alkyl; $C_1$-$C_6$ haloalkyl; phenyl, wherein the phenyl is optionally substituted with from 1-2 substituents independently selected from $C_1$-$C_3$ alkyl; $C_1$-$C_3$ haloalkyl; $C_1$-$C_3$ alkoxy; $C_1$-$C_3$ haloalkoxy; nitro; halo; SO$_2$Me, cyano; and —OC(O)CH$_3$; and pyridyl. In certain embodiments, R$_{32}$ is $C_1$-$C_6$ alkyl (e.g., —CH$_3$ or iso-propyl).

In some embodiments, $R_4$ and $R_5$ are each independently selected from the group consisting of H, $C_1$-$C_6$ alkyl, X, and —$C_1$-$C_6$ alkylene-X. In certain embodiments, $R_4$ and $R_5$ are each independently selected from the group consisting of H and $C_1$-$C_6$ alkyl. In other embodiments, $R_4$ and $R_5$ are each independently selected from the group consisting of H and —$C_1$-$C_6$ alkylene-X. In certain embodiments, $R_4$ and $R_5$ are H. In other embodiments, one of $R_4$ and $R_5$ is H, and the other is —$C_1$-$C_6$ alkylene-X. In certain of these embodiments, the compounds can include one or both (e.g., both) of the following features: (i) —$C_1$-$C_6$ alkylene-X is —CH$_2$—X; and (ii) X is phenyl or heteroaryl including from 5 to 6 ring atoms wherein 1, 2, or 3 of the ring atoms are independently selected from the group consisting of N, NH, N(C1-C3 alkyl), O, and S; each optionally substituted with from 1-3 substituents independently selected from the group consisting of halogen, cyano, $C_1$-$C_6$ alkyl, hydroxyl, $C_1$-$C_6$ alkoxy, and —N(R')R'.

In other embodiments, $R_4$ and $R_5$ taken together form a heterocyclic or heteroaryl ring as defined previously and anywhere herein. In certain embodiments, $R_4$ and $R_5$ taken together form a heterocyclic ring, e.g., a ring selected from the group consisting of azetidinyl, pyrrolidinyl, pyrazolidinyl, isooxazolidinyl, imidazolidinyl, oxazolidinyl, thiazolidinyl, and isothiazolidinyl. In a particular embodiment, $R_4$ and $R_5$ taken together form a pyrrolidinyl ring. In certain embodiments, $R_4$ and $R_5$ taken together form a heteroaryl ring, e.g., a ring selected from the group consisting of imidazolyl, pyrazolyl, oxazolyl, isoxazolyl, thiazolyl, pyridinyl, diazinyl, oxazinyl, and thiazinyl.

In some embodiments, $R_1$ is H; $R_2$ is H; $R_3$ is H; and $R_4$ and $R_5$ taken together form a pyrrolidine ring. In some embodiments, $R_1$ is H; $R_2$ is H; $R_3$ is H; and $R_4$ and $R_5$ are H. In some embodiments, $R_1$ is H or CH$_3$; $R_2$ is H or CH$_3$; $R_3$ is H; and $R_4$ and $R_5$ taken together form a pyrrolidinyl ring. In some embodiments, $R_1$ is H or CH$_3$; $R_2$ is H or CH$_3$; $R_3$ is H; and $R_4$ and $R_5$ are H. In some embodiments, $R_1$ is H or CH$_3$; $R_2$ is H or CH$_3$; $R_3$ is H; and one of $R_4$ and $R_5$ is H, and the other is —CH$_2$—X, wherein X is phenyl or heteroaryl including from 5 to 6 ring atoms wherein 1, 2, or 3 of the ring atoms are independently selected from the group consisting of N, NH, N(C1-C3 alkyl), O, and S; each optionally substituted with from 1-3 substituents independently selected from the group consisting of halogen, cyano, $C_1$-$C_6$ alkyl, hydroxyl, $C_1$-$C_6$ alkoxy, and —N(R')R'. In some embodiments, $R_1$ is H or CH$_3$; $R_2$ is H or CH$_3$; $R_3$ is nitrogen protecting group (e.g., —C(O)OR$_{31}$ or —C(O)R$_{32}$); and $R_4$ and $R_5$ taken together form a pyrrolidinyl ring. In some embodiments, $R_1$ is H or CH$_3$; $R_2$ is H or CH$_3$; $R_3$ is nitrogen protecting group (e.g., —C(O)OR$_{31}$ or —C(O)R$_{32}$); and $R_4$ and $R_5$ are H. In some embodiments, $R_1$ is H or CH$_3$; $R_2$ is H or CH$_3$; $R_3$ is nitrogen protecting group (e.g., —C(O)OR$_{31}$ or —C(O)R$_{32}$); and one of $R_4$ and $R_5$ is H, and the other is —CH$_2$—X, wherein X is phenyl or heteroaryl including from 5 to 6 ring atoms wherein 1, 2, or 3 of the ring atoms are independently selected from the group consisting of N, NH, N(C1-C3 alkyl), O, and S; each optionally substituted with from 1-3 substituents independently selected from the group consisting of halogen, cyano, $C_1$-$C_6$ alkyl, hydroxyl, $C_1$-$C_6$ alkoxy, and —N(R')R'.

In some embodiments (including any of the foregoing embodiments described above), $R_6$ is selected from the group consisting of —OH, $C_1$-$C_6$ alkoxy, —OC(O)—$C_1$-$C_6$ alkyl, and —OC(O)phenyl. In certain embodiments (including any of the foregoing embodiments described above), $R_6$ is —OH. In other embodiments (including any of the foregoing embodiments described above), $R_6$ is —NH$_2$. In some embodiments (including any of the foregoing embodiments described above), $R_7$ is $C_1$-$C_6$ alkyl, e.g., CH$_3$. In some embodiments (including any of the foregoing embodiments described above), $R_6$ is —OH or —NH$_2$, and $R_7$ is $C_1$-$C_6$ alkyl, e.g., CH$_3$. In some embodiments (including any of the foregoing embodiments described above), $R_b$ is H.

In some embodiments, the compound is selected from the compounds delineated in Table 1 and/or the Examples. In certain embodiments, a disclosed compound includes one having the formula:

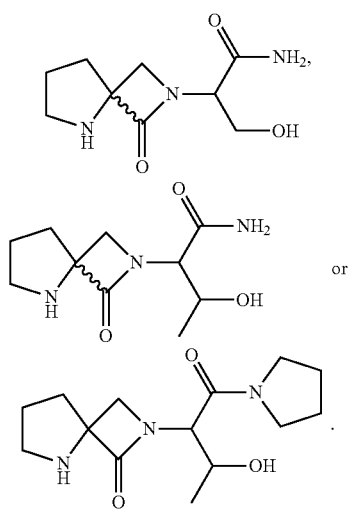

The compounds of the present disclosure and formulations thereof may have a plurality of chiral centers. Each chiral center may be independently R, S, or any mixture of R and S. For example, in some embodiments, a chiral center may have an R:S ratio of between about 100:0 and about 50:50, between about 100:0 and about 75:25, between about 100:0 and about 85:15, between about 100:0 and about 90:10, between about 100:0 and about 95:5, between about 100:0 and about 98:2, between about 100:0 and about 99:1, between about 0:100 and 50:50, between about 0:100 and about 25:75, between about 0:100 and about 15:85, between about 0:100 and about 10:90, between about 0:100 and about 5:95, between about 0:100 and about 2:98, between about 0:100 and about 1:99, between about 75:25 and 25:75, and about 50:50. Formulations of the disclosed compounds comprising a greater ratio of one or more isomers (i.e., R and/or S) may possess enhanced therapeutic characteristic relative to racemic formulations of a disclosed compounds or mixture of compounds. In some instances, chemical formulas contain the descriptor "—(R)—" or "—(S)—" that is further attached to solid wedge or dashed wedge. This descriptor is intended to show a methine carbon (CH) that is attached to three other substituents and has either the indicated R or S configuration (see, e.g., Table 1).

Disclosed compounds may provide for efficient cation channel opening at the NMDA receptor, e.g. may bind or associate with the glutamate site of the NMDA receptor to assist in opening the cation channel. The disclosed compounds may be used to regulate (turn on or turn off) the NMDA receptor through action as an agonist.

The compounds as described herein may be glycine site NMDA receptor partial agonists. A partial agonist as used in this context will be understood to mean that at a low concentration, the analog acts as an agonist and at a high concentration, the analog acts as an antagonist. Glycine binding is not inhibited by glutamate or by competitive inhibitors of glutamate, and also does not bind at the same site as glutamate on the NMDA receptor. A second and separate binding site for glycine exists at the NMDA receptor. The ligand-gated ion channel of the NMDA receptor is, thus, under the control of at least these two distinct allosteric sites. Disclosed compounds may be capable of binding or associating with the glycine binding site of the NMDA receptor. In some embodiments, disclosed compounds may possess a potency that is 10-fold or greater than the activity of existing NMDA receptor glycine site partial agonists.

The disclosed compounds may exhibit a high therapeutic index. The therapeutic index, as used herein, refers to the ratio of the dose that produces a toxicity in 50% of the population (i.e., $TD_{50}$) to the minimum effective dose for 50% of the population (i.e., $ED_{50}$). Thus, the therapeutic index=$(TD_{50})$:$(ED_{50})$. In some embodiments, a disclosed compound may have a therapeutic index of at least about 10:1, at least about 50:1, at least about 100:1, at least about 200:1, at least about 500:1, or at least about 1000:1.

Compositions

In other aspects, formulations and compositions comprising the disclosed compounds and optionally a pharmaceutically acceptable excipient are provided. In some embodiments, a contemplated formulation comprises a racemic mixture of one or more of the disclosed compounds.

Contemplated formulations may be prepared in any of a variety of forms for use. By way of example, and not limitation, the compounds may be prepared in a formulation suitable for oral administration, subcutaneous injection, or other methods for administering an active agent to an animal known in the pharmaceutical arts.

Amounts of a disclosed compound as described herein in a formulation may vary according to factors such as the disease state, age, sex, and weight of the individual. Dosage regimens may be adjusted to provide the optimum therapeutic response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier.

The specification for the dosage unit forms of the invention are dictated by and directly dependent on (a) the unique characteristics of the compound selected and the particular therapeutic effect to be achieved, and (b) the limitations inherent in the art of compounding such an active compound for the treatment of sensitivity in individuals.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof.

The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin.

The compounds can be administered in a time release formulation, for example in a composition which includes a slow release polymer. The compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are generally known to those skilled in the art.

Sterile injectable solutions can be prepared by incorporating the compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

In accordance with an alternative aspect of the invention, a compound may be formulated with one or more additional compounds that enhance the solubility of the compound.

Methods

Methods for treating a condition in a patient in need thereof by administering a therapeutically effective dose of a compound described herein are provided. In some embodiments, the condition may be a mental condition. For example, a mental illness may be treated. In another aspect, a nervous system condition may be treated. For example, a condition that affects the central nervous system, the peripheral nervous system, and/or the eye may be treated. In some embodiments, neurodegenerative diseases may be treated.

In some embodiments, the methods include administering a compound to treat patients suffering from autism, anxiety, depression, bipolar disorder, attention deficit disorder, attention deficit hyperactivity disorder (ADHD), schizophrenia, a psychotic disorder, a psychotic symptom, social withdrawal, obsessive-compulsive disorder (OCD), phobia, post-traumatic stress syndrome, a behavior disorder, an impulse control disorder, a substance abuse disorder (e.g., a withdrawal symptom, opiate addiction, nicotine addiction, and ethanol addition), a sleep disorder, a memory disorder (e.g., a deficit, loss, or reduced ability to make new memories), a learning disorder, urinary incontinence, multiple system atrophy, progressive supra-nuclear palsy, Friedrich's ataxia, Down's syndrome, fragile X syndrome, tuberous sclerosis, olivio-ponto-cerebellar atrophy, cerebral palsy, drug-induced optic neuritis, ischemic retinopathy, diabetic retinopathy, glaucoma, dementia, AIDS dementia, Alzheimer's disease, Huntington's chorea, spasticity, myoclonus, muscle spasm, Tourette's syndrome, epilepsy, cerebral ischemia, stroke, a brain tumor, traumatic brain injury, cardiac arrest, myelopathy, spinal cord injury, peripheral neuropathy, acute neuropathic pain, and chronic neuropathic pain.

In some embodiments, methods of treating a memory disorder associated with aging, schizophrenia, special learning disorders, seizures, post-stroke convulsions, brain ischemia, hypoglycemia, cardiac arrest, epilepsy, migraine, AIDS dementia, Huntington's chorea, Parkinson's disease, early stage Alzheimer's disease, and Alzheimer's disease are contemplated.

In certain embodiments, methods for treating schizophrenia are provided. For example, paranoid type schizophrenia, disorganized type schizophrenia (i.e., hebephrenic schizophrenia), catatonic type schizophrenia, undifferentiated type schizophrenia, residual type schizophrenia, post-schizophrenic depression, and simple schizophrenia may be treated using the methods and compositions contemplated herein. Psychotic disorders such as schizoaffective disorders, delusional disorders, brief psychotic disorders, shared psychotic disorders, and psychotic disorders with delusions or hallucinations may also be treated using the compositions contemplated herein.

Paranoid schizophrenia may be characterized where delusions or auditory hallucinations are present, but thought disorder, disorganized behavior, or affective flattening are not. Delusions may be persecutory and/or grandiose, but in addition to these, other themes such as jealousy, religiosity, or somatization may also be present. Disorganized type schizophrenia may be characterized where thought disorder and flat affect are present together. Catatonic type schizophrenia may be characterized where the patient may be almost immobile or exhibit agitated, purposeless movement. Symptoms can include catatonic stupor and waxy flexibility. Undifferentiated type schizophrenia may be characterized where psychotic symptoms are present but the criteria for paranoid, disorganized, or catatonic types have not been met. Residual type schizophrenia may be characterized where positive symptoms are present at a low intensity only. Post-schizophrenic depression may be characterized where a depressive episode arises in the aftermath of a schizophrenic illness where some low-level schizophrenic symptoms may still be present. Simple schizophrenia may be characterized by insidious and progressive development of prominent negative symptoms with no history of psychotic episodes.

In some embodiments, methods are provided for treating psychotic symptoms that may be present in other mental disorders, including, but not limited to, bipolar disorder, borderline personality disorder, drug intoxication, and drug-induced psychosis. In another embodiment, methods for treating delusions (e.g., "non-bizarre") that may be present in, for example, delusional disorder are provided.

Also provided are methods for treating social withdrawal in conditions including, but not limited to, social anxiety disorder, avoidant personality disorder, and schizotypal personality disorder.

In some embodiments, methods are provided for treating neuropathic pain. The neuropathic pain may be acute or chronic. In some cases, the neuropathic pain may be associated with a condition such as herpes, HIV, traumatic nerve injury, stroke, post-ischemia, fibromyalgia, reflex sympathetic dystrophy, complex regional pain syndrome, spinal cord injury, sciatica, phantom limb pain, diabetic neuropathy, and cancer chemotherapeutic-induced neuropathic pain. Methods for enhancing pain relief and for providing analgesia to a patient are also contemplated.

Further contemplated methods include a method of treating autism and/or an autism spectrum disorder in a patient need thereof, comprising administering an effective amount of a compound to the patient. In an embodiment, a method for reducing the symptoms of autism in a patient in need thereof is contemplated, comprising administering an effective amount of a disclosed compound to the patient. For example, upon administration, the compound may decrease the incidence of one or more symptoms of autism such as eye contact avoidance, failure to socialize, attention deficit, poor mood, hyperactivity, abnormal sound sensitivity, inappropriate speech, disrupted sleep, and perseveration. Such decreased incidence may be measured relative to the incidence in the untreated individual or an untreated individual(s).

Also provided herein is a method of modulating an autism target gene expression in a cell comprising contacting a cell with an effective amount of a compound described herein. The autism gene expression may be for example, selected from ABAT, APOE, CHRNA4, GABRA5, GFAP, GRIN2A, PDYN, and PENK. In another embodiment, a method of modulating synaptic plasticity in a patient suffering from a synaptic plasticity related disorder is provided, comprising administering to the patient an effective amount of a compound.

In another embodiment, a method of treating Alzheimer's disease, or e.g., treatment of memory loss that e.g., accompanies early stage Alzheimer's disease, in a patient in need thereof is provided, comprising administering a compound. Also provided herein is a method of modulating an Alzheimer's amyloid protein (e.g., beta amyloid peptide, e.g. the isoform $A\beta_{1-42}$), in-vitro or in-vivo (e.g. in a cell) comprising contacting the protein with an effective amount of a compound is disclosed. For example, in some embodiments, a compound may block the ability of such amyloid protein to inhibit long-term potentiation in hippocampal slices as well as apoptotic neuronal cell death. In some embodiments, a disclosed compound may provide neuroprotective properties to a Alzheimer's patient in need thereof, for example, may provide a therapeutic effect on later stage Alzheimer's-associated neuronal cell death.

In a further embodiment, a method of treating depression comprising administering a compound described herein is provided. In some embodiments, the treatment may relieve depression or a symptom of depression without affecting behavior or motor coordination and without inducing or promoting seizure activity. Exemplary depression conditions that are expected to be treated according to this aspect of the invention include, but are not limited to, major depressive disorder, dysthymic disorder, psychotic depression, postpartum depression, premenstrual syndrome, premenstrual dysphoric disorder, seasonal affective disorder (SAD), bipolar disorder (or manic depressive disorder), mood disorder, and depressions caused by chronic medical conditions such as cancer or chronic pain, chemotherapy, chronic stress, and post traumatic stress disorders. In addition, patients suffering from any form of depression often experience anxiety. Various symptoms associated with anxiety include fear, panic, heart palpitations, shortness of breath, fatigue, nausea, and headaches among others. Anxiety or any of the symptoms thereof may be treated by administering a compound as described herein.

Also provided herein are methods of treating a condition in treatment-resistant patients, e.g., patients suffering from a mental or central nervous system condition that does not, and/or has not, responded to adequate courses of at least one, or at least two, other compounds or therapeutics. For example, provided herein is a method of treating depression in a treatment resistant patient, comprising a) optionally identifying the patient as treatment resistant and b) administering an effective dose of a compound to said patient.

In some embodiments, a compound described herein may be used for acute care of a patient. For example, a compound may be administered to a patient to treat a particular episode (e.g., a severe episode) of a condition contemplated herein.

Also contemplated herein are combination therapies comprising a compound in combination with one or more other active agents. For example, a compound may be combined with one or more antidepressants, such as tricyclic antidepressants, MAO-I's, SSRI's, and double and triple uptake inhibitors and/or anxiolytic drugs. Exemplary drugs that may be used in combination with a compound include Anafranil, Adapin, Aventyl, Elavil, Norpramin, Pamelor, Pertofrane, Sinequan, Surmontil, Tofranil, Vivactil, Parnate, Nardil, Marplan, Celexa, Lexapro, Luvox, Paxil, Prozac, Zoloft, Wellbutrin, Effexor, Remeron, Cymbalta, Desyrel (trazodone), and Ludiomill. In another example, a compound may be combined with an antipsychotic medication. Non-limiting examples of antipsychotics include butyrophenones, phenothiazines, thioxanthenes, clozapine, olanzapine, risperidone, quetiapine, ziprasidone, amisulpride, asenapine, paliperidone, iloperidone, zotepine, sertindole, lurasidone, and aripiprazole. It should be understood that combinations of a compound and one or more of the above therapeutics may be used for treatment of any suitable condition and are not limited to use as antidepressants or antipsychotics.

EXAMPLES

The following examples are provided for illustrative purposes only, and are not intended to limit the scope of the disclosure.

Table 1 below shows some exemplary compounds of the disclosure and provides physiochemical characteristics of the compounds.

TABLE 1

| Compound | Structure | Molecular Weight (Da) | cLogP | tPSA |
|---|---|---|---|---|
| Compound X | 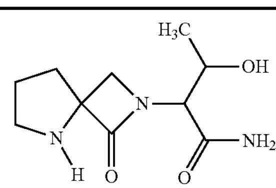 | 227 | −1.94 | 96.7 |

TABLE 1-continued

| Compound | Structure | Molecular Weight (Da) | cLogP | tPSA |
|---|---|---|---|---|
| Compound Y | 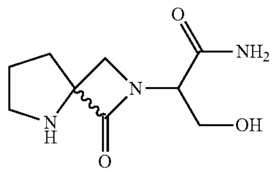 [SMILES: NC(=O)C(CO)N1CC2(CCCN2)C1=O] | 213 | −2.36 | 96.7 |
| Compound Z | 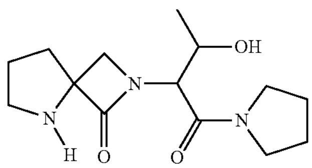 [SMILES: CC(O)C(C(=O)N1CCCC1)N1CC2(CCCN2)C1=O] | 281 | −1.09 | 72.9 |
| 2S-19 | 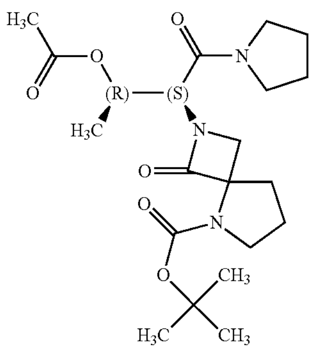 | 423.5032 | 0.634639 | 96.46 |
| 2S-20 | 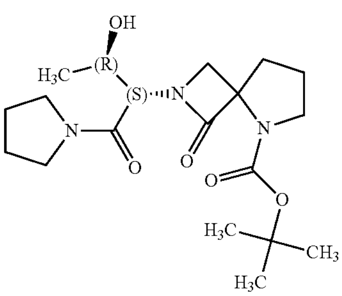 | 381.4665 | 0.193514 | 90.39 |
| 2S-21 | 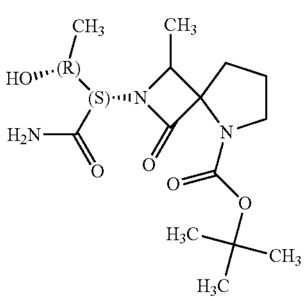 | 341.4027 | −0.243061 | 113.17 |

TABLE 1-continued

| Compound | Structure | Molecular Weight (Da) | cLogP | tPSA |
|---|---|---|---|---|
| 2S-24 | 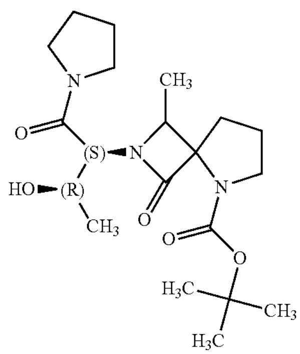 | 395.4931 | 0.610089 | 90.39 |
| 2S-27 | 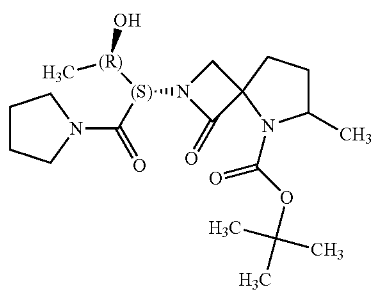 | 395.4931 | 0.610089 | 90.39 |
| 2S-30 | 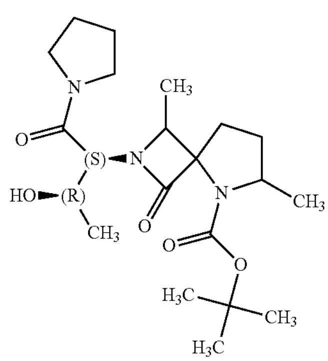 | 409.5197 | 1.02666 | 90.39 |
| 2S-8 | 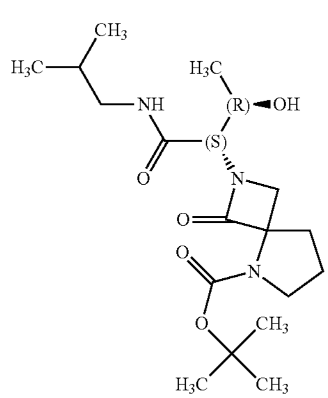 | 383.4824 | 0.808343 | 99.18 |

TABLE 1-continued

| Compound | Structure | Molecular Weight (Da) | cLogP | tPSA |
|---|---|---|---|---|
| 2S-9 | 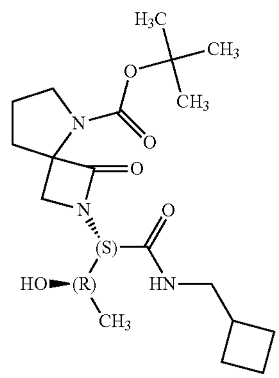 | 395.4931 | 0.789186 | 99.18 |
| 2S-FNL-10 | 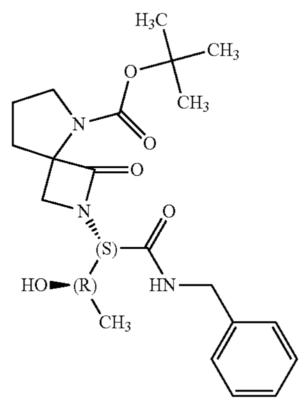 | 417.4986 | 1.28851 | 99.18 |
| 2S-FNL-11 | 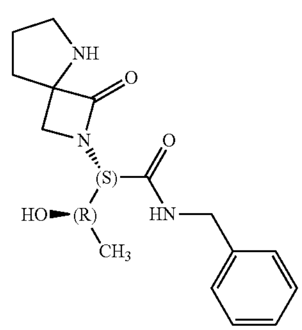 | 317.3828 | 0.00532027 | 81.67 |
| 2S-FNL-12 | 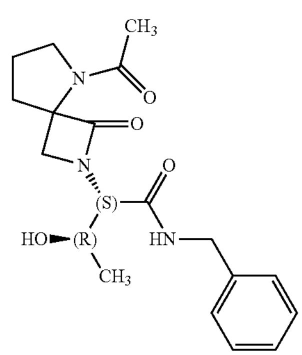 | 359.4195 | −0.384737 | 89.95 |

TABLE 1-continued

| Compound | Structure | Molecular Weight (Da) | cLogP | tPSA |
|---|---|---|---|---|
| 2S-FNL-13 | 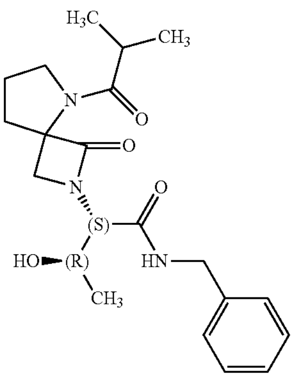 | 387.4727 | 0.858785 | 89.95 |
| 2S-FNL-14 | 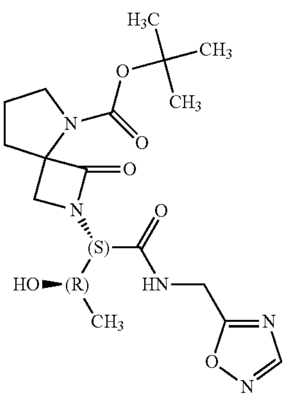 | 409.4369 | −0.960294 | 138.1 |
| 2S-FNL-15 | 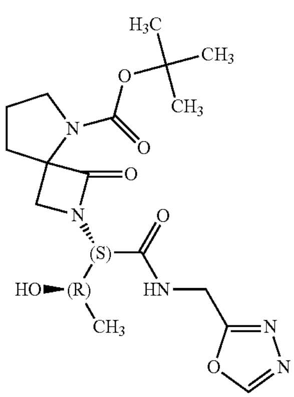 | 409.4369 | −1.65688 | 138.1 |
| 2S-FNL-16 | 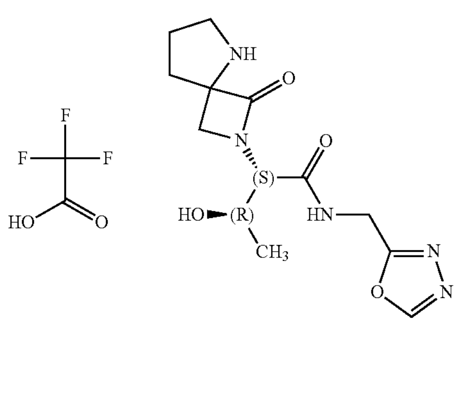 | 423.3444 | −2.94007 | 120.59 |

TABLE 1-continued

| Compound | Structure | Molecular Weight (Da) | cLogP | tPSA |
|---|---|---|---|---|
| 2S-FNL-17 | 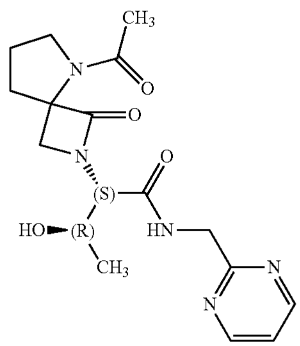 | 361.3956 | −1.88186 | 115.73 |
| 2S-FNL-18 | 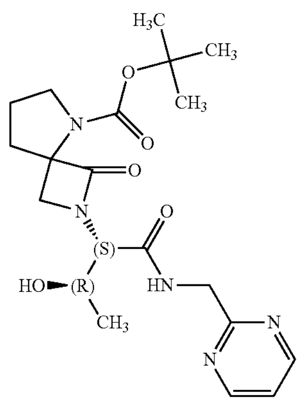 | 419.4748 | −0.35934 | 124.96 |
| 2S-FNL-19 | 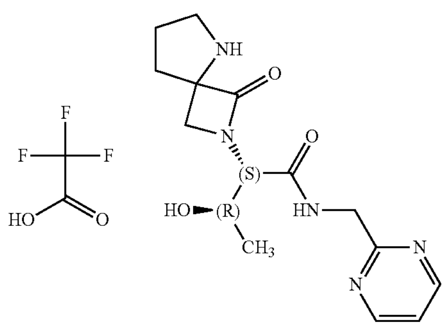 | 433.3823 | −1.6029 | 107.45 |
| 2S-FNL-2 | 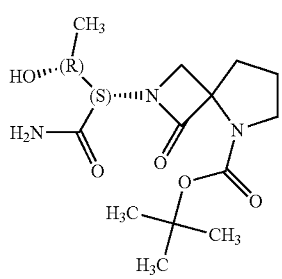 | 327.3761 | −0.659636 | 113.17 |

TABLE 1-continued

| Compound | Structure | Molecular Weight (Da) | cLogP | tPSA |
|---|---|---|---|---|
| 2S-FNL-20 | 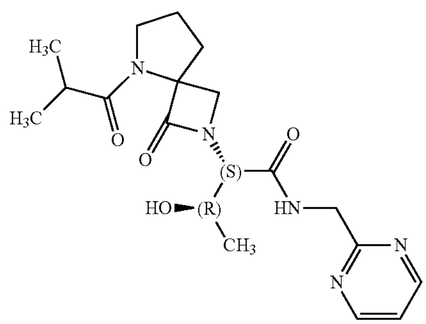 | 389.4488 | −0.696233 | 115.73 |
| 2S-FNL-21 | 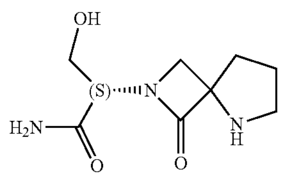 | 213.2337 | −2.3594 | 95.66 |
| 2S-FNL-22, 2S-16 | 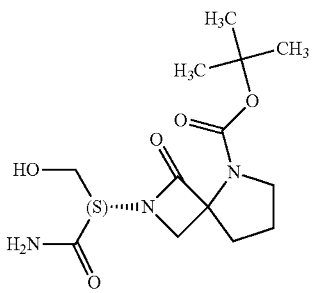 | 313.3495 | −1.07621 | 113.17 |
| 2S-FNL-23 | 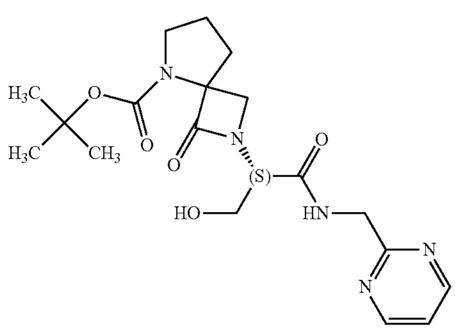 | 405.4482 | −0.769835 | 124.96 |
| 2S-FNL-24 | 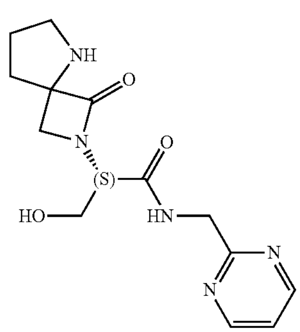 | 305.3324 | −2.01339 | 107.45 |

TABLE 1-continued

| Compound | Structure | Molecular Weight (Da) | cLogP | tPSA |
|---|---|---|---|---|
| 2S-FNL-25 | 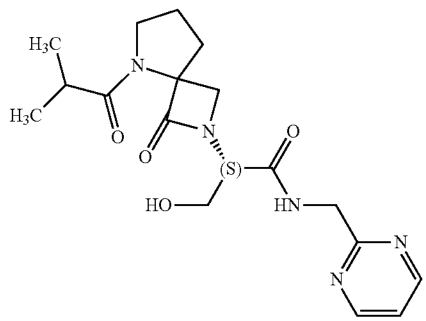 | 375.4222 | −1.10673 | 115.73 |
| 2S-FNL-26 | 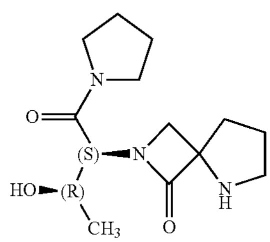 | 281.3507 | −1.08968 | 72.88 |
| 2S-FNL-27 | 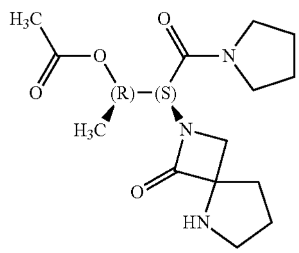 | 359.848 | −0.648554 | 78.95 |
| 2S-FNL-28 | 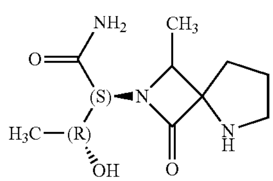 | 241.2869 | −1.52625 | 95.66 |
| 2S-FNL-29 | 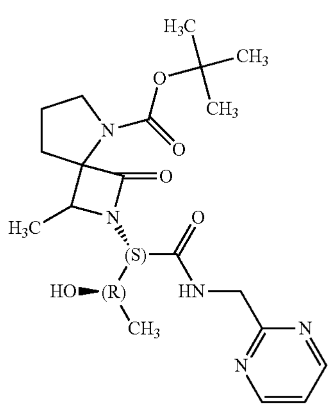 | 433.5013 | 0.0511544 | 124.96 |
| 2S-FNL-3 | 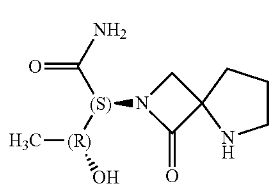 | 227.2603 | −1.94283 | 95.66 |

TABLE 1-continued

| Compound | Structure | Molecular Weight (Da) | cLogP | tPSA |
|---|---|---|---|---|
| 2S-FNL-30 | 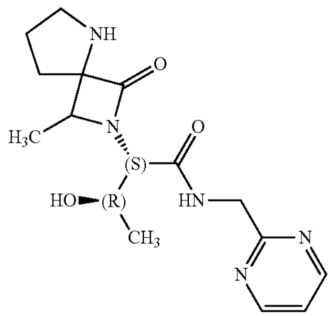 | 333.3855 | −1.1924 | 107.45 |
| 2S-FNL-31 | 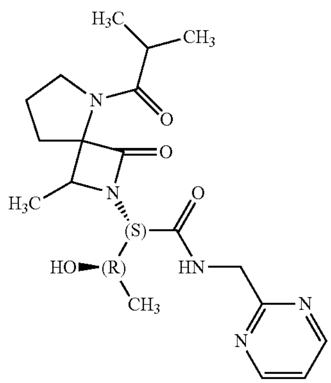 | 403.4754 | −0.285738 | 115.73 |
| 2S-FNL-32 | 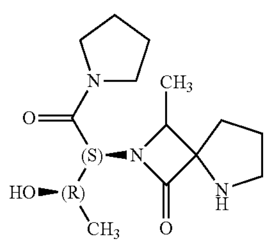 | 295.3773 | −0.673104 | 72.88 |
| 2S-FNL-33 | 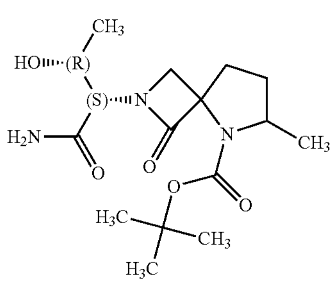 | 341.4027 | −0.243061 | 113.17 |
| 2S-FNL-34 | 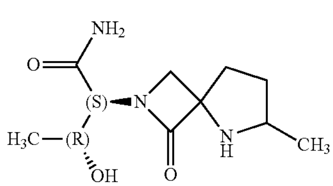 | 241.2869 | −1.52625 | 95.66 |

TABLE 1-continued

| Compound | Structure | Molecular Weight (Da) | cLogP | tPSA |
|---|---|---|---|---|
| 2S-FNL-35 | 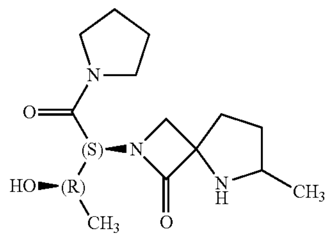 | 295.3773 | −0.673104 | 72.88 |
| 2S-FNL-36 | 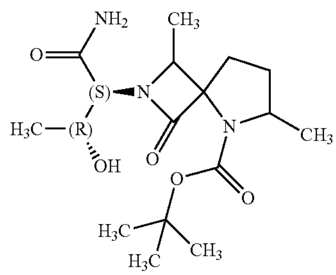 | 355.4293 | 0.173514 | 113.17 |
| 2S-FNL-37 | 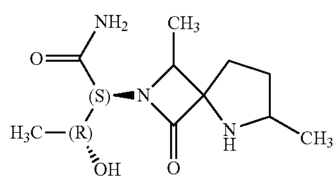 | 255.3134 | −1.10968 | 95.66 |
| 2S-FNL-38 | 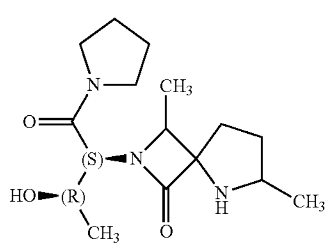 | 309.4039 | −0.256529 | 72.88 |
| 2S-FNL-4 | 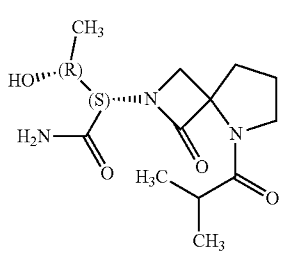 | 297.3501 | −1.08936 | 103.94 |

TABLE 1-continued

| Compound | Structure | Molecular Weight (Da) | cLogP | tPSA |
|---|---|---|---|---|
| 2S-FNL-5 | 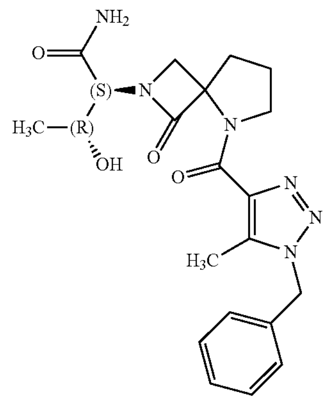 | 426.4689 | −0.121843 | 134.65 |
| 2S-FNL-6 | 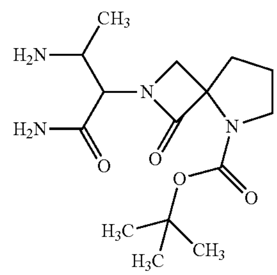 [SMILES: CC(N)C(C(N)=O)N1CC2(CCCN2C(=O)OC(C)(C)C)C1=O] | 326.3913 | −0.766518 | 118.96 |
| 2S-FNL-7 | 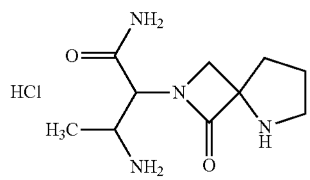 [SMILES: Cl ; CC(N)C(C(N)=O)N1CC2(CCCN2)C1=O] | 262.736 | −2.04971 | 101.45 |
| 2S-FNL-8 | 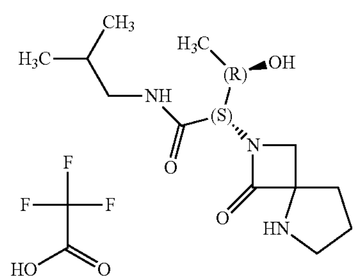 | 397.3899 | −0.47485 | 81.67 |
| 2S-FNL-9 | 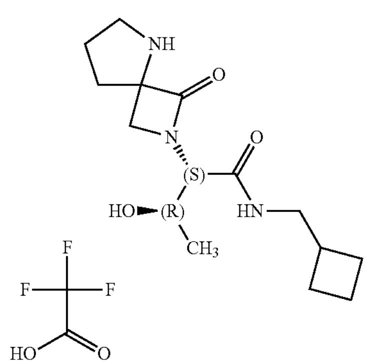 | 409.4006 | −0.494007 | 81.67 |

Example 1

Synthesis of Compound X

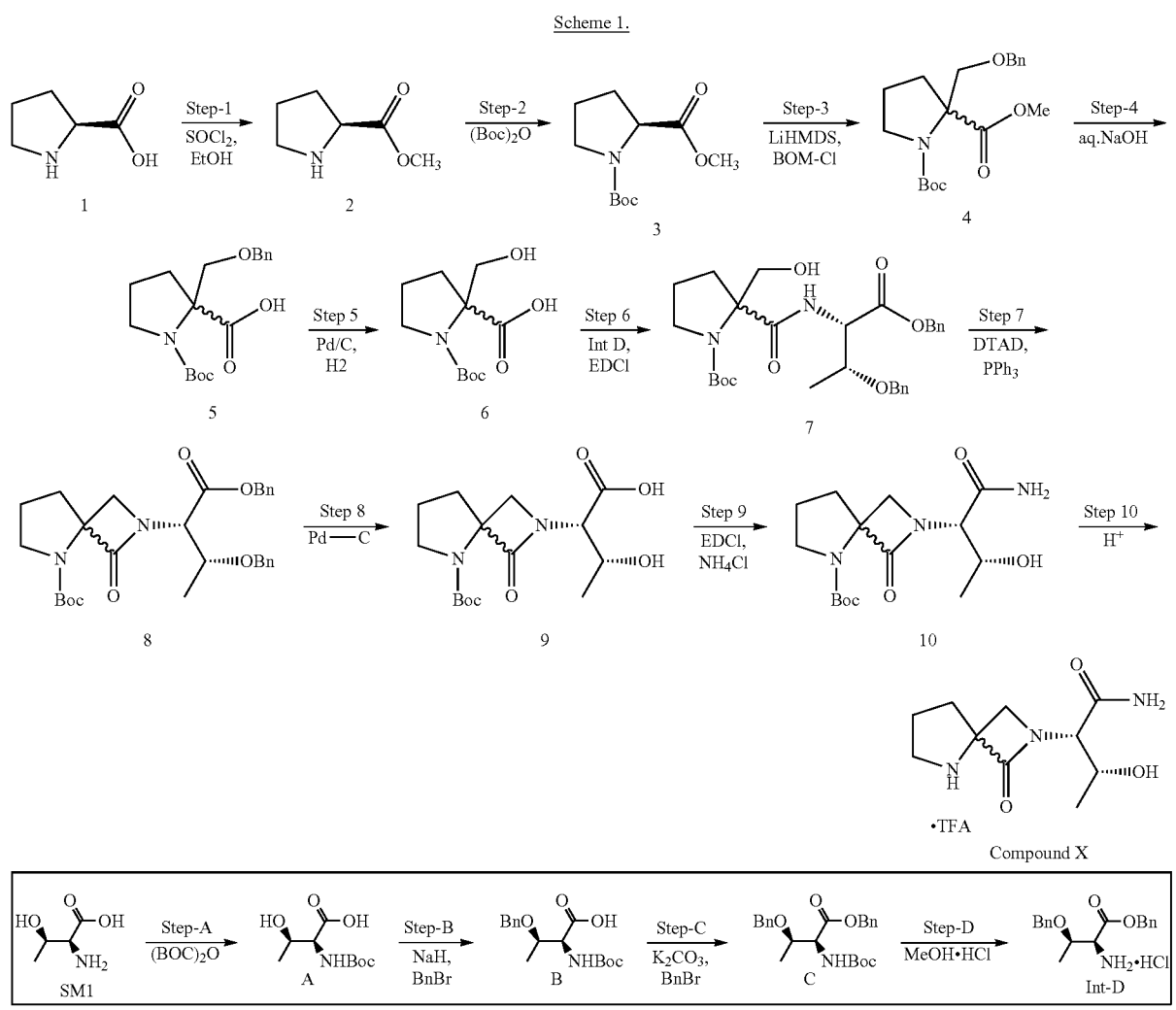

Scheme 1.

Synthesis of (2S, 3R)-2-((tert-butoxycarbonyl) amino)-3-hydroxybutanoic acid (A)

To a stirred solution of L-threonine (SM1) (100 g, 0.84 mol) in 1,4-dioxane (500 mL) and water (800 mL) was added $Na_2CO_3$ (178 g, 1.67 mol) and stirred at RT for 30 min. The reaction mixture was cooled to 0° C., Boc-anhydride (219.6 g, 1.007 mol) was added drop wise and stirring was continued for 16 h. After consumption of the starting material (by TLC), the reaction mixture was concentrated under reduced pressure and obtained residue was neutralized using 1N HCl (pH~4). The aqueous layer was extracted with EtOAc (2×250 mL). The separated organic extracts were washed with brine, dried over anhydrous $Na_2SO_4$, filtered and concentrated under reduced pressure to afford A (160 g, 87%).

$^1$H-NMR: (500 MHz, DMSO-$d_6$): δ 6.30 (d, 1H), 4.07-4.01 (m, 1H), 3.90 (d, 1H), 1.99 (s, 1H), 1.42 (s, 9H), 1.09 (d, 3H).

LCMS (m/z): 218.1 [M$^+$−1]

Synthesis of (2S, 3R)-3-(benzyloxy)-2-((tert-butoxycarbonyl) amino) butanoic acid (B)

To a stirred solution of A (100 g, 0.45 mol) in DMF (600 mL) was added 60% NaH (36.5 g, 0.91 mol) portion wise at −20° C. under $N_2$ atmosphere and stirred for 2 h. To this was added benzyl bromide (66.8 mL, 0.55 mol) drop wise and the reaction mixture was stirred at RT for 12 h. After consumption of the starting material (by TLC), the reaction mixture was quenched with ice cold water and washed with diethyl ether (2×250 mL). The separated aqueous layer was acidified using 1N HCl and extracted with EtOAc (2×250 mL). The combined organic layers were dried over anhydrous $Na_2SO_4$ and concentrated under reduced pressure to afford B (100 g, 71%).

Synthesis of (2S, 3R)-benzyl 3-(benzyloxy)-2-((tert-butoxycarbonyl) amino) butanoate (C)

To a stirred solution of B (100 g, 0.32 mol) in DMF (400 mL) was added $K_2CO_3$ (111.6 g, 0.81 mol) under $N_2$ atmosphere and stirred for 30 min. To this was added benzyl bromide (47.4 mL, 0.38 mol) drop wise and stirred at RT for 12 h. The reaction mixture was quenched with ice cold water and extracted with diethyl ether (2×250 mL). The separated the organic layer was washed with brine, dried over anhydrous $Na_2SO_4$ and concentrated under reduced pressure. The crude material was purified by silica gel column chromatography eluting with 5% EtOAc/n-hexane to afford C (80 g, 62%).

$^1$H-NMR: (400 MHz, DMSO-$d_6$): δ 7.41-7.25 (m, 10H), 5.09 (s, 2H), 4.55-4.50 (m, 1H), 4.34-4.30 (m, 1H), 2.09 (s, 3H), 1.42 (s, 9H), 1.15 (d, 3H).

Synthesis of (2S, 3R)-benzyl 2-amino-3-(benzyloxy) butanoate (Int-D)

To a stirred solution of C (80 g, 0.20 mol) in methanol (100 mL) was added methanolic HCl (70 mL) under $N_2$ atmosphere and stirred for 12 h. After consumption of the starting material (by TLC), the reaction mixture was concentrated under reduced pressure. The crude material was washed with n-hexane and dried under reduced pressure to afford Int-D (45 g, 75%) as HCl salt.

$^1$H-NMR: (400 MHz, DMSO-$d_6$): δ 7.35-7.30 (m, 10H), 5.25 (q, 2H), 4.58-4.52 (m, 3H), 4.37 (d, 1H), 4.27 (br s, 1H), 4.15-4.10 (m, 1H), 1.30 (d, 3H).

LCMS (m/z): 300.2 [$M^+$+1]

Synthesis of (S)-methyl pyrrolidine-2-carboxylate (2)

To a stirred solution of L-proline 1 (100 g, 0.87 mol) in methanol (800 mL) was added thionyl chloride (76.9 mL, 1.04 mol) slowly drop wise at 0° C. The reaction mixture was heated to reflux for 12 h. After consumption of the starting material (by TLC), the reaction was concentrated under reduced pressure. The residue was washed with n-hexane to afford 2 (143.9 g, HCl salt).

$^1$H-NMR: (400 MHz, CDCl$_3$): δ 3.89 (s, 3H), 3.68-3.62 (m, 2H), 3.59-3.47 (m, 2H), 2.49-2.37 (m, 1H), 2.27-2.05 (m, 3H).

LCMS (m/z): 166 [$M^+$+1]

Synthesis of (S)-1-tert-butyl 2-methyl pyrrolidine-1,2-dicarboxylate (3)

To a stirred solution of 2 (35 g, 0.22 mol) in $CH_2Cl_2$ (175 mL) was added $Et_3N$ (90 mL, 0.65 mol) followed by Boc-anhydride (56.9 mL, 0.26 mol) at 0° C. The reaction mixture was stirred at RT for 16 h. After consumption of the starting material (by TLC), the reaction was diluted with water (100 mL) and extracted with $CH_2Cl_2$ (2×100 mL). The organic layer was washed with water, brine, dried over $Na_2SO_4$ and concentrated. The crude material was purified by silica gel column chromatography eluting with 30% EtOAc/n-hexane to afford 3 (41 g, 95%).

$^1$H-NMR: (400 MHz, CDCl$_3$): δ 4.25-4.21 (m, 1H), 3.75 (s, 3H), 3.57-3.26 (m, 2H), 2.29-2.10 (m, 1H), 1.99-1.75 (m, 3H), 1.45 (s, 9H).

LCMS (m/z): 130 [($M^+$+1)-Boc]

Synthesis of 1-tert-butyl 2-methyl 2-((benzyloxy) methyl) pyrrolidine-1, 2-dicarboxylate (4)

To a stirred solution of 3 (100 g, 0.43 mol) in THF (800 mL) was added LiHMDS (873 mL, 0.87 mol) at −78° C. and stirred for 1 h. To this BOM-chloride (93.2 mL, 0.65 mol) was added drop wise at −78° C. and stirred for 2 h at −20° C. After consumption of the starting material (by TLC), the reaction was quenched with aqueous $NH_4Cl$ solution and extracted with EtOAc. The separated organic layer was washed with water, dried over $Na_2SO_4$ and concentrated to afford 4 (180 g, crude). This material was directly taken for the next step without further purification.

LCMS (m/z): 250 [($M^+$+1)-Boc]

Synthesis of 2-((benzyloxy) methyl)-1-(tert-butoxycarbonyl) pyrrolidine-2-carboxylic acid (5)

To a stirred solution of 4 (100 g, 0.28 mol) in methanol (200 mL) was added 2N NaOH solution (300 mL) at RT. The reaction mixture was heated to reflux for 4 h. After consumption of the starting material (by TLC), the solvent from the reaction was evaporated under reduced pressure and diluted with EtOAc (100 mL). The aqueous layer was acidified using citric acid solution and extracted with $CH_2Cl_2$ (2×250 mL). The separated organic layer was washed with water, dried over $Na_2SO_4$ and concentrated to afford 5 (60 g, 63%).

$^1$H-NMR: (400 MHz, CDCl$_3$): δ 7.37-7.32 (m, 5H), 4.61 (s, 2H), 4.05-3.88 (m, 2H), 3.65-3.42 (m, 2H), 2.54-2.46 (m, 2H), 1.95 (br s, 2H), 1.57 (s, 9H).

LCMS (m/z): 334 [$M^+$−1]

Synthesis of 1-(tert-butoxycarbonyl)-2-(hydroxymethyl)pyrrolidine-2-carboxylic acid (6)

To a stirred solution of 5 (10 g, 29.81 mmol) in methanol (300 mL) was added 50% wet 10% Pd/C (5 g) at RT and stirred for 24 h under $H_2$ atmosphere (balloon pressure). After consumption of the starting material (by TLC), the reaction mixture was filtered through a pad of celite and the pad was washed with methanol. Obtained filtrate was concentrated under reduced pressure to afford 6 (6 g, 82%).

$^1$H-NMR: (400 MHz, DMSO-$d_6$): δ 12.55 (br m, 1H), 3.99 (d, 1H), 3.88 (d, 1H), 7.65-7.60 (m, 1H), 3.51-3.45 (m, 1H), 3.39-3.34 (m, 1H), 2.32-2.14 (m, 1H), 1.98-1.69 (m, 3H), 1.39 (s, 9H).

Synthesis of tert-butyl 2-(((2S, 3R)-1, 3-bis(benzyloxy)-1-oxobutan-2-yl) carbamoyl)-2-(hydroxymethyl) pyrrolidine-1-carboxylate (7)

To a stirred solution of 6 (3 g, 12.2 mmol) in $CH_2Cl_2$ (100 mL) was added Int-D (5.8 g, 14.6 mmol), EDCI.HCl (2.8 g, 14.6 mmol) followed by HOBt (1.99 g, 14.6 mmol) and DIPEA (4.8 g, 36.7 mmol) at RT and stirred for 16 h. After consumption of the starting material (by TLC), the reaction mixture was diluted with water (100 mL) and extracted with $CH_2Cl_2$ (2×100 mL). The separated organic layer was washed with brine, dried over anhydrous $Na_2SO_4$, filtered and concentrated under reduced pressure. Obtained crude material was purified by silica gel column chromatography to afford 7 (1.6 g, 25%).

$^1$H-NMR: (400 MHz, DMSO-$d_6$): δ 8.25-8.12 (m, 1H), 7.31-7.27 (m, 10H), 5.85 (t, 1H), 5.14 (s, 2H), 4.54-4.49 (m, 2H), 4.31 (dd, 1H), 4.15-4.07 (m, 1H), 3.91-3.50 (m, 1H), 3.52-3.37 (m, 1H), 3.31-3.27 (m, 2H), 2.35-2.07 (m, 1H), 1.95-1.90 (m, 1H), 1.73-1.52 (m, 2H), 1.39-1.27 (m, 9H), 1.19-1.12 (m, 3H).

Mass (ESI): m/z 527.4 [$M^+$+1]

Synthesis of tert-butyl 2-((2S,3R)-1,3-bis(benzyloxy)-1-oxobutan-2-yl)-1-oxo-2,5-diazaspiro[3.4]octane-5-carboxylate (8)

To a stirred solution of 7 (1.4 g, 2.65 mmol) in THF (20 mL) was added triphenylphosphine (1.1 g, 3.98 mmol) and DTAD (1.2 g, 3.98 mmol). The reaction mixture was stirred at RT for 16 h. After consumption of the starting material (by TLC), the reaction was concentrated under reduced pressure. The crude material was purified by silica gel column chromatography to afford 8-F1 (0.6 g) and 8-F2 (0.55 g).

Synthesis of (2S, 3R)-2-(5-(tert-butoxycarbonyl)-1-oxo-2, 5-diazaspiro [3.4] octan-2-yl)-3-hydroxybutanoic acid (9)

To a stirred solution of 8-F1 and 8-F2 (0.6 g) in methanol (50 mL) was added 10% Pd/C (120 mg) at RT and stirred for 6 h under $H_2$ atmosphere (balloon pressure). After consumption of the starting material (by TLC), the reaction mixture was filtered through a pad of celite and the pad was washed with methanol. The filtrate was concentrated under reduced pressure to give crude, trituration using diethyl ether afforded 9 (0.3 g, 82%) as an off-white solid.

$^1$H-NMR: (500 MHz, DMSO-$d_6$): δ 12.95 (br s, 1H), 4.97 (br s, 1H), 4.24-4.20 (m, 1H), 4.14-4.07 (m, 1H), 3.84 (d, 1H), 3.53 (t, 1H), 3.41-3.35 (m, 1H), 3.27-3.22 (m, 1H), 2.14-2.08 (m, 2H), 1.84-1.80 (m, 2H), 1.42 (s, 9H), 1.24 (d, 3H).

LCMS (m/z): 329.6 [M$^+$+1]

Synthesis of tert-butyl 2-((2S, 3R)-1-amino-3-hydroxy-1-oxobutan-2-yl)-1-oxo-2, 5-diazaspiro [3.4] octane-5-carboxylate (10)

To a stirred solution of 9 (5 g, 15.2 mmol) in $CH_2Cl_2$ (100 mL) was added ammonium chloride (2 g, 38.1 mmol), EDCI.HCl (3.5 g, 18.2 mmol) followed by HOBt (5.9 g, 45.7 mmol) and DIPEA (5.9 g, 45.7 mmol) at RT and stirred for 16 h. After consumption of the starting material (by TLC), the reaction mixture was diluted with water (100 mL) and extracted with $CH_2Cl_2$ (2×100 mL). The separated organic layer was washed with brine, dried over anhydrous $Na_2SO_4$, filtered and concentrated under reduced pressure. The crude material was triturated with $Et_2O$ (50 mL) and n-pentane (50 mL) to afford 10 (2.5 g, 51%) as an off-white solid.

$^1$H-NMR: (400 MHz, DMSO-$d_6$): δ 7.51 (br s, 1H), 7.19 (br s, 1H), 4.64 (d, 1H), 4.07-3.95 (m, 2H), 3.78 (m, 1H), 3.62-3.35 (m, 2H), 3.27-3.25 (m, 1H), 2.18-2.05 (m, 2H), 1.86-1.74 (m, 2H), 1.41 (s, 9H), 1.12 (d, 3H).

LCMS (m/z): 328.2 [M$^+$+1]

Synthesis of (2S, 3R)-3-hydroxy-2-(1-oxo-2, 5-diazaspiro[3.4]octan-2-yl)butanamide (Compound X)

To a stirred solution of 10 (2.2 g, 6.70 mmol) in $CH_2Cl_2$ (25 mL) was added TFA (7.6 g, 67 mmol) at 0° C. and stirred at RT for 2 h. The reaction mixture was concentrated under reduced pressure to afford Compound X (2 g, 87%) as TFA salt.

$^1$H-NMR: (400 MHz, $D_2O$): δ 4.33-4.29 (m, 2H), 4.09 (d, 1H), 3.95 (d, 1H), 3.57-3.48 (m, 2H), 2.51-2.46 (m, 2H), 2.25-2.19 (m, 2H), 1.31 (d, 3H).

LCMS (m/z): 455 [2M$^+$+1]

Example 2

Synthesis of Compound Z

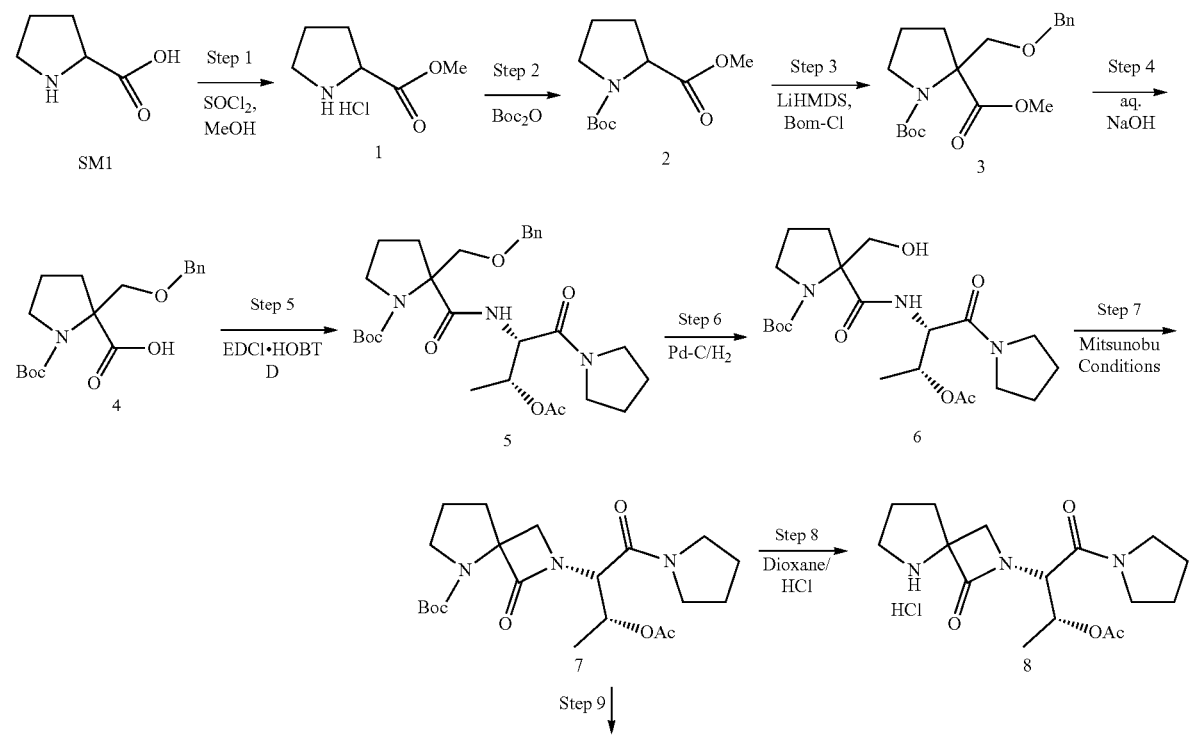

Scheme 3.

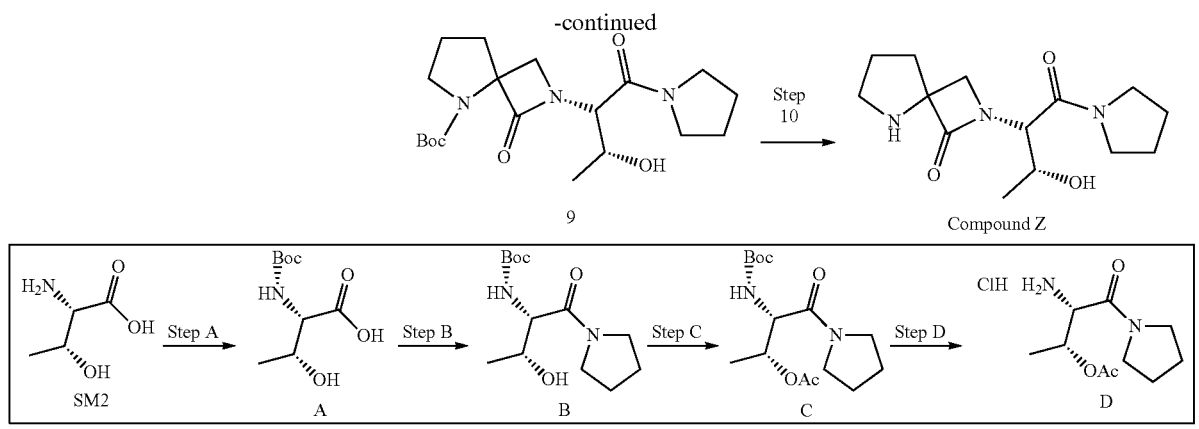

Synthesis of (2S, 3R)-2-((tert-butoxycarbonyl)amino)-3-hydroxybutanoic acid (A)

To a stirred solution of (2S, 3R)-2-amino-3-hydroxybutanoic acid (SM2) (30 g, 0.25 mol) in THF (150 mL) and water (150 mL) was added $NaHCO_3$ (65 g, 0.75 mol) followed by Boc-anhydride (66 mL, 0.302 mol) at 0° C. The reaction mixture was stirred at RT for 16 h. After consumption of the starting material (by TLC), the reaction mixture was extracted with EtOAc (2×150 mL). The aqueous layer was acidified using 2N HCl and then extracted with 10% $MeOH/CH_2Cl_2$. The separated organic extracts were dried over anhydrous $Na_2SO_4$, filtered and concentrated under vacuum to afford A (30 g, 63%).

$^1$H-NMR: (400 MHz, $CDCl_3$): δ 5.92-5.70 (m, 2H), 5.55 (d, 1H), 4.42 (br s, 1H), 4.29 (d, 1H), 1.47 (s, 9H), 1.25 (d, 3H)

LCMS (m/z): 218 [M$^+$−1]

Synthesis of tert-butyl ((2S, 3R)-3-hydroxy-1-oxo-1-(pyrrolidin-1-yl) butan-2-yl) carbamate (B)

To a stirred solution of A (13 g, 59.36 mmol) in DMF (65 mL) was added EDCI.HCl (12.5 g, 65.2 mmol) followed by HOBt (8.8 g, 65.2 mmol) at 0° C. After stirring for 5 min, DIPEA (30.6 mL, 0.17 mol) followed by pyrrolidine (4.6 g, 65.2 mmol) was added to the reaction mixture and stirring was continued for another 16 h at RT. The reaction mixture was washed with water and extracted with EtOAc (2×100 mL). The organic layer was washed with brine, dried over anhydrous $Na_2SO_4$ and concentrated under vacuum. The crude was purified by column chromatography to afford B (5 g, 31%).

$^1$H-NMR: (400 MHz, $CDCl_3$): δ 5.51 (br s, 1H), 4.32 (d, 1H), 4.15-4.10 (m, 1H), 3.77-3.74 (m, 1H), 3.55-3.46 (m, 3H), 1.99-1.94 (m, 2H), 1.91-1.85 (m, 2H), 1.47 (s, 9H), 1.26 (t, 1H), 1.29 (d, 3H).

Synthesis of (2R, 3S)-3-((tert-butoxycarbonyl)amino)-4-oxo-4-(pyrrolidin-1-yl) butan-2-yl acetate (D)

To a stirred solution of B (4 g, 14.7 mmol) in $CH_2Cl_2$ (40 mL) was added $Et_3N$ (5.1 mL, 36.7 mmol) followed by acetic anhydride (1.7 g, 17.6 mmol) and catalytic amount of DMAP at 0° C. The reaction mixture was stirred at RT for 16 h. After consumption of the starting material (by TLC), the reaction mixture was diluted with water and separated the organic layer. Organic layer was washed with water, dried over anhydrous $Na_2SO_4$ and concentrated under reduced pressure. The crude residue obtained was purified by silica gel column chromatography to give C. To this 1,4-dioxane/HCl (20 mL) was added and stirred at RT for 2 h. The reaction mixture was concentrated under vacuum and the residue was washed with $Et_2O$ (2×15 mL) to afford D (3.5 g, 97%) as HCl salt.

$^1$H-NMR: (500 MHz, DMSO-$d_6$) (Rotamers): δ 8.49 (br s, 3H), 8.15 (br s, 1H), 5.14-5.10 (m, 1H), 4.26-4.22 (m, 1H), 3.97-3.95 (m, 1H), 3.59 (s, 2H), 2.09 (s, 3H), 1.98 (s, 2H), 1.87-1.80 (m, 2H), 1.26 (d, 3H).

LCMS (m/z): 215.1 [M$^+$+1]

Synthesis of methyl pyrrolidine-2-carboxylate (1)

To a stirred solution of pyrrolidine-2-carboxylic acid (SM1) (100 g, 0.87 mol) in methanol (800 mL) was added thionyl chloride (76.9 mL, 1.04 mol) slowly drop wise at 0° C. The reaction mixture was heated to reflux for 12 h. After consumption of the starting material (by TLC), the reaction was concentrated under vacuum. The residue was washed with n-Hexane and distilled off the solvent to afford 1 (143.9 g, HCl salt).

$^1$H-NMR: (400 MHz, $CDCl_3$) (Rotamers): δ 3.89 (s, 3H), 3.68-3.62 (m, 2H), 3.59-3.47 (m, 2H), 2.49-2.37 (m, 1H), 2.27-2.05 (m, 3H).

LCMS (m/z): 166 [M$^+$+1]

Synthesis of 1-tert-butyl 2-methyl pyrrolidine-1,2-dicarboxylate (2)

To a stirred solution of 1 (35 g, 0.22 mol) in $CH_2Cl_2$ (175 mL) were added $Et_3N$ (90 mL, 0.65 mol) followed by Boc-anhydride (56.9 mL, 0.26 mol) at 0° C. The reaction mixture was stirred at RT for 16 h. After consumption of the starting material (by TLC), the reaction was diluted with water (100 mL) and extracted with $CH_2Cl_2$ (2×100 mL). The organic layer was washed with water, brine, dried over $Na_2SO_4$ and concentrated. The crude material was purified by silica gel column chromatography eluting with 30% EtOAc/Hexane to afford 2 (41 g, 95%).

$^1$H-NMR: (400 MHz, $CDCl_3$) (Rotamers): δ 4.25-4.21 (m, 1H), 3.75 (s, 3H), 3.57-3.26 (m, 2H), 2.29-2.10 (m, 1H), 1.99-1.75 (m, 3H), 1.45 (s, 9H).

LCMS (m/z): 130 [(M$^+$+1)-Boc]

Synthesis of 1-tert-butyl 2-methyl 2-((benzyloxy) methyl) pyrrolidine-1, 2-dicarboxylate (3)

To a stirred solution of 2 (100 g, 0.43 mol) in THF (800 mL) was added LiHMDS (873 mL, 0.87 mol) at −78° C. and stirred for 1 h. To this BOM-chloride (93.2 mL, 0.65 mol) was added drop wise at −78° C. and stirred for 2 h at −20° C. After consumption of the starting material (by TLC), the reaction was quenched with NH$_4$Cl at 0° C. The separated organic layer was washed with water, dried over Na$_2$SO$_4$ and concentrated to afford 3 (180 g, crude). This material was directly taken for the next step without further purification.
LCMS (m/z): 250 [(M$^+$+1)-Boc]

Synthesis of 2-((benzyloxy) methyl)-1-(tert-butoxycarbonyl) pyrrolidine-2-carboxylic acid (4)

To a stirred solution of 3 (100 g, 0.28 mol) in methanol (200 mL) was added 2N NaOH solution (300 mL) at RT. The reaction mixture was heated to reflux for 4 h. After consumption of the starting material (by TLC), the solvent from the reaction was evaporated under vacuum and diluted with EtOAc (100 mL). The aqueous layer was acidified using citric acid solution and extracted with CH$_2$Cl$_2$ (2×250 mL). The separated organic layer was washed with water, dried over Na$_2$SO$_4$ and concentrated to afford 4 (60 g, 63%).
$^1$H-NMR: (400 MHz, CDCl$_3$) (Rotamers): δ 7.37-7.32 (m, 5H), 4.61 (s, 2H), 4.05-3.88 (m, 2H), 3.65-3.42 (m, 2H), 2.54-2.46 (m, 2H), 1.95 (br s, 2H), 1.57 (s, 9H).
LCMS (m/z): 334 [M$^+$−1]

Synthesis of tert-butyl 2-(((2S, 3R)-3-acetoxy-1-oxo-1-(pyrrolidin-1-yl) butan-2-yl) carbamoyl)-2-((benzyloxy) methyl) pyrrolidine-1-carboxylate (5)

To a stirred solution of D (1 g, 2.90 mmol) in DMF (8 mL) was added EDCI.HCl (0.63 g, 3.28 mmol) followed by HOBt (0.44 g, 3.28 mmol) at 0° C. After being stirred for 5 min, DIPEA (1.3 mL, 7.46 mmol) followed by compound 4 (0.74 g, 3.58 mmol) was added to the reaction mixture and stirring was continued for another 16 h at RT. The reaction mixture was washed with water and extracted with EtOAc (2×500 mL). The organic layer was washed with brine, dried over anhydrous Na$_2$SO$_4$ and concentrated under vacuum. The crude was purified by column chromatography to afford 5 (0.6 g, 38%).
LCMS (m/z): 532 [M$^+$+1]

Synthesis of tert-butyl 2-(((2S, 3R)-3-acetoxy-1-oxo-1-(pyrrolidin-1-yl) butan-2-yl) carbamoyl)-2-(hydroxymethyl) pyrrolidine-1-carboxylate (6)

To a stirred solution of 5 (4.5 g, 8.40 mmol) in MeOH (40 mL) was added wet 10% Pd/C (1.5 g) under inert atmosphere and stirred for 4 h under H$_2$ atmosphere (balloon pressure). The reaction mixture was filtered through celite pad and concentrated under reduced pressure to afford 6 (3.0 g, 81%).
LCMS (m/z): 442.5 [M$^+$+1]

Synthesis of tert-butyl 2-((2S, 3R)-3-acetoxy-1-oxo-1-(pyrrolidin-1-yl) butan-2-yl)-1-oxo-2, 5-diazaspiro [3.4] octane-5-carboxylate (7)

To a stirred solution of 6 (3 g, 6.70 mmol) in THF (25 mL) was added triphenylphosphine (2 g, 7.40 mmol) followed by DTAD (2.5 g, 10.2 mmol). The reaction mixture was stirred at RT for 16 h. After consumption of the starting material (by TLC), the reaction was concentrated under reduced pressure. The crude material was purified by silica gel column chromatography eluting with 10% MeOH/CH$_2$Cl$_2$ to afford 7 (1.2 g with TPPO, 43%).
$^1$H-NMR: (400 MHz, DMSO-d$_6$): δ 5.25-5.19 (m, 1H), 4.65 (d, 1H), 3.61-3.57 (m, 3H), 3.47-3.42 (m, 2H), 3.41-3.25 (m, 4H), 2.05 (s, 4H), 1.95-1.71 (m, 7H), 1.42 (s, 10H).
LCMS (m/z): 424.4 [M$^+$+1]

Synthesis of (2R, 3S)-4-oxo-3-(1-oxo-2, 5-diazaspiro [3.4] octan-2-yl)-4-(pyrrolidin-1-yl) butan-2-yl acetate (8)

A stirred solution of 7 (0.4 g, 0.94 mmol) in 1,4-dioxane/HCl (5 mL) was cooled to 0° C. and stirred at RT for 1 h. After consumption of the starting material (by TLC), the reaction mixture was concentrated under reduced pressure. The crude material was washed with n-pentane followed by EtOAc to afford 8 (0.22 g, 65%).
$^1$H-NMR: (400 MHz, D$_2$O): δ 4.62 (d, 1H), 4.41-4.29 (m, 2H), 4.24 (d, 1H), 3.89-3.77 (m, 3H), 3.54-3.49 (m, 3H), 2.57-2.52 (m, 1H), 2.49 (s, 3H), 2.42-2.00 (m, 8H), 1.30 (d, 3H).
LCMS (m/z): 324.3 [M$^+$+1]
UPLC Purity: 99.37%

Synthesis of tert-butyl 2-((2S, 3R)-3-hydroxy-1-oxo-1-(pyrrolidin-1-yl) butan-2-yl)-1-oxo-2, 5-diazaspiro [3.4] octane-5-carboxylate (9)

A solution of 7 (0.15 g, 0.41 mmol) in aqueous NH$_3$ (2 mL) was stirred at RT for 4 h. After consumption of the starting material (by TLC), the reaction diluted with CH$_2$Cl$_2$ (75 mL). The separated organic layer was dried over anhydrous Na$_2$SO$_4$ and concentrated under reduced pressure to afford 9 (0.1 g, 76%).
LCMS (m/z): 382 [M$^+$+1]

Synthesis of 2-((2S, 3R)-3-hydroxy-1-oxo-1-(pyrrolidin-1-yl) butan-2-yl)-2, 5-diazaspiro [3.4] octan-1-one (Compound Z)

To a stirred solution of 9 (0.2 g, 0.63 mmol) in CH$_2$Cl$_2$ (2 mL) was added TFA (0.3 mL) at 0° C. and stirred at RT for 1 h. The reaction mixture was concentrated under vacuum and the residue was diluted with water and extracted with CH$_2$Cl$_2$ (2×25 mL). The separated organic layer was dried over anhydrous Na$_2$SO$_4$, filtered and concentrated under vacuum to afford Compound Z (0.2 g, 80%) as TFA salt.
$^1$H-NMR: (400 MHz, D$_2$O): δ 4.64 (t, 1H), 4.25-4.21 (m, 1H), 4.09 (d, 1H), 3.99-3.87 (m, 1H), 3.70 (t, 2H), 3.55-3.47 (m, 5H), 2.52-2.34 (m, 2H), 2.25-2.22 (m, 2H), 2.08-1.98 (m, 5H), 1.25 (t, 3H).
LCMS (m/z): 282.4 [M$^+$+1]

Scheme 2S-I-1

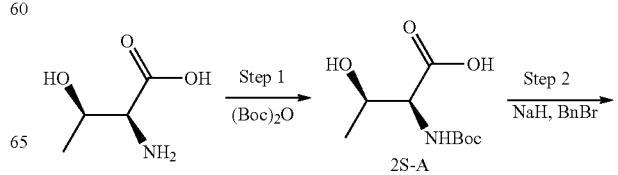

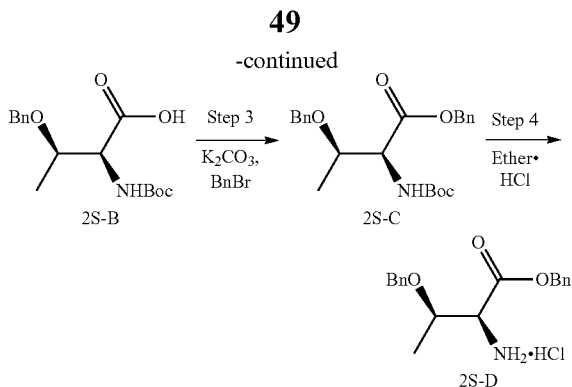

Synthesis of (2S, 3R)-2-((tert-butoxycarbonyl)amino)-3-hydroxybutanoic acid (2S-A)

To a stirring solution of L-threonine (50 g, 420 mol) in THF/water (500 mL/500 mL) were added NaHCO$_3$ (111 g, 1.05 mol) and stirred at RT for 30 min. The reaction mixture was cooled to 0° C. and Boc-anhydride (137 mL, 630 mmol) was added drop wise and the stirring was continued at RT for 16 h. After consumption of the starting material (by TLC), the reaction mixture was concentrated under reduced pressure and obtained residue was diluted with water (100 mL) and acidified by using 1N HCl (pH~3). The aqueous layer was extracted with EtOAc (2×250 mL). The combined organic layer was washed with brine (1×200 mL), dried over anhydrous Na$_2$SO$_4$, filtered and concentrated under reduced pressure to afford compound 2S-A (80 g, 87%) as thick syrup.

$^1$H-NMR: (500 MHz, DMSO-d$_6$): δ 12.5 (br s, 1H), 6.30 (d, J=8.5 Hz, 1H), 4.50 (br s, 1H), 4.05-4.02 (m, 1H), 3.88-3.86 (m, 1H), 1.39 (s, 9H), 1.08 (d, J=6.0 Hz, 3H);

LCMS m/z: 218.1 [M$^+$−1]

Synthesis of (2S, 3R)-3-(benzyloxy)-2-((tert-butoxycarbonyl) amino) butanoic acid (2S-B)

To a stirring solution of 2S-A (40 g, 182 mmol) in DMF (400 mL) was added 60% NaH (18.2 g, 758 mmol) portion wise at −20° C. under N$_2$ atmosphere and stirred for 2 h. To this added benzyl bromide (66.8 mL, 0.55 mol) drop wise and the reaction mixture was stirred at RT for 3 h. After consumption of the starting material (by TLC), the reaction mixture was quenched with ice cold water and washed with diethyl ether (2×250 mL). The separated aqueous layer was acidified using citric acid solution (100 mL) and extracted with EtOAc (2×250 mL). The combined organic layers were dried over anhydrous Na$_2$SO$_4$ and concentrated under reduced pressure to afford compound 2S-B (45 g, 80%) as thick syrup.

$^1$H-NMR: (500 MHz, DMSO-d$_6$): δ 12.64 (br s, 1H), 7.34-7.25 (m, 5H), 6.46 (d, J=8.5 Hz, 1H), 4.53 (d, J=11.5 Hz, 1H), 4.39 (d, J=12.0 Hz, 1H), 4.00-3.98 (m, 2H), 1.39 (s, 9H), 1.15 (d, J=6.0 Hz, 3H);

Synthesis of (2S, 3R)-benzyl 3-(benzyloxy)-2-((tert-butoxycarbonyl) amino) butanoate (2S-C)

To a stirring solution of compound 2S-B (45 g, 146 mmol) in DMF (400 mL) was added K$_2$CO$_3$ (40 g, 292 mmol) under N$_2$ atmosphere and stirred for 30 min. To this benzyl bromide (21 mL, 175 mmol) was added drop wise at 0° C. and stirred at RT for 16 h. The reaction mixture was quenched with ice cold water and extracted with diethyl ether (2×250 mL). The separated organic layer was washed with brine, dried over anhydrous Na$_2$SO$_4$ and concentrated under reduced pressure. The crude material was purified by silica gel column chromatography eluting with 20% EtOAc/n-hexane to afford compound 2S-C (48 g, 82%) as thick syrup.

$^1$H-NMR: (500 MHz, DMSO-d$_6$): δ 7.37-7.18 (m, 10H), 6.81 (d, J=9.0 Hz, 1H), 5.08 (s, 2H), 4.49 (d, J=12.0 Hz, 1H), 4.32 (d, J=12.0 Hz, 1H), 4.25-4.22 (m, 1H), 4.01-3.98 (m, 1H), 1.38 (s, 9H), 1.15 (d, J=6.0 Hz, 3H)

Mass (ESI): m/z 399.4[M$^+$+1];

Synthesis of (2S, 3R)-benzyl 2-amino-3-(benzyloxy) butanoate (2S-D)

To a stirring solution of compound 2S-C (48 g, 120 mmol) in diethylether (50 mL) was added diethylether saturated with HCl (350 mL) at 0° C. and stirred at RT for 10 h. After consumption of the starting material (by TLC), the reaction mixture was concentrated under reduced pressure. The crude material was triturated with diethyl ether/n-pentane (50 mL/50 mL) and dried under reduced pressure to afford compound 2S-D (28 g, 77%) as semisolid (HCl salt).

$^1$H-NMR: (400 MHz, DMSO-d$_6$): δ 8.59 (s, 2H), 7.50-7.25 (m, 10H), 5.23 (d, J=12.5 Hz, 1H), 5.16 (d, J=12.5 Hz, 1H), 4.54 (d, J=12.0 Hz, 1H), 4.36 (d, J=12.0 Hz, 1H), 4.12-4.09 (m, 1H), 4.09-3.99 (m, 1H), 1.29 (d, J=6.5 Hz, 3H)

Mass (ESI): m/z 299.4[M$^+$+1];

Scheme 2S-I-2

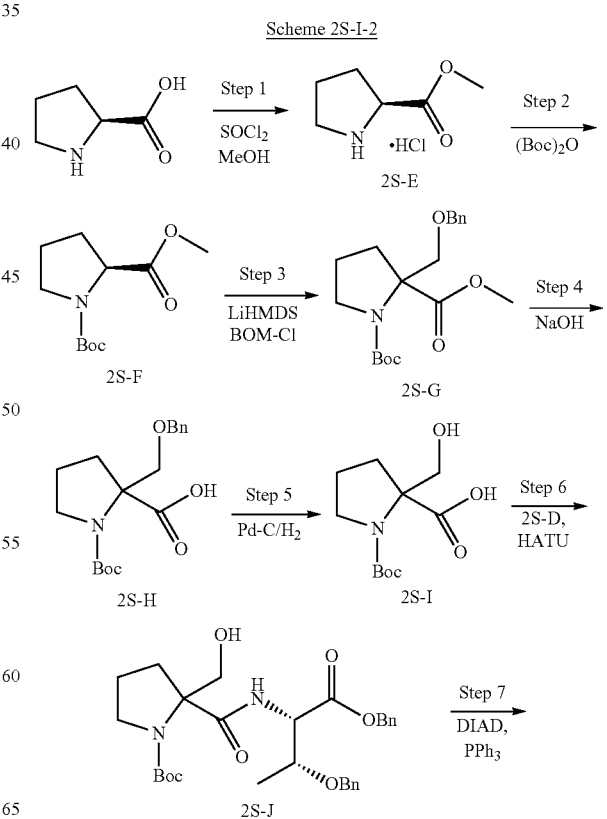

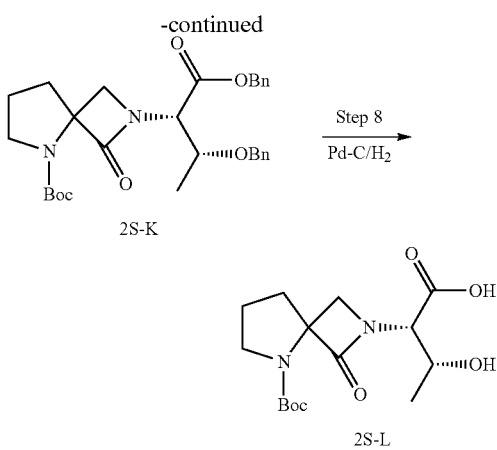

Step 8
Pd-C/H₂

2S-K

2S-L

Synthesis of methyl pyrrolidine-2-carboxylate (2S-E)

To a stirring solution of L-proline (50 g, 434 mmol) in methanol was added thionyl chloride (37.5 ml, 521 mmol) at 0° C. and heated to 70° C. for 16 h. The reaction mixture was brought to RT and concentrated under vacuum to afford compound 2S-E as (70 g, 99%) as thick syrup (hydrochloride salt).

$^1$H-NMR: (500 MHz, DMSO-$d_6$): δ 4.15-4.13 (m, 1H), 3.65 (s, 3H), 3.35-3.30 (m, 2H), 2.23-2.15 (m, 1H), 1.86-1.78 (m, 3H), 1.41 (s, 9H);
LCMS m/z: 129 [M$^+$+1]

Synthesis of 1-tert-butyl 2-methyl pyrrolidine-1,2-dicarboxylate (2S-F)

To a stirring solution of compound 2S-E (70 g, 422 mmol) in CH$_2$Cl$_2$ (700 mL) were added Et$_3$N (183 mL, 1.26 mol) at 0° C. and stirred for 10 min. After added Boc-anhydride (184 mL, 845 mmol) at 0° C. and the reaction mixture was stirred at RT for 16 h. After consumption of the starting material (by TLC), the reaction was diluted with water (200 mL) and extracted with CH$_2$Cl$_2$ (2×200 mL). The combined organic layer was washed with citric acid (1×150 mL), brine (1×200 mL). The organic layer was dried over Na$_2$SO$_4$ and concentrated under reduced pressure to afford crude compound which was purified by column chromatography by eluting 50% EtOAC/n-hexane to obtain compound 2S-F (80 g, 83%) as thick syrup.

$^1$H-NMR: (400 MHz, DMSO-$d_6$): δ 4.15-4.13 (m, 1H), 3.65 (s, 3H), 3.35-3.30 (m, 2H), 2.23-2.15 (m, 1H), 1.86-1.78 (m, 3H), 1.41 (s, 9H);
LCMS m/z: 229 [(M$^+$+1)-Boc].

Synthesis of 1-tert-butyl 2-methyl 2-((benzyloxy) methyl) pyrrolidine-1, 2-dicarboxylate (2S-G)

To a stirring solution of compound 2S-F (25 g, 109 mmol) in THF (250 mL) was added LiHMDS (240 mL, 240 mmol) at –20° C. and stirred for 2 h. To this BOM-chloride (23 mL, 163 mmol) was added drop wise at –30° C. and stirred for 2 h. After consumption of the starting material (by TLC), the reaction was quenched with aqueous NH$_4$Cl solution (100 mL) and extracted with EtOAc (2×200 mL). The combined organic layer was washed with water (2×150 mL) followed by brine solution (2×100 mL). The organic layer was dried over Na$_2$SO$_4$ and concentrated to obtain crude compound which was purified by column chromatography by eluting 10% EtOAc/n-hexane to afford compound 2S-G (30 g, 79%) as thick syrup.

$^1$H-NMR: (500 MHz, DMSO-$d_6$): δ 7.36-7.22 (m, 5H), 4.59-4.48 (m, 2H), 4.02-3.88 (m, 1H), 3.63 (s, 3H), 3.49-3.35 (m, 2H), 3.34-3.30 (m, 1H), 2.31-2.23 (m, 1H), 2.04-1.89 (m, 2H), 1.82-1.78 (m, 1H);
LCMS m/z: 349.4 [(M$^+$+1)-Boc]

Synthesis of 2-((benzyloxy) methyl)-1-(tert-butoxycarbonyl) pyrrolidine-2-carboxylic acid (2S-H)

To a stirring solution of compound 2S-G (30 g, 86 mmol) in methanol (70 mL) was added NaOH solution (6.88 g in 70 mL H$_2$O) at RT. The reaction mixture was heated to 70° C. for 16 h. After consumption of the starting material (by TLC), the solvent from the reaction was evaporated under reduced pressure and diluted with EtOAc (2×200 mL). The separated aqueous layer was acidified using citric acid solution (pH~3) and extracted with EtOAc (2×250 mL). The combined organic layer was dried over Na$_2$SO$_4$ and concentrated to afford crude was triturated with n-hexane to obtain compound 2S-H (25 g, 86.8%) as an off-white solid.

$^1$H-NMR: (400 MHz, DMSO-$d_6$): δ 12.35 (br s, 1H), 7.37-7.29 (m, 5H), 4.56-4.48 (m, 2H), 4.06-4.00 (m, 1H), 3.92-3.89 (m, 1H), 3.66-3.45 (m, 1H), 3.37-3.28 (m, 1H), 2.31-2.20 (m, 1H), 2.05-1.97 (m, 1H), 1.87-1.75 (m, 2H), 1.38 (s, 9H);
LCMS m/z: 335.3 [M$^+$+1]

Synthesis of 1-(tert-butoxycarbonyl)-2-(hydroxymethyl) pyrrolidine-2-carboxylic acid (2S-I)

To a stirring solution of compound 2S-H (25 g, 74 mmol) in methanol (150 mL) was added 50% wet 10% Pd/C (7 g) at RT and stirred for 10 h under H$_2$ atmosphere. After consumption of the starting material (by TLC), the reaction mixture was filtered through a pad of celite and the pad was washed with methanol (100 mL). Obtained filtrate was concentrated under reduced pressure to afford compound 2S-I (15 g, 82.8%) as white solid.

$^1$H-NMR: (400 MHz, DMSO-$d_6$): δ 4.66 (br s, 1H), 3.96-3.83 (m, 1H), 3.63-3.59 (m, 1H), 3.49-3.41 (m, 1H), 3.34-3.25 (m, 1H), 2.30-2.17 (m, 1H), 1.95-1.72 (m, 3H), 1.38 (s, 9H).
Mass (ESI): m/z 245 [M$^+$+1]

Synthesis of tert-butyl 2-(((2S, 3R)-1, 3-bis (benzyloxy)-1-oxobutan-2-yl) carbamoyl)-2-(hydroxymethyl) pyrrolidine-1-carboxylate (2S-J)

To a stirring solution of compound 2S-I (18 g, 73.4 mmol) in CH$_2$Cl$_2$ (180 mL) were added DIPEA (40 mL, 220 mmol), 2S-D (21.9 g, 73.4 mmol), HATU (41.8 g, 110 mmol) at RT and stirred for 16 h. After consumption of the starting material (by TLC), the reaction mixture was diluted with water (50 mL) and extracted with CH$_2$Cl$_2$ (2×100 mL). The combined organic layer was washed with brine, dried over anhydrous Na$_2$SO$_4$, filtered and concentrated under reduced pressure. Obtained crude material was purified by silica gel column chromatography eluting with 30% EtOAc/n-hexane to afford compound 2S-J (20 g, 52%) as pale yellow thick syrup.

$^1$H-NMR: (400 MHz, DMSO-$d_6$): δ 8.25-8.12 (m, 1H), 7.31-7.27 (m, 10H), 5.85 (t, J=4.8 Hz, 1H), 5.14 (s, 2H), 4.54-4.49 (m, 2H), 4.31-4.20 (m, 1H), 4.15-4.07 (m, 1H), 3.91-3.50 (m, 1H), 3.52-3.37 (m, 1H), 3.31-3.27 (m, 2H), 2.35-2.07 (m, 1H), 1.95-1.90 (m, 1H), 1.73-1.52 (m, 2H), 1.39 (s, 9H), 1.19 (d, J=6.4 Hz, 3H);
Mass (ESI): m/z 527.4 [M$^+$+1]

Synthesis of tert-butyl 2-((2S, 3R)-1, 3-bis (benzyloxy)-1-oxobutan-2-yl)-1-oxo-2, 5-diazaspiro [3.4] octane-5-carboxylate (2S-K)

To a stirring solution of triphenylphosphine (24.7 g, 94 mmol) in THF (100 mL) was added DIAD (15.3 g, 75 mmol) at RT and stirred for 30 min. To this added compound 2S-J (20 g, 37.9 mmol) in (10 mL) THF slowly and reaction mixture was stirred at RT for 2 h. After consumption of the starting material (by TLC), the reaction was concentrated under reduced pressure. The crude material was purified by silica gel column chromatography eluting 25% EtOAc/n-hexane to afford compound 2S-K (17 g, 88%) as pale yellow thick syrup.
$^1$H-NMR: (400 MHz, DMSO-d$_6$): δ 7.33-7.26 (m, 5H), 7.23-7.18 (m, 5H), 5.10 (s, 2H), 4.80-4.73 (m, 2H), 4.60 (s, 2H), 4.31 (s, 2H), 4.05-4.00 (m, 2H), 1.80-1.68 (m, 4H), 1.39 (s, 9H), 1.18 (d, J=6.0 Hz, 3H);
Mass (ESI): m/z 509.4 [M$^+$+1]

Synthesis of (2S, 3R)-2-(5-(tert-butoxycarbonyl)-1-oxo-2, 5-diazaspiro [3.4] octan-2-yl)-3-hydroxybutanoic acid (2S-L)

To a stirring solution of compound 2S-K (7 g, 13.7 mmol) in methanol (100 mL) was added 10% Pd/C (4 g) at RT and stirred for 6 h under H$_2$ atmosphere. After consumption of the starting material (by TLC), the reaction mixture was filtered through a pad of celite and the pad was washed with methanol (50 mL). Obtained filtrate was concentrated under reduced pressure to obtained crude, which was triturated with n-pentane (50 mL) to afford compound 2S-L (4 g, 88%) as white solid.
$^1$H-NMR: (500 MHz, DMSO-d$_6$): δ 12.80 (br s, 1H), 4.78-4.73 (m, 1H), 4.21-4.19 (m, 1H), 4.09 (s, 2H), 3.55-3.46 (m, 2H), 2.09-2.05 (m, 2H), 1.80 (d, J=7.0 Hz, 1H), 1.38 (s, 9H), 1.35-1.28 (m, 2H), 1.17 (d, J=6.5 Hz, 3H)
LCMS m/z: 329.6 [M$^+$+1]

Synthesis of 2-((tert-butoxycarbonyl) amino) acetic acid (2S-M)

To a stirring solution of glycine (15 g, 200 mmol) in 1,4-dioxane/water (150 mL/75 mL) were added Na$_2$CO$_3$ (53 g, 500 mmol). After added Boc-anhydride (109 mL, 500 mmol) slowly at 0° C. The reaction mixture was stirred at RT for 12 h. After consumption of the starting material (by TLC), the reaction mixture was concentrated under reduced pressure. The crude residue was acidified (pH~4) by using citric acid solution and aqueous layer was extracted with EtOAc (2×150 mL). The combined organic layer was washed with brine solution (2×100 mL). The organic layer was dried over anhydrous Na$_2$SO$_4$, filtered and concentrated under vacuum to afford compound 2S-M (30 g, 85.7%) as white solid. This material was directly used for the next step without further purification.
$^1$H-NMR: (500 MHz, DMSO-d$_6$): δ 12.41 (br s, 1H), 7.04 (t, J=5.5 Hz, 1H), 3.57 (d, J=5.5 Hz, 2H), 1.37 (s, 9H);

Synthesis of tert-butyl (2-amino-2-oxoethyl) carbamate (2S-N)

To a stirring solution of 2S-M (10 g, 57.14 mmol) in CH$_2$Cl$_2$ (100 mL) were added HOBt (15.43 g, 114 mmol), EDCI.HCl (21.8 g, 114 mmol) followed by NH$_4$Cl (4.54 g, 85.71 mmol) and DIPEA (30.7 mL, 171 mmol) at 0° C. The reaction mixture was stirred at RT for 16 h. After consumption of the starting material (by TLC), the reaction mixture was washed with water (2×100 mL). Organic layer was dried over anhydrous Na$_2$SO$_4$ and concentrated under reduced pressure to give crude; which was purified by silica gel column chromatography eluting with 2% MeOH/CH$_2$Cl$_2$. After compound was triturated with ether (25 mL) and the precipitated solid was filtered to afford 2S-N (2 g, 20%) as white solid.
$^1$H-NMR: (500 MHz, DMSO-d$_6$): δ 7.52 (br s, 1H), 7.17 (br s, 1H), 3.46 (d, J=6.5 Hz, 2H), 1.38 (s, 9H);

Synthesis of (E)-tert-butyl (2-(((dimethylamino) methylene) amino)-2-oxoethyl) carbamate (2S-O)

To a stirring solution of 2S-N (7 g, 40.22 mmol) in THF (70 mL) was added DMF.DMA (10.7 mL, 80.44 mmol) at RT and heated to 80° C. for 2 h. After consumption of the starting material (by TLC), the reaction mixture was concentrated under reduced pressure to afford 2S-O (9 g, crude) as brown syrup. This crude material was directly taken for the next step without further purification.
$^1$H-NMR: (500 MHz, DMSO-d$_6$): δ 6.72 (br s, 1H), 4.35 (s, 1H), 3.64 (d, J=5.5 Hz, 2H), 3.09 (s, 1H), 1.42 (s, 9H);
Mass (ESI): m/z 230.2 [M$^+$+1];

Synthesis of tert-butyl ((1, 2, 4-oxadiazol-5-yl) methyl) carbamate (2S-P)

To a stirring solution of 2S-O (9 g (crude), 39.30 mmol) in ethanol (80 mL) was added hydroxylamine hydrochloride (5.45 g, 78.60 mmol) under N$_2$ atmosphere. The reaction mixture was heated to 90° C. and stirred for 2 h. After consumption of the starting material (by TLC) evaporated solvent under reduced pressure and crude residue was diluted with water (75 mL). The aqueous layer was extracted by DCM (3×100 mL). The combined organic layer was washed by brine solution (1×100 mL). The organic layer was dried over anhydrous Na$_2$SO$_4$ and solvent was concentrated under reduced pressure to give crude; which was purified by

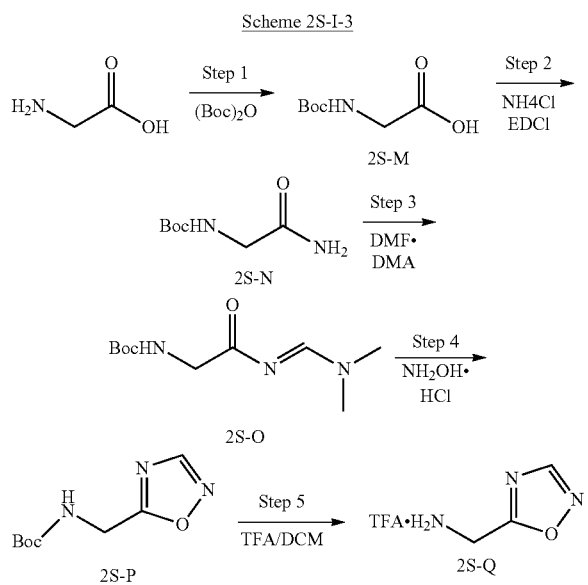

Scheme 2S-I-3 silica gel column chromatography eluting with 25% EtOAc/hexane to afford 2S-P (4 g, 51%).
$^1$H-NMR: (500 MHz, DMSO-d$_6$): δ 8.90 (s, 1H), 7.64 (s, 1H), 4.44 (s, 2H), 1.39 (s, 9H);
LCMS m/z: 198.4 [M$^-$−1]

Synthesis of (1, 2, 4-oxadiazol-5-yl) methanamine (2S-Q)

To a stirring solution of 2S-P (1.1 g, 5.52 mmol) in DCM (30 mL) was added trifluoroacetic acid (2.1 mL, 27.63 mmol) at 0° C. for 30 min. The reaction mixture was stirred at RT for 4 h. After consumption of the starting material (by TLC), the reaction mixture was concentrated under vacuum. The crude residue was triturated with ether (20 mL) to afford 2S-Q (850 mg, 72.6%) as white solid.
$^1$H-NMR: (400 MHz, DMSO-d$_6$): δ 9.13 (s, 1H), 8.90 (br s, 2H), 4.56 (s, 2H);
LCMS (ESI): 100.4 [M$^+$+1]

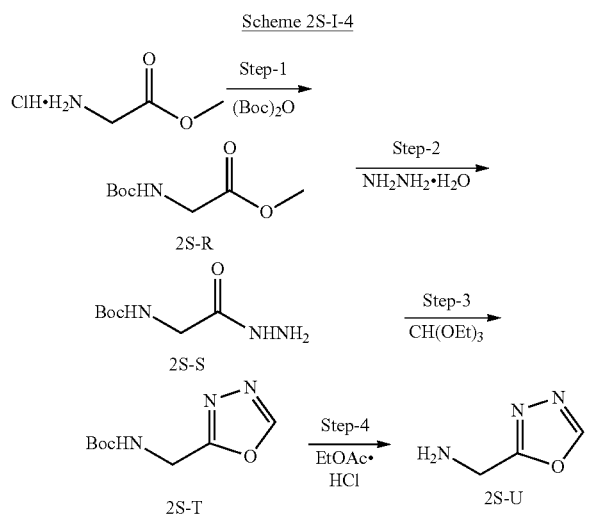

Synthesis of methyl (tert-butoxycarbonyl) glycinate (2S-R)

To a stirring solution of glycine methyl ester hydrochloride (50 g, 400 mmol) in 1,4 dioxane/water (300 mL/200 mL) were added Na$_2$CO$_3$ (84.8 g, 800 mmol) and stirred at RT for 10 min. The reaction mixture was cooled to 0° C. and Boc-anhydride (104 mL, 480 mmol) was added drop wise and the stirring was continued at RT for 16 h. After consumption of the starting material (by TLC), the reaction mixture was concentrated under reduced pressure and obtained residue was diluted with water (100 mL) and extracted with EtOAc (2×250 mL). The combined organic layer was washed with brine (1×200 mL) and organic layer was dried over anhydrous Na$_2$SO$_4$, filtered and concentrated under reduced pressure to afford 2S-R (64 g, 84%) as thick syrup.
$^1$H-NMR: (500 MHz, DMSO-d$_6$): δ 7.19 (t, J=5.5 Hz, 1H), 3.67 (d, J=6.0 Hz, 2H), 3.62 (s, 3H), 1.38 (s, 9H);
LCMS m/z: 190.2 [M$^+$+1]

Synthesis of tert-butyl (2-hydrazinyl-2-oxoethyl) carbamate (2S-S)

A solution of 2S-R (20 g, 105 mmol) in EtOH (100 mL) was added hydrazine hydrate (15.8 g, 315 mmol) at RT and after stirred at 100° C. for 6 h. After consumption of the starting material (by TLC), ethanol was evaporated under reduced pressure. Obtained crude material was triturated with n-pentane/diethyl ether (20 mL/20 mL) to afford 2S-S as white solid.
$^1$H-NMR: (400 MHz, DMSO-d$_6$): δ 8.91 (s, 1H), 6.88 (t, J=5.5 Hz, 1H), 4.16 (s, 2H), 3.47 (d, J=6.0 Hz, 2H), 1.37 (s, 9H);
LCMS m/z: 190.2 [M$^+$+1]

Synthesis of tert-butyl ((1, 3, 4-oxadiazol-2-yl) methyl) carbamate (2S-T)

A solution of 2S-S (14 g, 74 mmol) in triethyl orthoformate (140 mL) was added p-TSA (catalytic, 140 mg) at RT and after stirred at 80° C. for 4 h. After consumption of starting material (by TLC), triethyl orthoformate was evaporated under reduced pressure. The crude residue was purified by column chromatography eluting 20% EtOAc/hexane to afford 2S-T (6.1 g, 41.5%) as an off-white solid.
$^1$H-NMR: (400 MHz, DMSO-d$_6$): δ 10.74 (s, 1H), 7.45 (s, 1H), 4.03 (s, 2H), 1.47 (s, 9H); LCMS m/z: 200.2 [M$^+$+1]

Synthesis of (1, 3, 4-oxadiazol-2-yl) methanamine (2S-U)

To a stirring solution of 2S-T (5 g, 25 mmol) in EtOAc (10 mL) was added EtOAc saturated with HCl (60 mL) at 0° C. and stirred at RT for 16 h. After consumption of the starting material (by TLC), the reaction mixture was concentrated under reduced pressure. The crude material was triturated with diethylether/n-pentane (25 mL/25 mL) and dried under reduced pressure to afford 2S-U (3 g, 88.7%) as an off-white solid (HCl salt).
$^1$H-NMR: (500 MHz, DMSO-d$_6$): δ 9.55 (br s, 2H), 7.99 (s, 1H), 3.90 (s, 2H);
LCMS m/z: 100 [M$^+$+1]

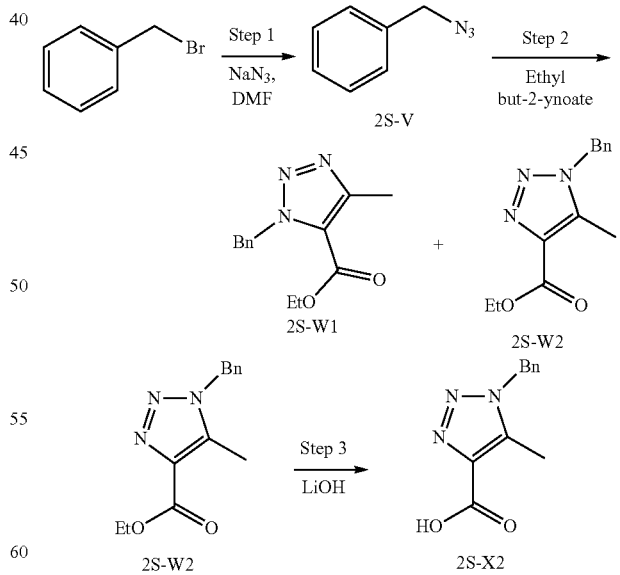

Synthesis of (azidomethyl) benzene (2S-V)

To a stirring solution of benzyl bromide (30 g, 175 mmol) in dimethyl formamide (300 mL) was added sodium azide (45.6 g, 701 mmol) at RT under inert atmosphere. The resultant reaction mixture was stirred at 70° C. for 16 h. After completion of reaction monitored (by TLC), the reaction mixture was allowed to RT; the volatiles were diluted with water (300 mL) and ether (200 mL). The separated organic layer was washed by (3×200 mL) of chilled water. The separated organic layer was dried over anhydrous $Na_2SO_4$, filtered and concentrated under reduced pressure to afford compound 2S-V (18 g, crude) as an off-white solid.
$^1$H-NMR: (400 MHz, $CDCl_3$): δ 7.40-7.29 (m, 5H), 4.32 (s, 2H).

Synthesis of ethyl 1-benzyl-5-methyl-1H-1, 2, 3-triazole-4-carboxylate (2S-W2)

To a stirring solution of ethyl but-2-ynoate (8.0 g, 71.3 mmol) in toluene (80 mL) was added 2S-V (12.0 g, 107 mmol) at RT under inert atmosphere. The resultant reaction mixture was heated to 100° C. and stirred for 16 h. The reaction mixture was allowed to RT; the volatiles were evaporated under reduced pressure to which, crude residue was purified by column chromatography by eluting 40% EtOAc/hexane to afford 2S-W1 and 2S-W2 (8.2 g, 47.1%) (separable by column chromatography)
$^1$H-NMR: (400 MHz, $CDCl_3$): δ 7.36-7.31 (m, 3H), 7.16 (t, J=6.0 Hz, 2H), 5.53 (s, 2H), 4.43 (q, J=7.2 Hz, 2H), 2.45 (s, 3H), 1.41 (t, J=7.2 Hz, 3H);
Mass m/z: 246.3 [$M^+$+1]

Synthesis of 1-benzyl-5-methyl-1H-1, 2, 3-triazole-4-carboxylic acid (2S-X2)

To a stirring solution of compound 2S-W2 (8.2 g, 33.4 mmol) in $THF/H_2O$ (82 mL/82 mL, 1:1) was added $LiOH.H_2O$ (4.2 g, 0.4 mmol) at RT and stirred for 16 h. After completion of reaction (by TLC), the volatiles were evaporated under reduced pressure. The residue was acidified with aqueous 2N HCl and the precipitated solid was filtered and washed with water (25 mL), dried under reduced pressure to afford compound 2S-X2 (7.0 g, 96.6%) as an off-white solid.
$^1$H-NMR: (400 MHz, DMSO-$d_6$): δ 13.01 (br s, 1H), 7.40-7.32 (m, 5H), 5.63 (s, 2H), 2.45 (s, 3H);
Mass m/z: 218.3 [$M^+$+1];

Scheme 2S-I-6

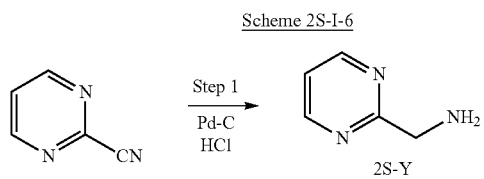 [SMILES: N#Cc1ncccn1 ; NCc1ncccn1]

Synthesis of pyrimidin-2-ylmethanamine (2S-Y)

To a stirring solution of 2-cyanopyrimidine (2.0 g, 19.0 mmol) in methanol (50 mL) were added 10% Pd/C (300 mg), 12 N HCl (1.5 mL) under $N_2$ atmosphere. The reaction mixture was stirred under $H_2$ atmosphere (balloon pressure) at RT for 3 h. After consumption of the starting material (by TLC), the reaction mixture was filtered through a pad of celite and the pad was washed with methanol. Obtained filtrate was concentrated under reduced pressure to afford crude compound which was triturated with diethyl ether to obtained compound 2S-Y (1.2 g, 44%) as white solid.

$^1$H-NMR: (500 MHz, DMSO-$d_6$): δ 8.87 (d, J=5.0 Hz, 2H), 8.69 (br s, 2H), 7.52 (t, J=5.0 Hz, 1H), 4.24 (s, 2H); Mass (ESI): 110.3 [$M^+$+1]

Scheme 2S-I-7

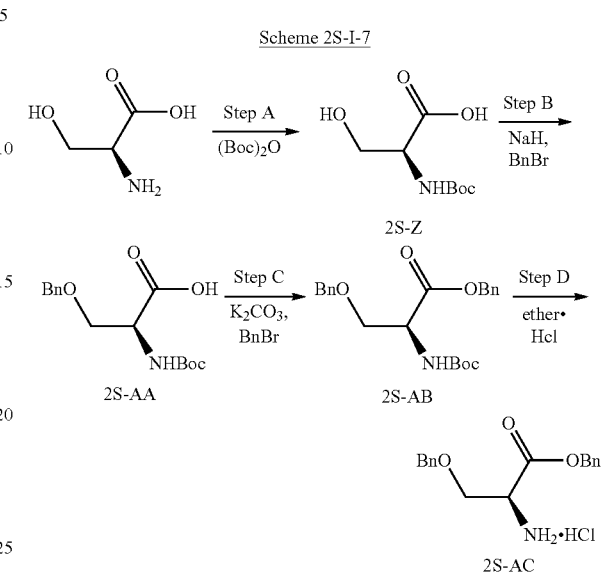

Synthesis of (S)-2-((tert-butoxycarbonyl) amino)-3-hydroxypropanoic acid (2S-Z)

To a stirring solution of L-serine (76 g, 723 mmol) in 1, 4 dioxane/$H_2O$ (350 mL/300 mL) were added NaOH (61 g, 1.51 mol), Boc-anhydride (190 mL, 868 mmol) at 0° C. The reaction mixture was stirred at RT for 16 h. After consumption of the starting material (by TLC), the reaction mixture was acidified with 2N HCl (pH~4) and extracted with EtOAc (5×500 mL). The combined organic extracts were dried over anhydrous $Na_2SO_4$ and concentrated under reduced pressure to afford 2S-Z (100 g, 67.5%) as yellow syrup.
$^1$H-NMR: (400 MHz, $CDCl_3$): δ 6.54 (br s, 1H), 5.77 (br s, 1H), 4.35-4.04 (m, 1H), 3.87-3.84 (m, 2H), 1.45 (s, 9H).

Synthesis of (S)-3-(benzyloxy)-2-((tert-butoxycarbonyl) amino) propanoic acid (2S-AA)

To a stirring solution of 2S-Z (50 g, 245 mmol) in DMF (650 mL) was added NaH (60%) (23 g, 563 mmol) at −15° C. and stirred for 2 h. Benzyl bromide (32.8 mL, 269 mmol) was slowly added. The reaction mixture temperature was warmed to RT and stirred for 12 h. After consumption of the starting material (by TLC), the reaction mixture was poured into chilled water (200 mL) and extracted with diethylether (2×250 mL). The aqueous layer was acidified with citric acid (pH~4) and extracted with EtOAc (2×500 mL). The combined organic layers were washed with water (3×250 mL). The organic extracts were dried over anhydrous $Na_2SO_4$, filtered and concentrated under reduced pressure to afford 2S-AA (54 g, 75%) as brown syrup.
$^1$H-NMR: (400 MHz, $CDCl_3$): δ 7.32-7.26 (m, 5H), 5.43 (d, J=7.6 Hz, 1H), 4.70-4.46 (m, 1H), 4.45 (s, 2H), 4.13-3.91 (m, 1H), 3.73-3.70 (m, 1H), 1.44 (s, 9H).

Synthesis of (S)-benzyl 3-(benzyloxy)-2-((tert-butoxycarbonyl) amino) propanoate (2S-AB)

To a stirring solution of 2S-AA (36 g, 122 mmol) in DMF (250 mL) was added $Na_2CO_3$ (20 g, 183 mmol) at 0° C. and added benzyl bromide (18 mL, 146 mmol) slowly. The reaction mixture temperature was warmed to RT and stirred for 12 h. After consumption of the starting material (by TLC), the reaction mixture was poured into chilled water (200 mL) and extracted with diethylether (2×250 mL). The combined organic layers were washed with water (3×250 mL). The organic extracts were dried over anhydrous $Na_2SO_4$, filtered and concentrated under reduced pressure to afford 2S-AB (42 g, 91%) as brown syrup was used directly for next step without any purification.

Synthesis of (S)-benzyl 2-amino-3-(benzyloxy) propanoate hydrochloride (2S-AC)

To a stirring solution of 2S-AB (10 g, 25.9 mmol) in ether saturated with HCl (50 mL) was added at 0° C. and stirred at RT for 12 h. The obtained precipitate was filtered and triturated with diethylether (2×100 mL). The filtered compound was dried under vacuum to afford 2S-AC (5 g, 60%) as white solid.

$^1$H-NMR: (400 MHz, DMSO-$d_6$): δ 8.66 (s, 2H), 7.38-7.27 (m, 10H), 5.29-5.22 (m, 2H), 4.57-4.44 (m, 3H), 3.91-3.81 (m, 2H)

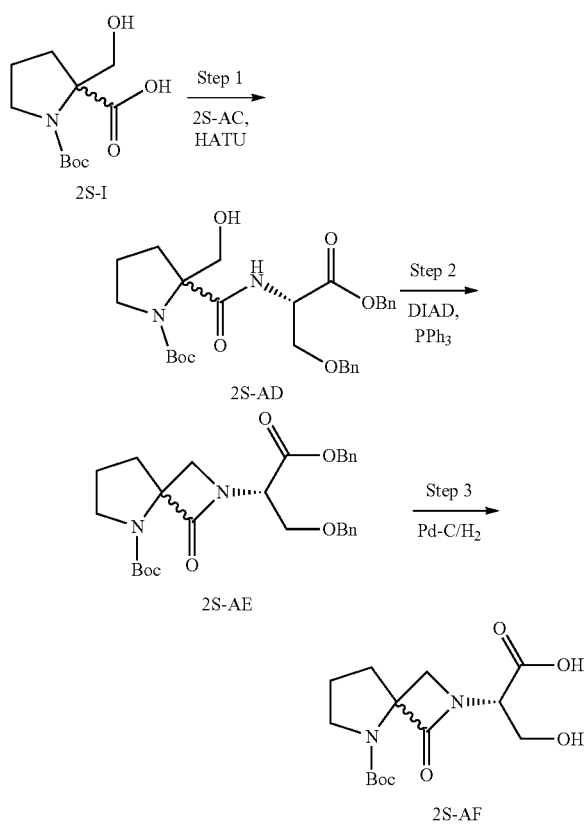

Scheme 2S-I-8

Synthesis of tert-butyl 2-(((S)-1, 3-bis (benzyloxy)-1-oxopropan-2-yl) carbamoyl)-2-(hydroxymethyl) pyrrolidine-1-carboxylate (2S-AD)

To a stirring solution of compound 2S-I (5 g, 20.4 mmol) in $CH_2Cl_2$ (50 mL) were added DIPEA (10.7 mL, 61.2 mmol), 2S-AC (5.8 g, 20.4 mmol), HATU (11.6 g, 30.6 mmol) at 0° C. and stirred to RT for 12 h. After consumption of the starting material (by TLC), the reaction mixture was diluted with water (100 mL) and extracted with $CH_2Cl_2$ (2×100 mL). The combined organic layer was washed with citric acid (1×100 mL) followed by brine solution (1×100 mL). The organic layer was dried over anhydrous $Na_2SO_4$, filtered and concentrated under reduced pressure. Obtained crude material was purified by silica gel column chromatography eluting with 50% EtOAc/n-hexane to afford compound 2S-AD (8 g, 76.5%) as yellow thick syrup.

$^1$H-NMR: (400 MHz, $CD_3OD$): δ 7.33-7.24 (m, 10H), 5.23-5.11 (m, 2H), 4.72-4.66 (m, 2H), 4.50-4.44 (m, 1H), 4.18-3.91 (m, 2H), 3.75-3.70 (m, 2H), 3.65-3.40 (m, 2H), 2.34-2.03 (m, 2H), 1.81-1.78 (m, 2H), 1.41 (s, 9H);

Mass (ESI): m/z 512.6 [$M^+$+1]

Synthesis of tert-butyl 2-((S)-1, 3-bis (benzyloxy)-1-oxopropan-2-yl)-1-oxo-2, 5-diazaspiro [3.4] octane-5-carboxylate (2S-AE)

To a stirring solution of triphenylphosphine (640 mg, 2.44 mmol) in THF (5 mL) was added DIAD (392 mg, 1.94 mmol) at RT and stirred for 15 min, then compound 2S-AD (500 mg, 0.97 mmol) in (5 mL) THF was slowly added and reaction mixture was stirred at RT for 2 h. After consumption of the starting material (by TLC), the reaction was concentrated under reduced pressure. The crude material was purified by column chromatography by eluting 2% MeOH/DCM to afford compound 2S-AE (450 mg, 93%) as yellow liquid.

$^1$H-NMR: (400 MHz, $CD_3OD$): δ 7.34-7.27 (m, 10H), 5.25-5.14 (m, 2H), 4.78-4.73 (m, 1H), 4.70-4.42 (m, 2H), 4.04-3.98 (m, 1H), 3.93-3.78 (m, 1H), 3.89-3.78 (m, 1H), 3.76-3.68 (m, 1H), 3.45-3.35 (m, 2H), 2.20-2.09 (m, 2H), 1.90-1.78 (m, 2H), 1.46 (s, 9H)

LCMS (ESI): m/z 495.5 [$M^+$+1]

Synthesis of 1-(tert-butoxycarbonyl)-2-(hydroxymethyl) pyrrolidine-2-carboxylic acid (2S-AF)

To a stirring solution of compound 2S-AE (500 mg, 1.01 mmol) in methanol (25 mL) was added 50% wet 10% Pd/C (250 mg) at RT and stirred for 24 h under $H_2$ atmosphere. After consumption of the starting material (by TLC), the reaction mixture was filtered through a pad of celite and the pad was washed with methanol (20 mL). Obtained filtrate was concentrated under reduced pressure to afford compound 2S-AF (400 mg, crude) as white solid.

$^1$H-NMR: (400 MHz, $CD_3OD$): δ 4.92-4.87 (m, 1H), 4.28-4.07 (m, 3H), 3.63-3.60 (m, 1H), 3.55-3.40 (m, 2H), 2.30-2.25 (m, 2H), 1.95-1.87 (m, 2H), 1.47 (s, 9H);

LCMS: 315.3 [M+1]

Scheme 2S-I-9

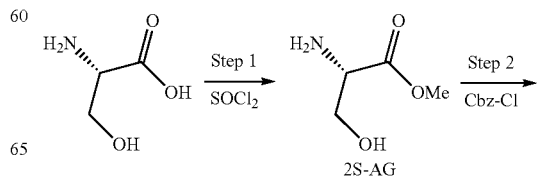

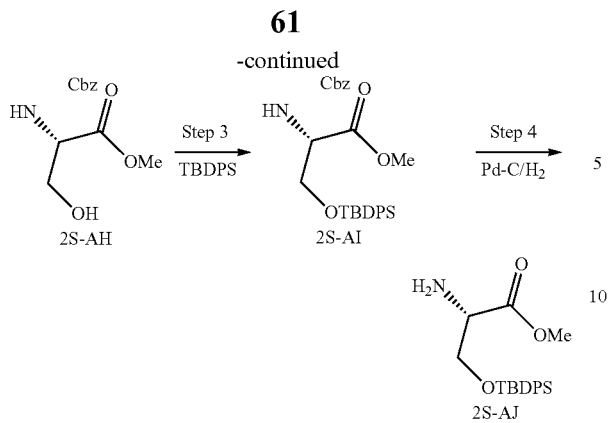

Synthesis of (S)-methyl 2-amino-3-hydroxypropanoate (2S-AG)

To a stirring solution of L-serine (40 g, 0.38 mol) in methanol (300 mL) was added $SOCl_2$ (33.6 mL, 0.45 mol) drop wise at 0° C. and stirred for 1 h. The resulting reaction mixture was refluxed for 24 h. After consumption of the starting material (by TLC), the reaction mixture was warmed to RT and concentrated under vacuum and decanted with n-hexane (2×200 mL) to afford compound 2S-AG (59.18 g, crude).

$^1$H-NMR: (400 MHz, DMSO-$d_6$): δ 8.62 (s, 3H), 4.08 (d, J=3.2 Hz, 1H), 3.83 (d, J=3.6 Hz, 2H), 3.78 (s, 3H);
LCMS, m/z: 120.2 [M$^+$–1]

Synthesis of (S)-methyl 2-(((benzyloxy)carbonyl)amino)-3-hydroxypropanoate (2S-AH)

To a stirring solution of compound 2S-AG (40 g, 0.33 mol) in 1,4-dioxane (300 mL) and water (100 mL) was added $Na_2CO_3$ (71.18 g, 0.67 mol) and stirred at RT for 30 min. The reaction mixture was cooled to 0° C., benzyl chloroformate (68.5 g, 0.40 mol) was added drop wise and the stirring was continued at RT for 8 h. After consumption of the starting material (by TLC), the reaction mixture was diluted with EtOAc (200 mL). The aqueous layer was extracted with EtOAc (2×200 mL). The separated organic extracts were washed with brine, dried over anhydrous $Na_2SO_4$, filtered and concentrated under reduced pressure. The crude material was purified by silica gel column chromatography eluting with 20% EtOAc/n-hexane to afford compound 2S-AH (53 g, 62%);

$^1$H-NMR: (400 MHz, DMSO-$d_6$): δ 7.49 (d, J=8 Hz, 1H), 7.37-7.29 (m, 5H), 5.04 (s, 2H), 4.93 (t, J=6 Hz, 1H), 4.18-4.13 (m, 1H), 3.78 (s, 3H), 3.67-3.56 (m, 2H)

Synthesis of (S)-methyl 2-(((benzyloxy)carbonyl)amino)-3-((tert-butyldiphenylsilyl)oxy) propanoate (2S-AI)

To a stirring solution of compound 2S-AH (20 g, 79.20 mmol) in DCM (700 mL) was added imidazole (16 g, 237.6 mmol) at 0° C. followed by TBDPS (25.9 g, 95.04 mmol) under $N_2$ atmosphere and stirred at RT for 8 h. After consumption of the starting material (by TLC), the reaction mixture was diluted with water (100 mL) and the aqueous layer was extracted with DCM (2×200 mL). The separated organic layer was washed with brine, dried over anhydrous $Na_2SO_4$ and concentrated under reduced pressure. The crude material was purified by silica gel column chromatography eluting with 20% EtOAc/n-hexane to afford compound 2S-AI (25 g, 64%).

$^1$H-NMR: (500 MHz, CDCl$_3$): δ 7.23-7.68 (m, 1H), 7.58 (d, J=7 Hz, 3H), 7.44-7.37 (m, 9H), 7.34 (d, J=7.5 Hz, 2H), 5.65 (d, J=9 Hz, 1H), 5.12 (d, J=2, 2H), 4.45 (d, J=9 Hz, 1H), 4.10-4.07 (m, 1H), 3.91-3.88 (m, 1H), 3.74 (s, 3H), 1.04 (s, 9H);
LCMS (m/z): 492.1 [M$^+$–1]

Synthesis of (S)-methyl 2-amino-3-((tert-butyldiphenylsilyl)oxy)propanoate (2S-AJ)

To a stirring solution of compound 2S-AI (25 g, 51.12 mmol) in ethanol (250 mL) was added 50% wet 10% Pd/C (15 g) at RT and stirred for 8 h under $H_2$ atmosphere (balloon pressure). After consumption of the starting material (by TLC), the reaction mixture was filtered through a pad of celite and the pad was washed with ethanol. Obtained filtrate was concentrated under reduced pressure to afford compound 2S-AJ (18 g, 97%) as yellow liquid.

$^1$H-NMR: (400 MHz, CDCl$_3$): δ 7.66-7.61 (m, 4H), 7.43-7.36 (m, 6H), 4.00-3.97 (m, 2H), 3.74 (s, 3H), 3.64 (t, J=4 Hz, 1H), 2.65 (s, 2H), 1.04 (s, 9H);
LCMS m/z: 358 [M$^+$–1]

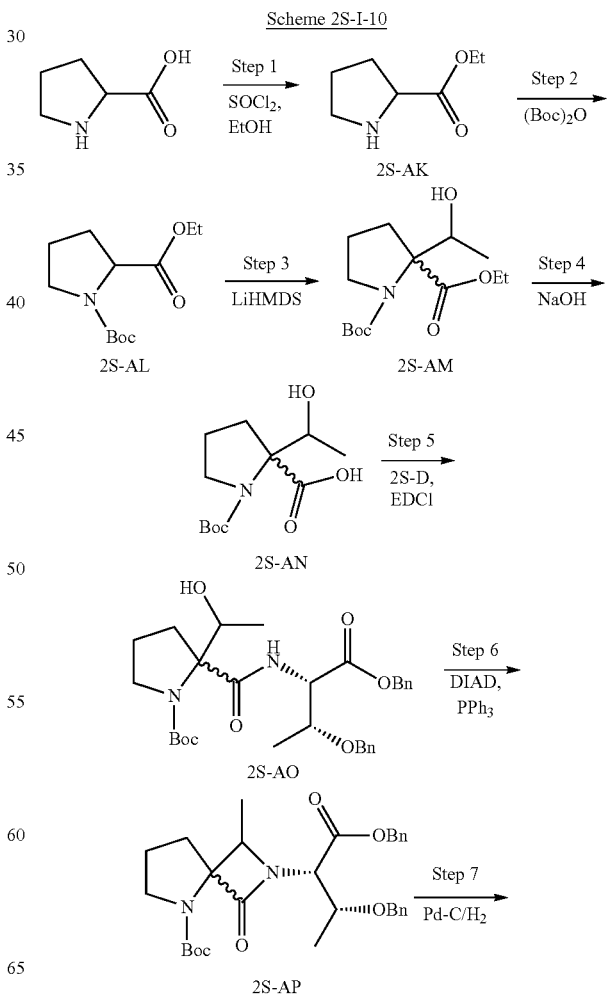

Scheme 2S-I-10

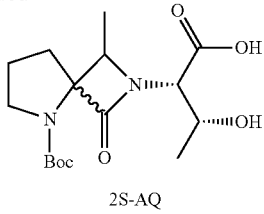

2S-AQ

Synthesis of ethyl pyrrolidine-2-carboxylate hydrochloride (2S-AK)

To a stirring solution of L-proline (110 g, 956.5 mmol) in ethanol was added thionyl chloride (141 ml, 1911.3 mmol) and refluxed for 16 h. The reaction mixture was brought to RT and concentrated under vacuum to afford compound 2S-AK as the hydrochloride salt (170 g, 99%).

$^1$H-NMR: (400 MHz, CDCl$_3$): δ 4.15-4.10 (m, 2H), 3.68-3.62 (m, 2H), 3.59-3.47 (m, 2H), 2.49-2.37 (m, 1H), 2.27-2.05 (m, 3H), 1.18 (t, J=3.6 Hz, 3H);
LCMS, m/z: 143 [M$^+$+1]

Synthesis of 1-tert-butyl 2-ethyl pyrrolidine-1, 2-dicarboxylate (2S-AL)

To a stirring solution of compound 2S-AK (70 g, 0.391 mol) in CH$_2$Cl$_2$ (700 mL) were added Et$_3$N (170.7 mL, 1.22 mol) followed by Boc-anhydride (133 g, 0.61 mol) at 0° C. The reaction mixture was stirred at RT for 12 h. After consumption of the starting material (by TLC), the reaction was diluted with water (100 mL) and extracted with CH$_2$Cl$_2$ (2×200 mL). The organic layer was washed with water (1×150 mL), brine (1×200 mL), dried over Na$_2$SO$_4$ and concentrated under reduced pressure to afford compound 2S-AL (90 g, 90%) as thick syrup.

$^1$H-NMR: (400 MHz, DMSO-d$_6$): δ 4.15-4.10 (m, 2H), 4.09-4.02 (m, 1H), 3.36-3.29 (m, 2H), 2.25-2.13 (m, 1H), 1.87-1.76 (m, 3H), 1.40 (s, 9H), 1.18 (t, J=3.6 Hz, 3H);
LCMS, m/z: 144 [(M$^+$+1)-Boc];
HPLC: 96.11%

Synthesis of 1-tert-butyl 2-ethyl 2-(1-hydroxyethyl) pyrrolidine-1, 2-dicarboxylate (2S-AM)

To a stirring solution of compound 2S-AL (5 g, 20.5 mmol) in THF (50 mL) was added LiHMDS (20.3 mL, 20.5 mmol) at −20° C. and stirred for 1 h. To this acetaldehyde (1.2 mL, 20.5 mmol) was added dropwise at −20° C. and stirred for 1 h at −20° C. After consumption of the starting material (by TLC), the reaction was quenched with aqueous NH$_4$Cl solution and extracted with EtOAc (1×50 mL). The separated organic layer was dried over Na$_2$SO$_4$ and concentrated to afford crude compound was purified by column chromatography eluting 10% EtOAc/hexane to afford compound 2S-AM (1.8 g, 30%) as pale yellow syrup.

$^1$H-NMR: (500 MHz, DMSO-d$_6$): δ 5.10 (d, J=8.5 Hz, 1H), 4.54-4.36 (m, 2H), 4.05-3.99 (m, 2H), 3.60-3.49 (m, 1H), 1.97-1.74 (m, 4H), 1.40 (s, 9H), 1.18, 1.15 (dd, J=7.5 Hz, 6.5 Hz, 3H), 0.96 (d, J=9.5 Hz, 3H);
LCMS, m/z: 188 [(M$^+$+1)-Boc]

Synthesis of 1-(tert-butoxycarbonyl)-2-(1-hydroxyethyl) pyrrolidine-2-carboxylic acid (2S-AN)

To a stirring solution of compound 2S-AM (10 g, 34.8 mmol) in methanol (30 mL) were added NaOH (2.7 g, 69.6 mmol), H$_2$O/THF (30 mL/30 mL)) at 0° C. The reaction mixture was heated to 80° C. for 5 h. After consumption of the starting material (by TLC), the solvent was evaporated under reduced pressure. The aqueous layer was acidified using citric acid solution and extracted with EtOAc (2×100 mL). The separated organic layer was washed with water (1×50 mL), dried over Na$_2$SO$_4$ and concentrated to afford compound 2S-AN (4.8 g, 53.3%) as brown sticky solid.

$^1$H-NMR: (500 MHz, DMSO-d$_6$): δ 4.60-4.54 (m, 1H), 3.98 (d, J=10.0 Hz, 1H), 3.90-3.77 (m, 2H), 3.44-3.34 (m, 1H), 2.01-1.68 (m, 4H), 1.40 (s, 9H), 1.26 (d, J=10.0 Hz, 3H);
LCMS, m/z: 258 (M$^+$−1);
HPLC (purity): 91.7%

Synthesis of tert-butyl 2-(((2S,3R)-1,3-bis(benzyloxy)-1-oxobutan-2-yl)carbamoyl)-2-(1-hydroxyethyl)pyrrolidine-1-carboxylate (2S-AO)

To a stirring solution of compound 2S-AN (2.0 g, 7.72 mmol) in CH$_2$Cl$_2$ (50 mL) were added DIPEA (4.2 mL, 22.4 mmol), EDCI.HCl (2.2 g, 11.5 mmol) followed by HOBt (1.5 g, 11.5 mmol), compound D (2.8 g, 8.35 mmol) at 0° C. and stirred for 12 h. After consumption of the starting material (by TLC), the reaction mixture was diluted with water (30 mL) and extracted with CH$_2$Cl$_2$ (2×50 mL). The combined organic layer was washed with brine (2×50 mL), dried over anhydrous Na$_2$SO$_4$, filtered and concentrated under reduced pressure. Obtained crude material was purified by silica gel column chromatography eluting 25% EtOAc/n-hexane to afford compound 2S-AO (1.5 g, 36%) as colorless liquid.

$^1$H-NMR: (400 MHz, DMSO-d$_6$): δ 8.47 (t, J=8.8 Hz, 1H), 7.31-7.19 (m, 10H), 5.73-5.58 (m, 1H), 5.18 (s, 2H), 4.64 (s, 2H), 4.60-4.49 (m, 1H), 4.29 (d, J=12.0 Hz, 1H), 4.15-4.12 (m, 1H), 3.59-3.59 (m, 1H), 3.24-3.13 (m, 1H), 1.71-1.60 (m, 2H), 1.43-1.38 (m, 2H), 1.35 (s, 9H), 1.18 (d, J=6.0 Hz, 3H), 1.04 (d, J=6.4 Hz, 31-1);
Mass (ESI): m/z 540 [M$^-$−1]

Synthesis of tert-butyl 2-((2S,3R)-1,3-bis(benzyloxy)-1-oxobutan-2-yl)-1-methyl-3-oxo-2,5-diazaspiro[3.4]octane-5-carboxylate (2S-AP)

To a stirring solution of triphenylphosphine (1.45 g, 5.53 mmol) in THF (30 mL) was added DIAD (1.12 g, 5.53 mmol) at RT and stirred for 30 min. To this added compound 2S-AO (1.5 g, 2.77 mmol) in (10 mL) THF slowly and reaction mixture was stirred at RT for 2 h. After consumption of the starting material (by TLC), the reaction was concentrated under reduced pressure. The crude material was purified by silica gel column chromatography eluting 20% EtOAc/hexane to afford compound 2S-AP (800 mg, 57%) as pale yellow syrup.

$^1$H-NMR: (400 MHz, DMSO-d$_6$): δ 7.33-7.18 (m, 10H), 5.07 (s, 2H), 4.61 (s, 2H), 4.38-4.31 (m, 1H), 3.77-3.75 (m, 1H), 3.28-3.24 (m, 1H), 2.67-2.66 (m, 1H), 2.22-2.12 (m, 1H), 1.98-1.92 (m, 3H), 1.72-1.60 (m, 1H), 1.40 (s, 9H), 1.18 (d, J=5.6 Hz, 3H), 1.13 (d, J=6.4 Hz, 3H)
Mass (ESI): m/z 523 [M$^+$+1]

Synthesis of (2S,3R)-2-(5-(tert-butoxycarbonyl)-1-methyl-3-oxo-2,5-diazaspiro[3.4]octan-2-yl)-3-hydroxybutanoic acid (2S-AQ)

To a stirring solution of compound 2S-AP (900 mg) in methanol (30 mL) was added 10% Pd/C (300 mg) at RT and stirred for 16 h under H₂ atmosphere (balloon pressure). After consumption of the starting material (by TLC), the reaction mixture was filtered through a pad of celite and washed with methanol (10 mL). Obtained filtrate was concentrated under reduced pressure to afford compound 2S-AQ (480 mg, 82%) as yellow thick syrup.

¹H-NMR: (400 MHz, DMSO-d₆): δ12.80 (br s, 1H), 5.11-4.96 (m, 1H), 4.83-4.04 (m, 3H), 3.40-3.35 (m, 1H), 2.11 (s, 3H), 2.10-2.03 (m, 2H), 1.46 (s, 9H), 1.43-1.39 (m, 6H).

LCMS: 342 [M⁻−1]

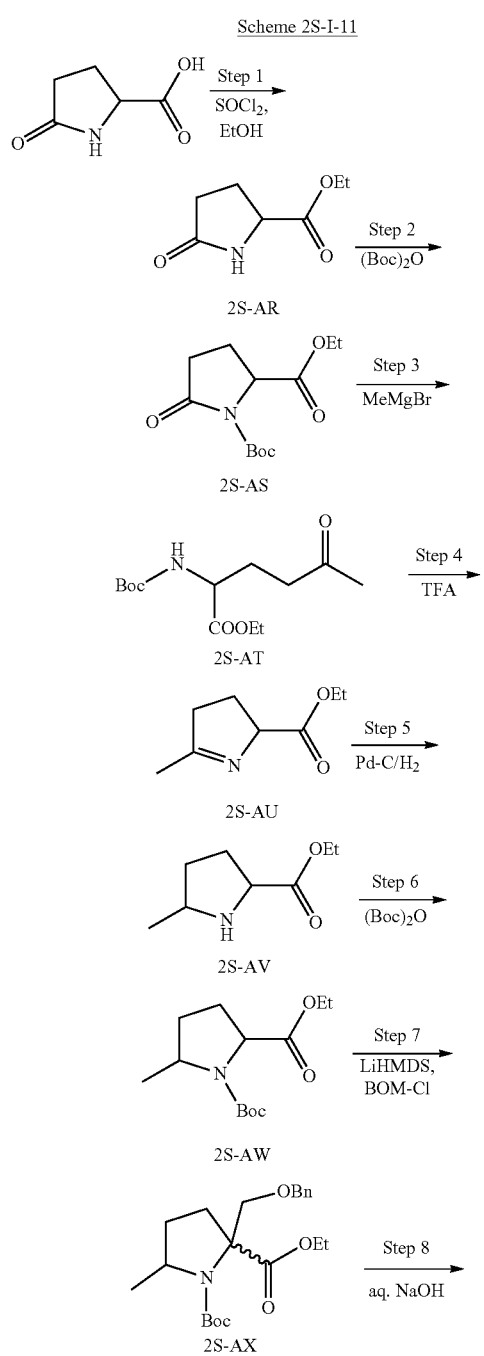

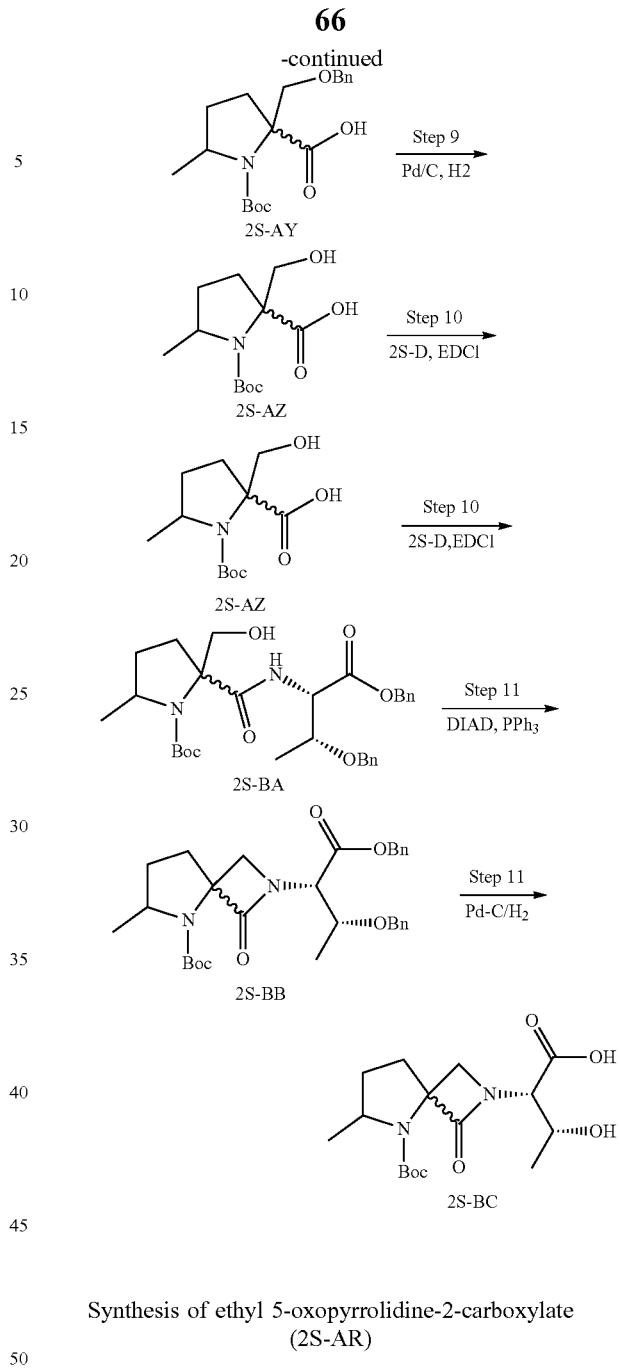

Synthesis of ethyl 5-oxopyrrolidine-2-carboxylate (2S-AR)

To a stirring solution of 5-oxopyrrolidine-2-carboxylic acid (10 g, 77.4 mmol) in ethanol (100 mL) was added thionyl chloride (6.7 mL, 92.9 mmol) at 0° C. The reaction mixture was stirred at RT for 16 h. After consumption of the starting material (by TLC), the solvents from the reaction mixture were removed under vacuum. The residue was diluted with EtOAc (50 mL) and stirred over K₂CO₃. The organic layer was dried over anhydrous Na₂SO₄ and concentrated under reduced pressure. Obtained crude material was purified by silica gel column chromatography to afford compound 2S-AR (9 g, 74%).

¹H-NMR: (400 MHz, DMSO-d₆): δ 7.98 (br s, 1H), 4.16 (t, 3H), 2.37-2.30 (m, 1H), 2.15 (q, 2H), 2.03-1.97 (m, 1H), 1.22 (t, 3H);

LCMS, m/z: 157.9 [M⁺+1]

Synthesis of 1-tert-butyl 2-ethyl 5-oxopyrrolidine-1,2-dicarboxylate (2S-AS)

To a stirring solution of compound 2S-AR (9 g, 57.3 mmol) in $CH_2Cl_2$ (90 mL) was added DMAP (7.0 g, 57.3 mmol) followed by $Et_3N$ (15.9 mL, 114.6 mmol) and Boc-anhydride (36.7 mL, 171.9 mmol) at 0° C. The reaction mixture was stirred at RT for 16 h. The reaction mixture was diluted with $CH_2Cl_2$ (50 mL) and washed with aqueous 1N HCl solution followed by brine. The separated organic layer was dried over anhydrous $Na_2SO_4$ and concentrated under vacuum. Obtained crude material was purified by column chromatography eluting with 50% EtOAc/Hexane to afford compound 2S-AS (12 g, 82%).

$^1$H-NMR: (400 MHz, DMSO-$d_6$): δ 4.61 (dd, 1H), 4.19 (q, 2H), 2.46-2.40 (m, 2H), 2.37-2.25 (On, 1H), 1.91-1.85 (m, 1H), 1.42 (s, 9H), 1.22 (t, 3H).

Synthesis of ethyl 2-((tert-butoxycarbonyl) amino)-5-oxohexanoate (2S-AT)

To a stirring solution of compound 2S-AS (12 g, 46.6 mmol) in THF (120 mL) under inert atmosphere was added MeMgBr (3M in ether) (20.2 mL, 60.6 mmol) at 0° C. and stirred for 2 h. After consumption of the starting material (by TLC), the reaction mixture was quenched with aqueous $NH_4Cl$ solution and the aqueous layer was extracted with EtOAc (2×200 mL). The combined organic extracts were dried over anhydrous $Na_2SO_4$ and concentrated under reduced pressure. The crude residue obtained was purified by silica gel column chromatography eluting with 20% EtOAc/Hexane to afford compound 2S-AT (10 g, 79%).

$^1$H-NMR: (400 MHz, $CDCl_3$): δ 5.14 (br s, 1H), 4.23 (q, 2H), 2.62-2.47 (m, 2H), 2.17 (s, 4H), 1.91-1.82 (m, 1H), 1.45 (s, 10H), 1.26 (t, 3H).

Synthesis of ethyl 5-methylpyrrolidine-2-carboxylate (2S-AU & 2S-AV)

To a stirring solution of compound 2S-AT (10 g, 36.7 mmol) in $CH_2Cl_2$ (100 mL) was added TFA (14.89 mL, 194.6 mmol) at 0° C. After being stirred for 2 h at RT, the reaction mixture was concentrated under reduced pressure to get compound 2S-AU. Obtained material was dissolved in ethanol (100 mL) and 10% Pd/C (50% wet, 3 g) under $N_2$ atmosphere. The reaction mixture was stirred under $H_2$ atmosphere (balloon pressure) for 16 h. The reaction mixture was filtered through a pad of celite and filtrate was concentrated under reduced pressure to afford compound 2S-AV (15 g, crude). This material was directly taken for the next step without further purification.

LCMS, m/z: 158.1 [M$^+$+1]

Synthesis of 1-tert-butyl 2-ethyl 5-methylpyrrolidine-1,2-dicarboxylate (2S-AW)

To a stirring solution of compound 2S-AV (30 g, 191 mmol) in $CH_2Cl_2$ (150 mL) was added DMAP (23.3 g, 191 mmol) followed by $Et_3N$ (79.8 mL, 573 mmol) and Boc-anhydride (104 mL, 477 mmol) at 0° C. The reaction mixture was stirred at RT for 16 h. The reaction mixture was diluted with $CH_2Cl_2$ (50 mL) and washed with water (2×150 mL) followed by brine. The separated organic layer was dried over anhydrous $Na_2SO_4$ and concentrated under vacuum. Obtained crude material was purified by column chromatography eluting with 6% EtOAc/hexane to afford compound 2S-AW (30 g, 61.22%) as pale yellow liquid.

$^1$H-NMR: (500 MHz, DMSO-$d_6$): δ 4.13-3.86 (m, 4H), 2.15 (d, J=3.5 Hz, 1H), 1.99-1.82 (m, 2H), 1.52 (t, J=4.5 Hz, 1H), 1.38 (s, 9H), 1.24 (t, J=5.5 Hz, 3H), 1.16 (d, J=6.5 Hz, 3H).

LCMS, m/z: 258 [(M$^+$+1)

Synthesis of 1-tert-butyl 2-ethyl 2-((benzyloxy) methyl)-5-methylpyrrolidine-1, 2-dicarboxylate (2S-AX)

To a stirring solution of compound 2S-AW (8.0 g, 31.12 mmol) in THF (70 mL) was added LiHMDS (59 mL, 41.72 mmol) at −78° C. and stirred for 2 h. To this BOM-chloride (6.56 mL, 41.72 mmol) was added dropwise and stirred for 2 h at −30° C. After consumption of the starting material (by TLC), the reaction was quenched with aqueous $NH_4Cl$ solution (20 mL) and extracted with DCM (30 mL). The separated organic layer was dried over $Na_2SO_4$ and concentrated to afford crude material was purified by column chromatography eluting with 10% EtOAc/Hexane to afford compound 2S-AX (11 g, 94.2%) as pale yellow liquid.

$^1$H-NMR: (500 MHz, DMSO-$d_6$): δ 7.33-7.25 (m, 5H), 4.38 (d, J=10.5 Hz, 2H), 4.08-3.98 (m, 1H), 3.88 (d, J=9.5 Hz, 2H), 2.20-2.08 (m, 2H), 1.38 (s, 9H), 1.37-1.29 (m, 4H), 1.19 (t, J=7.5 Hz, 3H), 1.14-1.10 (m, 3H);

LCMS, m/z: 378 (M$^+$+1)

Synthesis of 2-((benzyloxy) methyl)-1-(tert-butoxycarbonyl)-5-methylpyrrolidine-2-carboxylic acid (2S-AY)

To a stirring solution of compound 2S-AX (11 g, 29.17 mmol) in $CH_3OH$/THF (22 mL/20 mL) were added 2N NaOH solution (33 mL) at RT. The reaction mixture was heated to 65° C. for 8 h. After consumption of the starting material (by TLC), the solvent from the reaction was evaporated under reduced pressure and diluted with EtOAc (50 mL). The aqueous layer was acidified using citric acid solution and extracted with $CH_2Cl_2$ (2×100 mL). The separated organic layer was washed with water (1×50 mL), dried over $Na_2SO_4$ and concentrated to afford compound 2S-AY (8 g, 80%).

$^1$H-NMR: (400 MHz, DMSO-$d_6$): δ 12.58 (s, 1H), 7.34-7.28 (m, 5H), 4.54-4.47 (m, 2H), 4.05-3.87 (m, 2H), 3.70-3.62 (m, 1H), 2.28-2.08 (m, 3H), 1.46-1.37 (m, 1H), 1.28 (s, 9H);

LCMS, m/z: 350 [M$^+$+1].

Synthesis of 1-(tert-butoxycarbonyl)-2-(hydroxymethyl)-5-methylpyrrolidine-2-carboxylic acid (2S-AZ)

To a stirring solution of compound 2S-AY (8 g, 1.45 mmol) in methanol (40 mL) was added 10% Pd/C (4 g) under $N_2$ atmosphere. The reaction mixture was stirred under $H_2$ atmosphere (balloon pressure) at RT for 16 h. After consumption of the starting material (by TLC), the reaction mixture was filtered through a pad of celite and the pad was washed with methanol. Obtained filtrate was concentrated under reduced pressure to afford crude compound which was triturated with n-pentane to obtained compound 2S-AZ (4.5 g, 75.2%) as white solid.

$^1$H-NMR: (500 MHz, DMSO-$d_6$): δ 12.37 (br s, 1H), 4.61 (br s, 1H), 3.95-3.85 (m, 3H), 2.18-2.06 (m, 3H), 1.44-1.41 (m, 1H), 1.38 (s, 9H), 1.09 (d, J=6.0 Hz, 3H);

LCMS (ER): m/z 260 [M$^+$+1]

Synthesis of tert-butyl 2-(((2S, 3R)-1, 3-bis (benzyloxy)-1-oxobutan-2-yl) carbamoyl)-2-(hydroxymethyl)-5-methylpyrrolidine-1-carboxylate (2S-BA)

To a stirring solution of compound 2S-AZ (3 g, 11.58 mmol) in DCM (30 mL) were added N, N-diisopropylethylamine (6 mL, 34.7 mmol), Int D (5 g, 13.8 mmol), followed by EDCI (2.7 g, 13.8 mmol), HOBT (1.9 g, 13.8 mmol) at 0° C. and stirred at RT for 16 h. After consumption of the starting material (by TLC), the reaction mixture was diluted with water (20 mL). The separated organic layer was washed with saturated NaHCO$_3$ solution (1×50 mL), 2N HCl solution (30 mL) followed by brine solution (1×40 mL). The separated organic layer was dried over anhydrous Na$_2$SO$_4$ and concentrated under reduced pressure to afford crude compound which was purified by column chromatography to obtained compound 2S-BA (2 g, 32.5%) as pale yellow liquid.

$^1$H-NMR: (500 MHz, DMSO-d$_6$): δ 7.30-7.17 (m, 10H), 5.16-5.10 (m, 2H), 4.50 (t, J=5.2 Hz, 2H), 4.28 (t, J=12.0 Hz, 1H), 4.13-4.07 (m, 1H), 3.95 (s, 2H), 2.10-1.85 (m, 4H), 1.40-1.35 (m, 1H), 1.30 (s, 9H), 1.18, 1.16 (dd, J=6.4 Hz, 6H);

LCMS (ESI): m/z 440.3 [M$^+$+1]

Synthesis of tert-butyl 2-((2S, 3R)-1, 3-bis(benzyloxy)-1-oxobutan-2-yl)-6-methyl-1-oxo-2, 5-diazaspiro [3.4] octane-5-carboxylate (2S-BB)

To a stirring solution of compound 2S-BA (1.0 g, 1.85 mmol) in THF (10 mL) was added triphenylphosphine (0.935 g, 4.62 mmol) and DIAD (0.75 g, 3.70 mmol). The reaction mixture was stirred at RT for 8 h. After consumption of the starting material (by TLC), the reaction mixture was concentrated under reduced pressure. The crude material was purified by silica gel column chromatography eluting 20% EtOAc/hexane to afford compound 2S-BB (0.8 g, 51%) as yellow liquid.

$^1$H-NMR: (400 MHz, DMSO-d$_6$): δ 7.30-7.17 (m, 10H), 5.17 (s, 2H), 4.79, 4.76 (dd, J=6.0 Hz, 2H), 4.73 (s, 2H), 4.31-4.18 (m, 2H), 3.84 (t, J=6.8 Hz, 2H), 2.12 (t, J=6.8 Hz, 1H), 1.98-1.91 (m, 2H), 1.39 (s, 9H), 1.32, 1.25 (dd, J=6.0 Hz, 6.4 Hz, 3H), 1.18, 1.09 (dd, J=6.0 Hz, 6.4 Hz, 3H);

LCMS (ESI): m/z 523.3 [M$^+$+1]

Synthesis of (2S, 3R)-2-(5-(tert-butoxycarbonyl)-6-methyl-1-oxo-2, 5-diazaspiro [3.4] octan-2-yl)-3-hydroxybutanoic acid (2S-BC)

To a stirring solution of compound 2S-BB (1 g, 1.91 mmol) in methanol (20 mL) was added 10% Pd/C (400 mg) under N$_2$ atmosphere. The reaction mixture was stirred under H$_2$ atmosphere (balloon pressure) at RT for 16 h. After consumption of the starting material (by TLC), the reaction mixture was filtered through a pad of celite and the pad was washed with methanol. Obtained filtrate was concentrated under reduced pressure to afford compound 2S-BC (0.80 g, crude) as white solid.

$^1$H-NMR: (400 MHz, DMSO-d$_6$): δ 12.75 (br s, 1H), 4.80-4.73 (m, 3H), 4.20-4.05 (m, 2H), 3.40, 3.36 (dd, J=6.8 Hz, 1H), 2.21-2.13 (m, 1H), 2.06-1.99 (m, 2H), 1.53 (t, J=6.0 Hz, 1H), 1.40 (s, 9H), 1.11, 1.10 (dd, J=4.8 Hz, 5.2 Hz, 6H);

LCMS (ESI): m/z 343.3 [M$^+$+1]

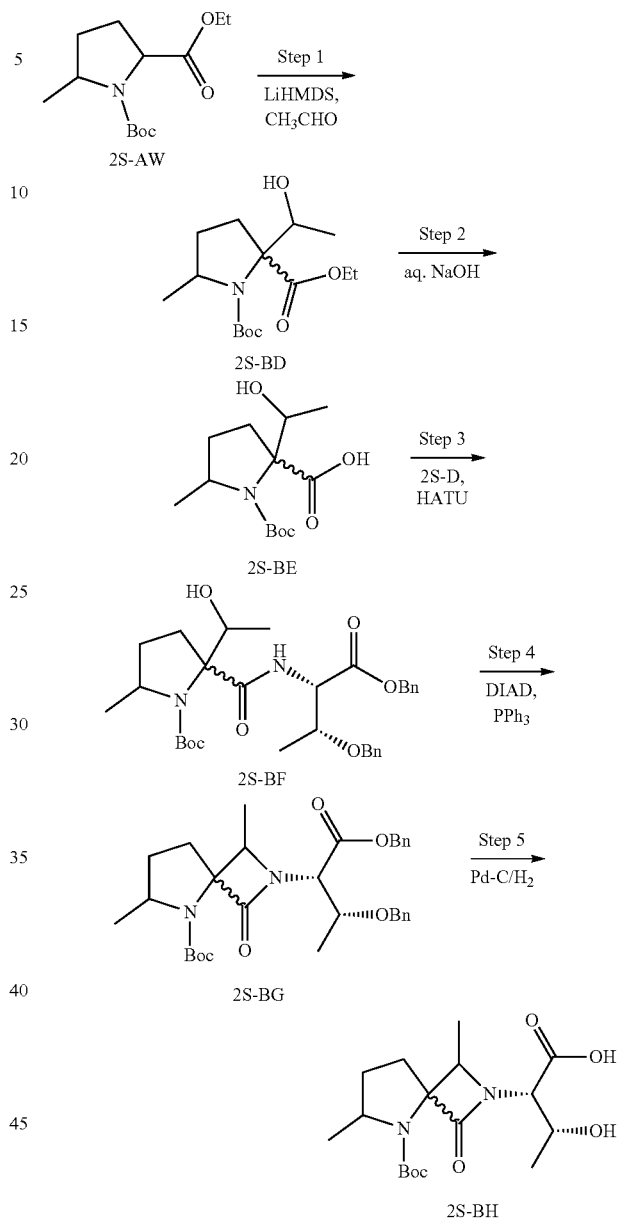

Scheme 2S-I-12

Synthesis of 1-tert-butyl 2-ethyl 2-(1-hydroxyethyl)-5-methylpyrrolidine-1, 2-dicarboxylate (2S-BD)

To a stirring solution of compound 2S-AW (20 g, 77.8 mmol) in THF (200 mL) was added LiHMDS (84 mL, 155 mmol) dropwise at −20° C. and stirred for 30 min. To this acetaldehyde (8.77 mL, 155 mmol) was added drop wise and stirred at RT for 3 h. After consumption of the starting material (by TLC), the reaction was quenched with aqueous NH$_4$Cl solution (100 mL) and extracted with DCM (2×150 mL). The combined organic layer was washed with brine solution (1×150 mL). The separated organic layer was dried over Na$_2$SO$_4$ and concentrated to afford crude material was purified by column chromatography eluting with 30% EtOAc/Hexane to afford compound 2S-BD (16 g, 23.1%) as colorless syrup.

¹H-NMR: (500 MHz, DMSO-d₆): δ 7.33-7.25 (m, 5H), 4.38 (d, J=10.5 Hz, 2H), 4.08-3.98 (m, 1H), 3.88 (d, J=9.5 Hz, 2H), 2.20-2.08 (m, 2H), 1.38 (s, 9H), 1.37-1.29 (m, 4H), 1.19 (t, J=7.5 Hz, 3H), 1.14-1.10 (m, 3H);
LCMS m/z: 378 (M⁺+1)

Synthesis of 1-(tert-butoxycarbonyl)-2-(1-hydroxy-ethyl)-5-methylpyrrolidine-2-carboxylic acid (2S-BE)

To a stirring solution of compound 2S-BD (15 g, 49 mmol) in EtOH/THF (10 mL/20 mL) were added NaOH (3.98 g, 99 mmol) in water (10 mL) at RT. The reaction mixture was heated to 90° C. for 4 h. After consumption of the starting material (by TLC), the solvent from the reaction was evaporated under reduced pressure and acidified by using citric acid (pH~4). The aqueous layer was extracted with DCM (2×200 mL) and the combined organic layer was washed with brine solution (1×150 mL). The separated organic layer was dried over Na₂SO₄ and concentrated to obtained crude compound, which was purified by column chromatography eluting 40% EtOAc/n-hexane to afford compound 2S-BE (8.2 g, 60.7%) as brown syrup.
¹H-NMR: (500 MHz, DMSO-d₆): δ 12.15 (br s, 2H), 4.54-4.50 (m, 1H), 4.03-4.02 (m, 1H), 2.17-1.77 (m, 3H), 1.41 (s, 9H), 1.39-1.09 (m, 3H), 0.99-0.94 (m, 3H);
LCMS m/z: 272.4 [M⁻−1]

Synthesis of tert-butyl 2-(((2S,3R)-1,3-bis(benzy-loxy)-1-oxobutan-2-yl)carbamoyl)-2-(1-hydroxy-ethyl)-5-methylpyrrolidine-1-carboxylate (2S-BF)

To a stirring solution of compound 2S-BE (8 g, 29.3 mmol) in DCM (100 mL) were added N, N-diisopropyleth-ylamine (15.12 mL, 87 mmol), 2S-D (12.13 g, 40.6 mmol) followed by HATU (16.5 g, 43.5 mmol) at 0° C. and stirred at RT for 12 h. After consumption of the starting material (by TLC), the reaction mixture was diluted with water (100 mL). The separated organic layer was washed with citric acid solution (1×75 mL) followed by brine solution (1×100 mL). The organic layer was dried over anhydrous Na₂SO₄ and concentrated under reduced pressure to afford crude compound which was purified by column chromatography by eluting with 40% EtOAc/n-hexane to obtain compound 2S-BF (11 g, 68.4%) as pale yellow liquid.
¹H-NMR: (400 MHz, DMSO-d₆): δ 7.31-7.19 (m, 10H), 5.14-5.06 (m, 2H), 4.59-4.48 (m, 3H), 4.31-4.26 (m, 1H), 4.05-4.00 (m, 2H), 1.98-1.89 (m, 2H), 1.41 (s, 9H), 1.39-1.35 (m, 3H), 1.28-1.17 (m, 6H), 1.16-1.00 (m, 3H);
LCMS (ESI): 555.6 [M⁺+1]

Synthesis of tert-butyl 2-((2S,3R)-1,3-bis(benzy-loxy)-1-oxobutan-2-yl)-1,6-dimethyl-3-oxo-2,5-diaz-aspiro[3.4]octane-5-carboxylate (2S-BG)

To a stirring solution of triphenylphosphine (3.5 g, 13.5 mmol) in THF (10 mL) was added DIAD (2.72 g, 13.5 mmol) as portion-wise and stirred for 20 min at RT. To this added compound 2S-BF (3 g, 5.4 mmol) in THF (10 mL) slowly at RT and stirred for 3 h. After consumption of the starting material (by LCMS), the reaction mixture was concentrated under reduced pressure. The crude material was purified by silica gel column chromatography eluting 20% EtOAc/hexane to afford compound 2S-BG (2.5 g, 86.5%) as yellow liquid.
¹H-NMR: (400 MHz, DMSO-d₆): δ7.39-7.18 (m, 10H), 5.19-5.10 (m, 2H), 4.78-4.49 (m, 3H), 4.34-4.25 (m, 2H), 3.85-3.76 (m, 1H), 2.10-1.69 (m, 4H), 1.40 (s, 9H), 1.35-1.26 (m, 3H), 1.18-1.12 (m, 6H);

Synthesis of (2S,3R)-2-(5-(tert-butoxycarbonyl)-1,6-dimethyl-3-oxo-2,5-diazaspiro [3.4] octan-2-yl)-3-hydroxybutanoic acid (2S-BH)

To a stirring solution of compound 2S-BG (2 g, 3.72 mmol) in methanol (20 mL) was added 10% dry Pd/C (200 mg) under N₂ atmosphere. The reaction mixture was stirred under H₂ atmosphere at RT for 12 h. After consumption of the starting material (by TLC), the reaction mixture was filtered through a pad of celite and the pad was washed with methanol (10 mL). Obtained filtrate was concentrated under reduced pressure to afford compound 2S-BH (1.8 g, 60.4%) as yellow solid.
¹H-NMR: (400 MHz, DMSO-d₆): δ 12.72 (br s, 1H), 5.11-4.97 (m, 1H), 4.30-4.15 (m, 2H), 3.91-3.76 (m, 2H), 2.18-1.90 (m, 3H), 1.40 (s, 9H), 1.37-1.29 (m, 1H), 1.26-1.22 (m, 3H), 1.21-1.10 (m, 6H);
LCMS (ESI): 357.5 [M⁺+1]

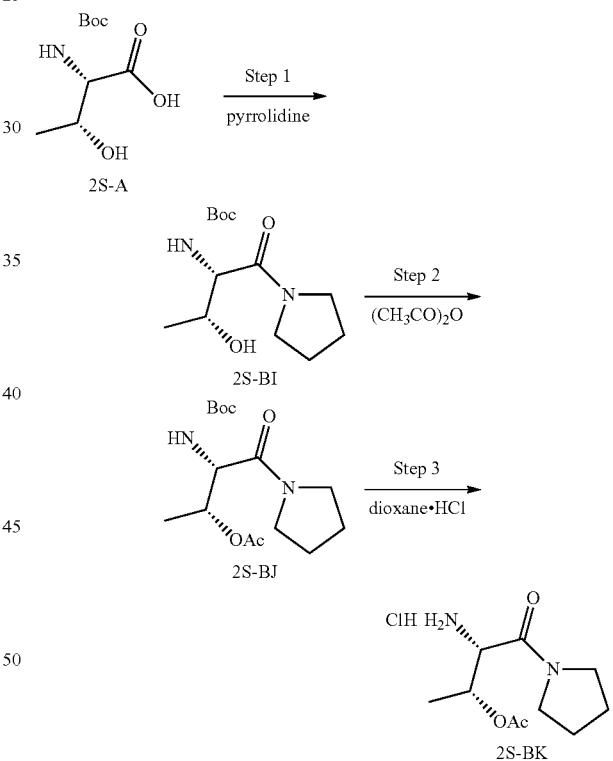

Scheme 2S-I-13

Synthesis of tert-butyl ((2S, 3R)-3-hydroxy-1-oxo-1-(pyrrolidin-1-yl) butan-2-yl) carbamate (2S-BI)

To a stirring solution of compound 2S-A (13 g, 59.36 mmol) in DMF (65 mL) was added EDCI.HCl (12.5 g, 65.2 mmol) followed by HOBt (8.8 g, 65.2 mmol) at 0° C. After being stirred for 5 min, DIPEA (30.6 mL, 0.17 mol) followed by pyrrolidine (4.6 g, 65.2 mmol) was added to the reaction mixture and stirring was continued for another 16 h at RT. The reaction mixture was washed with water and extracted with EtOAc (2×100 mL). The organic layer was washed with brine, dried over anhydrous Na₂SO₄ and concentrated under vacuum. The crude was purified by column chromatography to afford compound 2S-BI (5 g, 31%).

¹H-NMR: (400 MHz, CDCl₃): δ5.51 (br s, 1H), 4.32 (d, 1H), 4.15-4.10 (m, 1H), 3.77-3.74 (m, 1H), 3.55-3.46 (m, 3H), 1.99-1.94 (m, 2H), 1.91-1.85 (m, 2H), 1.47 (s, 9H), 1.26 (t, 1H), 1.29 (d, 3H).

Synthesis of (2R, 3S)-3-((tert-butoxycarbonyl)amino)-4-oxo-4-(pyrrolidin-1-yl) butan-2-yl acetate (2S-BJ and 2S-BK)

To a stirring solution of compound 2S-BI (4 g, 14.7 mmol) in CH₂Cl₂ (40 mL) was added Et₃N (5.1 mL, 36.7 mmol) followed by acetic anhydride (1.7 g, 17.6 mmol) and catalytic amount of DMAP at 0° C. The reaction mixture was stirred at RT for 16 h. After consumption of the starting material (by TLC), the reaction mixture was diluted with water and separated the organic layer. Organic layer was washed with water, dried over anhydrous Na₂SO₄ and concentrated under reduced pressure. The crude residue obtained was purified by silica gel column chromatography to give compound 2S-BJ. To this 1, 4-dioxane/HCl (20 mL) was added and stirred at RT for 2 h. The reaction mixture was concentrated under vacuum and obtained material was washed with Et₂O (2×15 mL) to afford compound 2S-BK (3.5 g, 97%) as HCl salt.

¹H-NMR: (500 MHz, DMSO-d₆) (Rotamers): δ 8.49 (br s, 3H), 8.15 (br s, 1H), 5.14-5.10 (m, 1H), 4.26-4.22 (m, 1H), 3.97-3.95 (m, 1H), 3.59 (s, 2H), 2.09 (s, 3H), 1.98 (s, 2H), 1.87-1.80 (m, 2H), 1.26 (d, 3H).

LCMS (ESI): 215.1 [M⁺+1].

layer was dried over anhydrous Na₂SO₄ and concentrated under reduced pressure to afford crude compound which was purified by column chromatography eluting 1% MeOH/DCM to obtained compound 2S-BL (8 g, 86%) as white solid.

¹H-NMR: (400 MHz, DMSO-d₆): δ 7.34-7.24 (m, 5H), 6.57 (d, J=4.0 Hz, 1H), 4.53, 4.44 (dd, J=12.0 Hz, 12.0 Hz, 2H), 4.32-4.28 (m, 1H), 3.74 (t, J=6.0 Hz, 1H), 3.58-3.53 (m, 1H), 3.42-3.38 (m, 1H), 3.28-3.24 (m, 2H), 1.82-1.70 (m, 4H), 1.37 (s, 9H), 1.11 (d, J=6.4 Hz, 3H)

Mass (ESI): m/z 363.4 [M⁺+1].

Synthesis of (2S, 3R)-2-amino-3-(benzyloxy)-1-(pyrrolidin-1-yl) butan-1-one (2S-BM)

To a stirring solution of compound 2S-BL (6 g, 16.52 mmol) in ether saturated with HCl (30 mL) was added at 0° C. and stirred at RT for 2 h. After consumption of the starting material (by TLC), the reaction mixture was concentrated under reduced pressure to afford crude compound which was triturated with pentane (15 mL) to obtained compound 2S-BM (4 g, 93%) as white solid.

¹H-NMR: (500 MHz, DMSO-d₆): δ 8.25 (s, 2H), 7.36-7.29 (m, 5H), 4.58, 4.48 (dd, J=12.0, 11.5 Hz, 2H), 4.12 (t, J=4.5 Hz, 1H), 3.87 (t, J=5.5 Hz, 1H), 3.60-3.57 (m, 1H), 3.37-3.33 (m, 3H), 1.78-1.70 (m, 4H), 1.22 (d, J=6.5 Hz, 3H).

Mass (ESI): 263.3[M⁺+1].

Scheme 2S-I-14

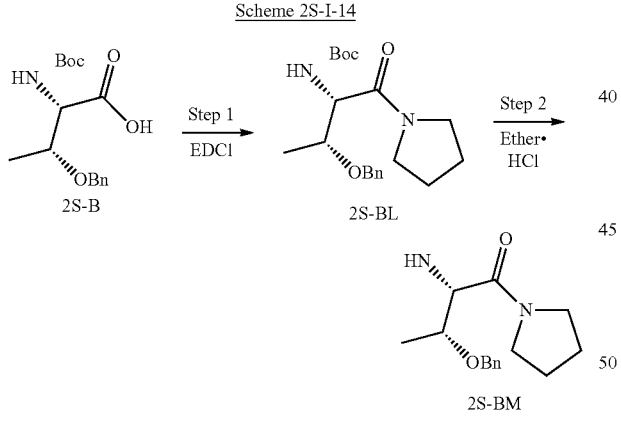

Synthesis of tert-butyl ((2S, 3R)-3-(benzyloxy)-1-oxo-1-(pyrrolidin-1-yl) butan-2-yl) carbamate (2S-BL)

To a stirring solution of compound 2S-B (8 g, 25.8 mmol) in DCM (80 mL) were added N, N-diisopropylethylamine (11 mL, 87.4 mmol), pyrrolidine (2.5 mL, 35.4 mmol), followed by EDCI (7.39 g, 38.7 mmol), HOIST (5.2 g, 38.7 mmol) at 0° C. and stirred at RT for 16 h. After consumption of the starting material (by TLC), the reaction mixture was diluted with water (20 mL). The separated organic layer was washed with saturated NaHCO₃ solution (1×25 mL), followed by brine solution (1×30 mL). The separated organic Scheme 2S-I

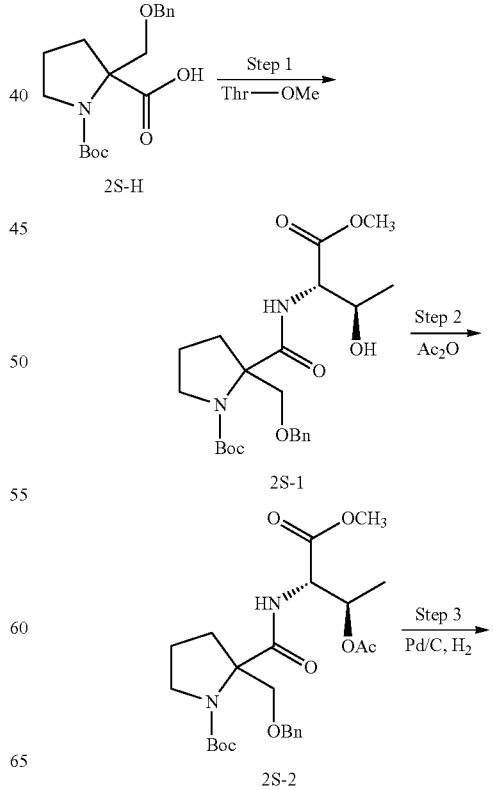

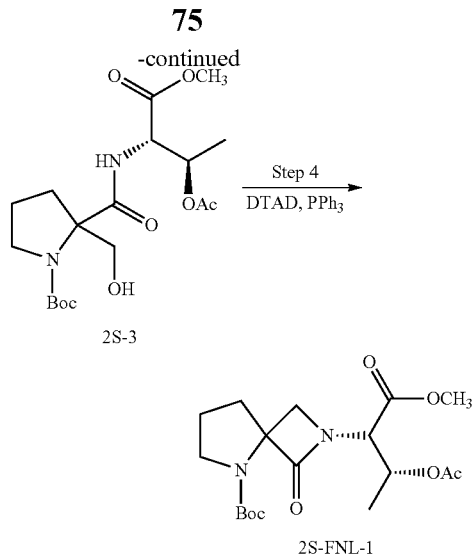

Synthesis of tert-Butyl2-((benzyloxy)methyl)-2-(((2S,3R)-3-hydroxy-1-methoxy-1-oxobutan-2-yl)carbamoyl) pyrrolidine-1-carboxylate (2S-1)

To a stirred solution of compound 2S-H (2.0 g, 5.97 mmol) in $CH_2Cl_2$ (10 mL) was added DIPEA (2.6 mL, 14.92 mmol) followed by HATU (2.26 g, 5.94 mmol) at 0° C. and stirred for 10 minutes. A solution of methyl 2-amino-3-hydroxybutanoate hydrochloride (1 g, 5.97 mmol) in $CH_2Cl_2$ (10 mL) was added to the reaction mixture at 0° C. The resultant reaction mixture was allowed to warm to RT and stirring was continued for another 3 h. The volatiles were evaporated under reduced pressure. The obtained residue was diluted with water (25 mL) and extracted with $CH_2Cl_2$ (2×75 mL). The organic layer was dried over anhydrous $Na_2SO_4$ and concentrated under reduced pressure. The crude was purified by silica gel column chromatography eluting with 40% EtOAc/Hexane to afford compound 2S-1 (1.8 g, 67%) as a liquid.

$^1$H-NMR: (400 MHz, DMSO-$d_6$): δ 7.38-7.31 (m, 5H), 5.16 (br s, 1H), 4.54 (s, 2H), 4.28-4.26 (m, 1H), 4.17-4.12 (m, 1H), 3.84-3.82 (m, 1H), 3.62 (s, 3H), 3.54-3.51 (m, 1H), 2.32-2.27 (m, 4H), 1.84-1.78 (m, 2H), 1.42 (s, 9H), 1.06 (d, 3H);

LCMS m/z: 451.6 [M$^+$+1]

Synthesis of tert-Butyl-2-(((2S,3R)-3-acetoxy-1-methoxy-1-oxobutan-2-yl)carbamoyl)-2-((benzyloxy)methyl) pyrrolidine-1-carboxylate (2S-2)

To a stirred solution of compound 2S-1 (1.0 g, 2.22 mmol) in $CH_2Cl_2$ (15 mL) was added Et$_3$N (0.34 mL, 2.44 mmol) drop wise at 0° C. under inert atmosphere. To this Ac$_2$O (0.27 mL, 2.64 mmol) followed by DMAP (50 mg, 0.40 mmol) was added at 0° C. and allowed to stir at RT for 2 h. The reaction mixture was diluted with water and the aqueous layer was extracted with $CH_2Cl_2$ (2×25 mL). The combined organic extracts were dried over anhydrous $Na_2SO_4$ and concentrated under reduced pressure to afford compound 2S-2 (0.8 g, 73%) as a liquid.

$^1$H-NMR: (400 MHz, DMSO-$d_6$): δ 7.41-7.34 (m, 5H), 5.26-5.24 (m, 1H), 4.54 (s, 2H), 4.06-3.97 (m, 1H), 3.78-3.72 (m, 1H), 3.62 (s, 3H), 3.52-3.49 (m, 1H), 2.68 (s, 6H), 2.34-2.31 (m, 1H), 1.87 (s, 3H), 1.78-1.74 (m, 2H), 1.42 (s, 6H), 1.14 (d, 3H).

Mass m/z: 493.8 [M$^+$+1]

Synthesis of tert-Butyl-2-(((2S, 3R)-3-acetoxy-1-methoxy-1-oxobutan-2-yl)carbamoyl)-2-(hydroxymethyl) pyrrolidine-1-carboxylate (2S-3)

To a stirred solution of compound 2S-2 (0.8 g, 1.62 mmol) in EtOAc (15 mL) was added 10% Pd-C (0.15 g) and stirred at RT for 24 h under H$_2$ atmosphere (balloon pressure). The reaction mixture was filtered through a celite pad and washed with EtOAc. The filtrate was concentrated under reduced pressure. The crude compound was purified by silica gel column chromatography eluting with 40% EtOAc/hexane to afford compound 2S-3 (0.5 g, 77%) as a liquid.

$^1$H-NMR: (500 MHz, DMSO-$d_6$): δ 8.16 (br s, 1H), 5.78-5.74 (m, 1H), 5.23 (d, J=9.5 Hz, 1H), 4.64-4.58 (m, 1H), 4.03-3.98 (m, 1H), 3.61 (s, 3H), 3.52 (d, J=10.0 Hz, 1H), 3.43 (d, J=6.5 Hz, 1H), 2.29-2.27 (m, 1H), 1.96-1.94 (m, 4H), 1.74-1.68 (m, 2H), 1.38-1.30 (m, 9H), 1.14 (d, J=6.5 Hz, 3H);

LCMS m/z: 403.6 [M$^+$+1]

Synthesis of tert-Butyl-2-((2S,3R)-3-acetoxy-1-methoxy-1-oxobutan-2-yl)-1-oxo-2,5-diaza spiro [3.4]octane-5-carboxylate (2S-FNL-1)

To a stirred solution of compound 2S-3 (0.35 g, 0.87 mmol) in THF (15 mL) was added PPh$_3$ (274 mg, 1.04 mmol) at RT and stirred for 30 minutes under inert atmosphere. Then the reaction mixture was cooled 0° C., DTAD (0.22 g, 0.95 mmol) was added to the reaction mixture and allowed to warm to room temperature and stirring was continued for another 20 h. It was quenched with saturated citric acid and washed with saturated NaCl solution and extracted with EtOAc (2×20 mL). The combined organic extract were dried over anhydrous $Na_2SO_4$ and concentrated under reduced pressure. The obtained crude material was purified by silica gel column chromatography eluting with 40% EtOAc/Hexane to afford NRX-1076 (2S-FNL-1) (160 mg, 48%) as a liquid.

$^1$H-NMR: (400 MHz, DMSO-$d_6$): δ 5.21-5.18 (m, 1H), 4.57 (d, 1H), 3.82 (d, 1H), 3.64 (d, 3H), 3.42 (d, 2H), 3.24-3.21 (m, 1H), 2.14-2.11 (m, 2H), 1.97 (s, 3H), 1.84-1.78 (m, 2H), 1.37 (s, 9H), 1.18 (d, 3H);

Mass m/z: 383.1 [M−1]

Scheme 2S-2:

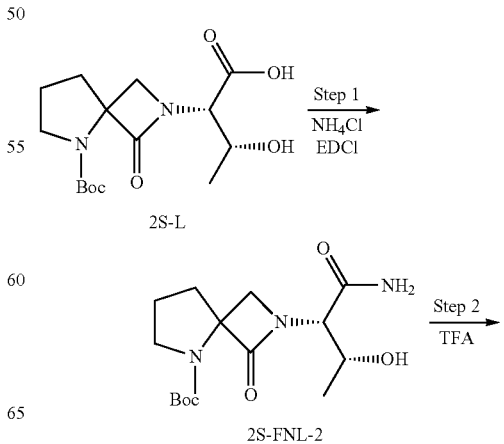

-continued

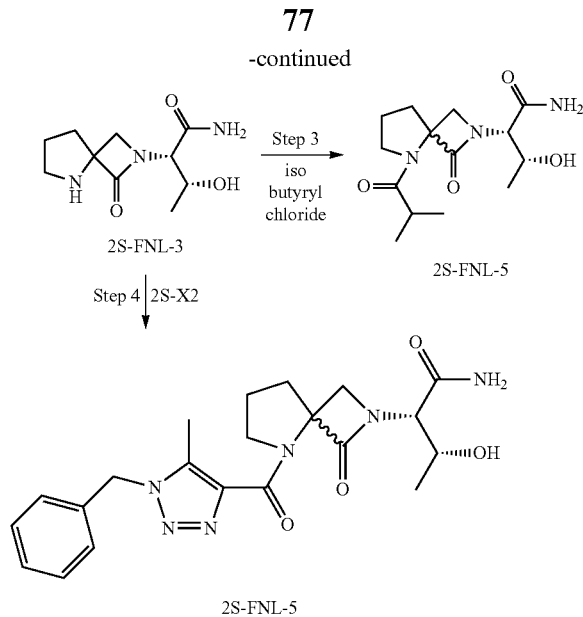

Synthesis of tert-butyl 2-((2S, 3R)-1-amino-3-hydroxy-1-oxobutan-2-yl)-1-oxo-2, 5-diazaspiro [3.4] octane-5-carboxylate (2S-FNL-2)

To a stirring solution of compound 2S-L (500 mg, 1.52 mmol) in CH$_2$Cl$_2$ (5 mL) were added DIPEA (0.8 mL, 4.57 mmol), EDCI.HCl (350 mg, 1.82 mmol) followed by HOBt (280 mg, 1.82 mmol), NH$_4$Cl (161 mg, 3.04 mmol) at 0° C. and stirred for 16 h at RT. After consumption of the starting material (by TLC), the reaction mixture was diluted with water (10 mL) and extracted with CH$_2$Cl$_2$ (2×30 mL). The combined organic layer was washed with citric acid solution (2×30 mL). The organic layer was dried over anhydrous Na$_2$SO$_4$, filtered and concentrated under reduced pressure. Obtained crude material was purified by silica gel column chromatography eluting 2% MeOH/DCM to afford compound (2S-FNL-2) (200 mg, 40%) as colorless liquid.

$^1$H-NMR: (500 MHz, DMSO-d$_6$): δ 7.53 (s, 2H), 4.59 (s, 1H), 4.02 (s, 1H), 3.77-3.70 (m, 2H), 3.62-3.53 (m, 2H), 3.46-3.33 (m, 1H), 2.17-2.03 (m, 2H), 1.88-1.71 (m, 2H), 1.38 (s, 9H), 1.18 (d, J=6.5 Hz, 3H);
Mass (ESI): 328.3 [M$^+$+1]

Synthesis of (2S, 3R)-3-hydroxy-2-(1-oxo-2, 5-diazaspiro [3.4] octan-2-yl) butanamide (2S-FNL-3)

To a stirring solution of compound (2S-FNL-2) (200 mg, 0.61 mmol) in CH$_2$Cl$_2$ (5 mL) was added TFA (0.5 mL, 6.1 mmol) at 0° C. and stirred at RT for 3 h. After completion of reaction (by TLC), the reaction mixture was concentrated under reduced pressure to obtained crude compound which was triturated with n-pentane/diethylether (5 mL/5 mL) to afford compound (2S-FNL-3) (100 mg) as white solid (TFA salt).

$^1$H-NMR: (400 MHz, D$_2$O): δ 4.33-4.29 (m, 2H), 4.09 (d, 1H), 3.95 (d, 11-1), 3.57-3.48 (m, 2H), 2.51-2.46 (m, 2H), 2.25-2.19 (m, 2H), 1.31 (d, 3H);
LCMS, m/z: 455 [2M$^+$+1]

Synthesis of (2S, 3R)-3-hydroxy-2-(5-isobutyryl-1-oxo-2, 5-diazaspiro [3.4] octan-2-yl) butanamide (2S-FNL-4)

To a stirring solution of (2S-FNL-3) (500 mg (crude), 2.20 mmol) in CH$_2$Cl$_2$ (10 mL) was added TEA (1 mL, 7.70 mmol) followed by SM3 (256 mg, 2.42 mmol) at 0° C. and stirred for 16 h at RT. After consumption of the starting material (by TLC), the reaction mixture was diluted with water (10 mL) and extracted with CH$_2$Cl$_2$ (2×30 mL). The combined organic layer was washed with citric acid solution (2×30 mL). The organic layer was dried over anhydrous Na$_2$SO$_4$, filtered and concentrated under reduced pressure. Obtained crude material was purified by silica gel column chromatography eluting 2% MeOH/DCM to afford (2S-FNL-4) (100 mg, 15.2%) as white solid.

$^1$H-NMR: (500 MHz, D$_2$O): δ 4.54-4.52 (m, 1H), 4.41-4.37 (m, 1H), 4.27 (d, J=3.6 Hz, 1H), 4.04 (t, J=6.5 Hz, 1H), 3.85-3.72 (m, 1H), 3.71-3.66 (m, 1H), 2.92-2.87 (m, 1H), 2.38-2.27 (m, 2H), 2.12-2.05 (m, 2H), 1.30 (d, J=6.5 Hz, 3H), 1.14 (d, J=6.5 Hz, 6H);
Mass (ESI): 298.3 [M$^+$+1]

Synthesis of (2S, 3R)-2-(5-(1-benzyl-5-methyl-1H-1, 2, 3-triazole-4-carbonyl)-1-oxo-2, 5-diazaspiro [3.4] octan-2-yl)-3-hydroxybutanamide (2S-FNL-5)

To a stirring solution of 2S-X2 (200 mg, 0.92 mmol) in CH$_2$Cl$_2$ (10 mL), DMF (0.1 mL) were added oxalyl chloride (0.16 mL, 1.84 mmol) at 0° C. The reaction mixture was warmed to RT and stirred for 2 h. The volatiles were evaporated under reduced pressure in presence of N$_2$ atmosphere to afford acid chloride (300 mg, crude). To a stirred solution of acid chloride (300 mg, crude) in DCM (5 mL) was added (2S-FNL-3) (220 mg, 0.92 mmol), N, N-diisopropylethylamine (0.53 mL, 2.76 mmol) at 0° C., The resulting reaction mixture was stirred at RT for 1 h. After consumption of the starting material (by TLC), the reaction mixture was diluted with water (10 mL) and extracted with CH$_2$Cl$_2$ (2×20 mL). Combined organic extracts were washed by brine solution (2×10 mL) and dried over anhydrous Na$_2$SO$_4$ concentrated under reduced pressure to obtain crude product, which was purified by silica gel column chromatography eluting with 3% MeOH/CH$_2$Cl$_2$ to afford compound (2S-FNL-5) (200 mg, 48.6%) as pale brown solid.

$^1$H-NMR: (500 MHz, DMSO-d$_6$): δ 7.77 (s, 2H), 7.38-7.31 (m, 3H), 7.18 (d, J=7.5 Hz, 2H), 5.65 (s, 2H), 4.89 (d, J=5.5 Hz, 1H), 4.76 (d, J=4.0 Hz, 1H), 4.07-3.91 (m, 4H), 3.62-3.48 (m, 1H), 2.39 (s, 3H), 2.26-2.12 (m, 2H), 1.98-1.91 (m, 2H), 1.13 (d, J=6.5 Hz, 3H);
LCMS m/z: 427.6 [M$^+$+1];
HPLC: 95.5% (both enantiomers)

Scheme 2S-2:

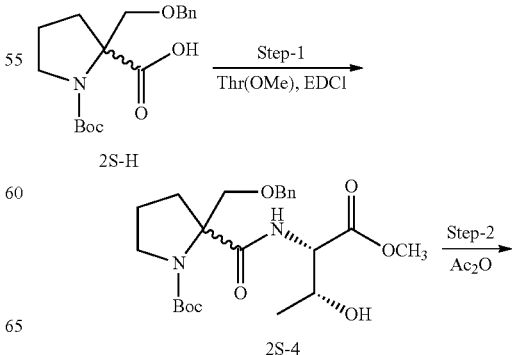

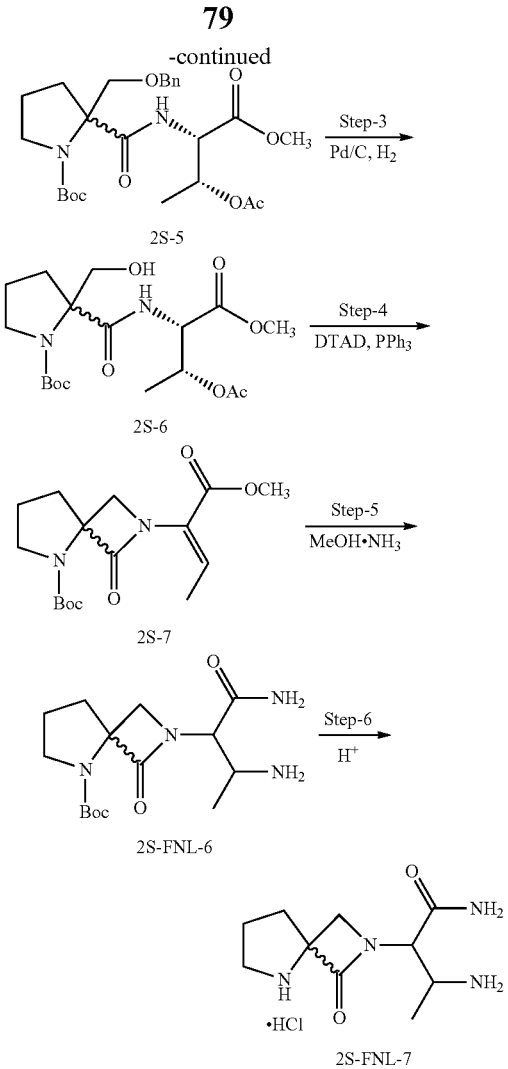

Synthesis of tert-butyl 2-((benzyloxy)methyl)-2-(((2S,3R)-3-hydroxy-1-methoxy-1-oxobutan-2-yl)carbamoyl)pyrrolidine-1-carboxylate (2S-4)

To a stirring solution of compound 2S-H (50 g, 0.15 mol) in CH$_2$Cl$_2$ (500 mL) was added methyl 2-amino-3-hydroxybutanoate (23.8 g, 0.18 mol), EDCI.HCl (34.2 g, 0.18 mol) followed by HOBt (24.1 g, 0.18 mol) and DIPEA (57.8 g, 0.45 mol) at RT and stirred for 2 h. After consumption of the starting material (by TLC), the reaction mixture was diluted with water (250 mL) and extracted with CH$_2$Cl$_2$ (2×250 mL). The separated organic layers were washed with water, brine, dried over anhydrous Na$_2$SO$_4$, filtered and concentrated under reduced pressure. Obtained crude material was purified by silica gel column chromatography eluting with 50% EtOAc/Hexane to afford compound 2S-4 (53 g, 78.9%) as light green liquid.

Synthesis of tert-butyl 2-(((2S,3R)-3-acetoxy-1-methoxy-1-oxobutan-2-yl)carbamoyl)-2-((benzyloxy)methyl)pyrrolidine-1-carboxylate (2S-5)

To a stirring solution of compound 2S-4 (15 g, 33.3 mmol) in CH$_2$Cl$_2$ (150 mL) was added DIPEA (6.4 g, 49.9 mmol) followed by acetic anhydride (4 g, 39.9 mmol) and DMAP (408 mg, 3.33 mmol) at RT and stirred for 2 h. After consumption of the starting material (by TLC), the reaction mixture was diluted with water (100 mL) and extracted with CH$_2$Cl$_2$ (2×100 mL). The separated organic layer was washed with brine, dried over anhydrous Na$_2$SO$_4$, filtered and concentrated under reduced pressure to afford compound 2S-5 (16 g, crude) as light brown liquid.

$^1$H-NMR: (400 MHz, CDCl$_3$): δ 7.35 (d, 5H), 5.47-5.44 (m, 1H), 4.80 (dd, 1H), 4.64-4.61 (m, 2H), 4.15-4.11 (m, 1H), 3.86-3.83 (m, 1H), 3.75 (s, 4H), 3.54-3.50 (m, 2H), 2.42-3.38 (m, 1H), 1.91-1.85 (m, 5H), 1.45-1.41 (m, 10H), 1.27 (d, 2H);

LCMS (ESI): 492 [M$^+$]

Synthesis of tert-butyl 2-(((2S,3R)-3-acetoxy-1-methoxy-1-oxobutan-2-yl)carbamoyl)-2-(hydroxymethyl)pyrrolidine-1-carboxylate (2S-6)

To a stirring solution of compound 2S-5 (16 g, 32.5 mmol) in methanol (100 mL) and EtOAc (100 mL) was added 10% Pd on Charcoal (3 g) at RT and stirred for 4 h under H$_2$ atmosphere (balloon pressure). After consumption of the starting material (by TLC), the reaction mixture was filtered through a pad of celite and the pad was washed with methanol. Obtained filtrate was concentrated under reduced pressure to afford compound 2S-6 (10 g, crude) as brown thick syrup. This material was directly used for the next step without further purification.

Synthesis of (Z)-tert-butyl 2-(1-methoxy-1-oxobut-2-en-2-yl)-1-oxo-2, 5-diazaspiro [3.4] octane-5-carboxylate (2S-7)

To a stirring solution of compound 2S-6 (10 g, 24.8 mmol) in THF (50 mL) was added triphenylphosphine (13 g, 49.7 mmol) and DTAD (11.15 g, 37.3 mmol). The reaction mixture was stirred at RT for 16 h. After consumption of the starting material (by TLC), the reaction was concentrated under reduced pressure. The crude material was purified by silica gel column chromatography eluting with 40% EtOAc/hexane to afford compound 2S-7 (2 g, 24.8%).

Synthesis of tert-butyl 2-(1, 3-diamino-1-oxobutan-2-yl)-1-oxo-2, 5-diazaspiro [3.4] octane-5-carboxylate (2S-FNL-6)

A solution of compound 2S-7 (2 g, 6.16 mmol) in methanolc.NH$_3$ (50 mL) was stirred at RT for 4 h. After consumption of the starting material (by TLC), the reaction mixture was concentrated under reduced pressure. Obtained crude material was washed with Et$_2$O (25 mL) and n-pentane (25 mL) to afford (2S-FNL-6) (0.35 g, 16.6%) as white solid.

$^1$H-NMR: (500 MHz, DMSO-d$_6$): δ 7.70 (br s, 1H), 7.07 (s, 1H), 3.85 (d, 1H), 3.73 (d, 1H), 3.42-3.38 (m, 2H), 3.29-3.25 (m, 1H), 3.12-3.07 (m, 1H), 2.09 (t, 2H), 1.95 (br s, 1H), 1.84-1.81 (m, 2H), 1.93 (s, 9H), 1.12 (d, 1H), 0.99 (d, 2H);

LCMS (ESI) m/z: 327.3 [M$^+$+1]

Synthesis of 3-amino-2-(1-oxo-2,5-diazaspiro[3.4]octan-2-yl)butanamide (2S-FNL-7)

To a stirring solution of (2S-FNL-6) (0.25 g, 0.76 mmol) in CH$_2$Cl$_2$ (10 mL) was added ether.HCl (5 mL) at RT and stirred for 4 h. To this was added 1, 4-dioxane-HCl (5 mL) and stirring was continued for 2 h. After consumption of starting material (by TLC), the solvent from the reaction was removed under reduced pressure and obtained crude material was washed with ACN (25 mL) and Et$_2$O (25 mL) to afford (2S-FNL-7) (0.11 g, 63.5%) as an off-white solid.

$^1$H-NMR: (400 MHz, D$_2$O): δ 4.69-4.55 (m, 1H), 4.12-3.86 (m, 3H), 3.62-3.51 (m, 2H), 2.56-2.23 (m, 2H), 2.25-2.21 (m, 2H), 1.52-1.43 (m, 3H).

LCMS (ESI) m/z: 227.2 [M$^+$+1];

UPLC (Purity): 97.96%

Scheme 2S-3:

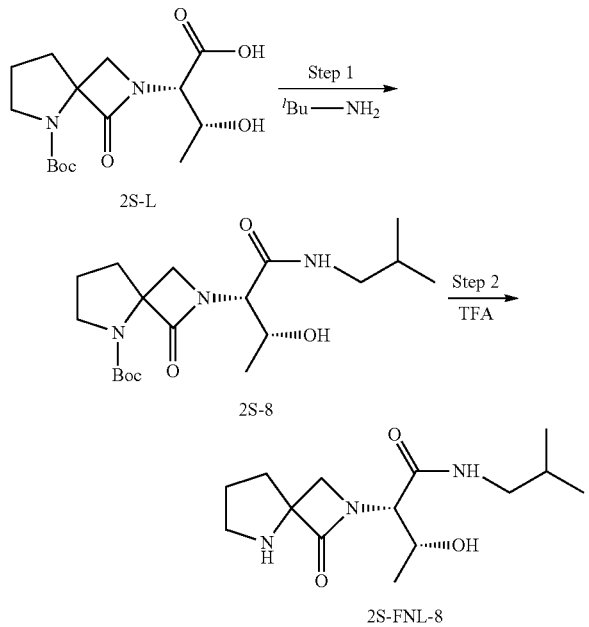

2S-L 2S-8

2S-FNL-8

Synthesis of tert-butyl 2-((2S, 3R)-3-hydroxy-1-(isobutylamino)-1-oxobutan-2-yl)-1-oxo-2, 5-diazaspiro [3.4] octane-5-carboxylate (2S-8)

To a stirring solution of compound 2S-L (300 mg, 0.91 mmol) in CH$_2$Cl$_2$ (10 mL) were added DIPEA (354 mg, 2.74 mmol), EDCI.HCl (210 mg, 1.09 mmol) followed by HOBt (165 mg, 1.09 mmol), isobutylamine (80 mg, 1.09 mmol) at 0° C. and stirred for 16 h at RT. After consumption of the starting material (by TLC), the reaction mixture was diluted with water (10 mL) and extracted with CH$_2$Cl$_2$ (2×30 mL). The combined organic layer was washed with brine (2×30 mL), dried over anhydrous Na$_2$SO$_4$, filtered and concentrated under reduced pressure. Obtained crude material was purified by silica gel column chromatography eluting 2% MeOH/DCM to afford compound 2S-8 (250 mg, 71.5%) as white solid.

$^1$H-NMR: (400 MHz, DMSO-d$_6$): δ 8.02 (t, J=5.2 Hz, 1H), 4.37 (s, 2H), 4.04 (t, J=5.6 Hz, 1H), 4.00 (d, J=5.6 Hz, 1H), 3.77-3.72 (m, 1H), 3.61 (d, J=6.0 Hz, 1H), 3.44-3.38 (m, 1H), 2.98-2.84 (m, 3H), 2.19-2.08 (m, 3H), 1.84-1.79 (m, 1H), 1.42 (s, 9H), 1.39 (d, J=5.5 Hz, 3H), 0.84 (d, J=6.4 Hz, 6H);

Mass (ESI): m/z 384.4 [M$^+$+1]

Synthesis of (2S, 3R)-3-hydroxy-N-isobutyl-2-(1-oxo-2, 5-diazaspiro [3.4] octan-2-yl) butanamide (2S-FNL-8)

To a stirring solution of compound 2S-8 (250 mg, 0.65 mmol) in CH$_2$Cl$_2$ (5 mL) was added TFA (0.6 mL, 6.52 mmol) at 0° C. and stirred at RT for 3 h. After completion of reaction (by TLC), the reaction mixture was concentrated under reduced pressure to obtained crude compound which was triturated with n-pentane/diethylether (3×5 mL) to afford (2S-FNL-8) (125 mg, 67.9%) as an white solid (TFA salt).

$^1$H-NMR: (500 MHz, D$_2$O): δ 4.26 (s, 2H), 4.09 (t, J=8.0 Hz, 1H), 3.95 (t, J=7.5 Hz, 1H), 3.56-3.51 (m, 2H), 3.14-3.06 (m, 2H), 2.50-2.43 (m, 2H), 2.25-2.21 (m, 1.85-1.82 (m, 1H), 1.30 (d, J=5.5 Hz, 3H), 0.96 (d, J=7.0 Hz, 6H);

Mass (ESI): m/z 284.3 [M$^+$+1]

Scheme 2S-4:

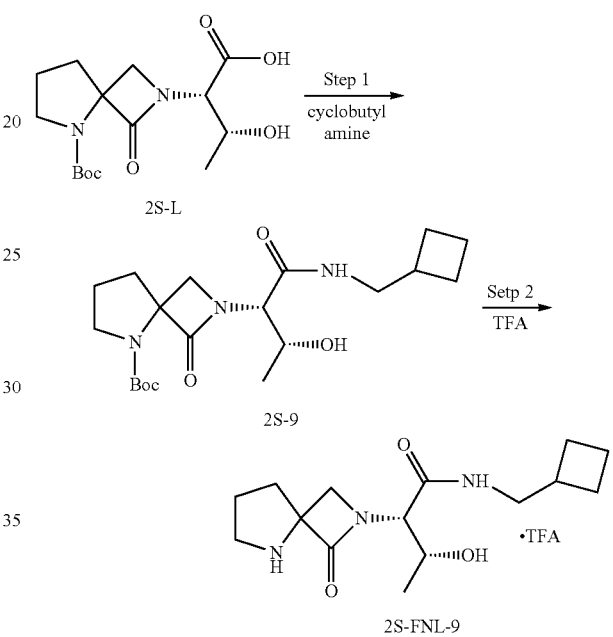

2S-L 2S-9

2S-FNL-9

Synthesis of tert-butyl 2-((2S, 3R)-1-((cyclobutylmethyl) amino)-3-hydroxy-1-oxobutan-2-yl)-1-oxo-2, 5-diazaspiro [3.4] octane-5-carboxylate (2S-9)

To a stirring solution of compound 2S-L (500 mg, 1.52 mmol) in CH$_2$Cl$_2$ (10 mL) were added DIPEA (0.8 mL, 4.57 mmol), EDCI.HCl (350 mg, 1.82 mmol) followed by HOBt (280 mg, 1.82 mmol), cyclobutylamine (155 mg, 1.82 mmol) at 0° C. and stirred for 16 h at RT. After consumption of the starting material (by TLC), the reaction mixture was diluted with water (10 mL) and the separated organic layer was washed with citric acid (2×20 mL), brine (2×20 mL). The combined organic layers were dried over anhydrous Na$_2$SO$_4$, filtered and concentrated under reduced pressure. Obtained crude material was purified by silica gel column chromatography eluting 80% EtOAc/n-hexane to afford compound 2S-9 (250 mg, 41.5%) as colorless syrup.

$^1$H-NMR: (500 MHz, DMSO-d$_6$): δ 8.20 (t, J=11.5 Hz, 1H), 4.53 (s, 2H), 4.03 (t, J=7.5 Hz, 1H), 3.88 (t, J=8.5 Hz, 2H), 3.41-3.33 (m, 2H), 3.32-3.24 (m, 2H), 2.41-2.33 (m, 3H), 2.32-2.27 (m, 2H), 2.24-2.17 (m, 2H), 2.10-1.90 (m, 2H), 1.68 (t, J=8.5 Hz, 2H), 1.40 (s, 9H), 1.18 (d, J=6.4 Hz, 3H);

Mass (ESI): m/z 396.4 [M$^+$+1]

Synthesis of (2S, 3R)—N-(cyclobutylmethyl)-3-hydroxy-2-(1-oxo-2, 5-diazaspiro [3.4] octan-2-yl) butanamide (2S-FNL-9)

To a stirring solution of compound 2S-9 (250 mg, 0.63 mmol) in CH$_2$Cl$_2$ (5 mL) was added TFA (0.5 mL, 5.06 mmol) at 0° C. and stirred at RT for 3 h. After completion of reaction (by TLC), the reaction mixture was concentrated under reduced pressure to obtained crude compound which was triturated with diethylether (5 mL) to afford (2S-FNL-9) (90 mg, 48.3%) as hygroscopic white solid (TFA salt).

$^1$H-NMR: (500 MHz, D$_2$O): δ 4.23 (s, 2H), 4.08 (t, J=7.0 Hz, 1H), 3.94 (t, J=8.5 Hz, 1H), 3.56-3.51 (m, 2H), 3.32-3.24 (m, 2H), 2.56-2.53 (m, 3H), 2.48-2.43 (m, 2H), 2.25-2.21 (m, 2H), 2.07-1.88 (m, 2H), 1.71 (t, J=8.5 Hz, 2H), 1.28 (d, J=6.4 Hz, 3H);

Mass (ESI): m/z 296.3 [M$^+$+1];

Na$_2$SO$_4$, filtered and concentrated under reduced pressure. Obtained crude material was purified by silica gel column chromatography eluting 5% MeOH/DCM to afford (2S-FNL-10) (800 mg, 63.5%) as white solid.

$^1$H-NMR: (400 MHz, CD$_3$OD): δ 7.38-7.20 (m, 5H), 4.62-4.60 (m, 1H), 4.49-4.43 (m, 2H), 4.33-4.25 (m, 1H), 4.04 (d, J=5.6 Hz, 1H), 3.96-3.92 (m, 1H), 3.51-3.45 (m, 1H), 3.43-3.31 (m, 1H), 2.31-2.21 (m, 2H), 1.98-1.86 (m, 2H), 1.39 (s, 9H), 1.24-1.22 (m, 3H);

Mass (ESI): m/z 418.4 [M$^+$+1];

HPLC: 91.8% (both isomers)

Synthesis of (2S, 3R)—N-benzyl-3-hydroxy-2-(1-oxo-2, 5-diazaspiro [3.4] octan-2-yl) butanamide (2S-FNL-11)

To a stirring solution of (2S-FNL-10) (700 mg, 1.67 mmol) in CH$_2$Cl$_2$ (10 mL) was added TFA (1.9 mL, 16.7 mmol) at 0° C. and stirred at RT for 4 h. After completion Scheme 2S-5:

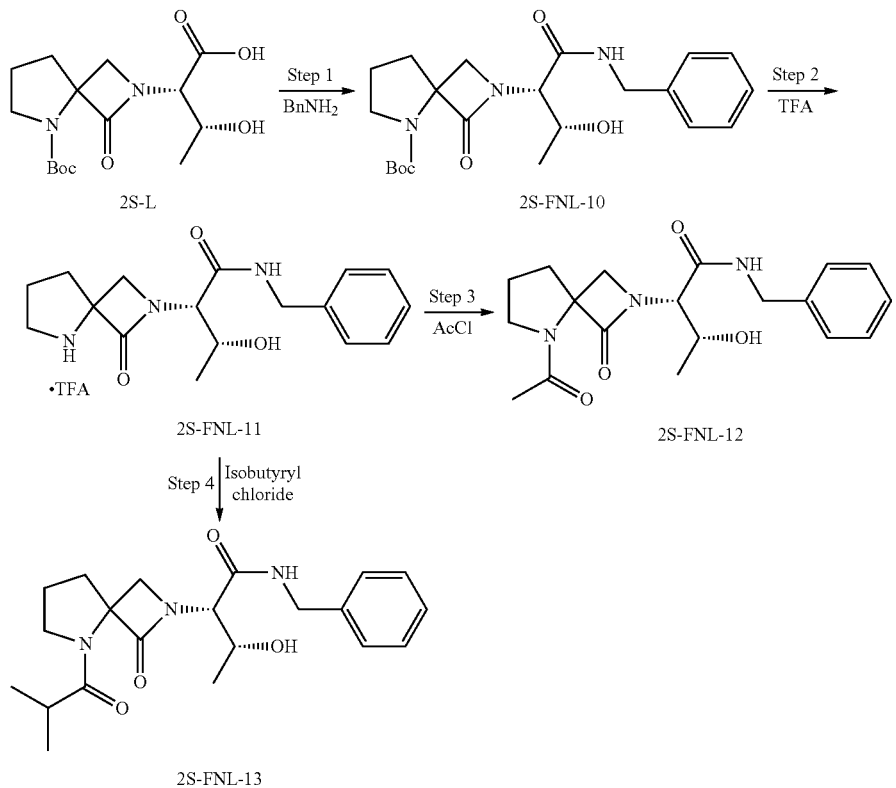

Synthesis of tert-butyl 2-((2S, 3R)-1-(benzylamino)-3-hydroxy-1-oxobutan-2-yl)-1-oxo-2, 5-diazaspiro [3.4] octane-5-carboxylate (2S-FNL-10)

To a stirring solution of compound 2S-L (1 g, 3.04 mmol) in CH$_2$Cl$_2$ (15 mL) were added DIPEA (1.6 mL, 9.14 mmol), EDCI.HCl (700 mg, 3.66 mmol) followed by HOBT (560 mg, 3.66 mmol), benzylamine (325 mg, 3.04 mmol) at 0° C. and stirred for 16 h at RT. After consumption of the starting material (by TLC), the reaction mixture was diluted with water (20 mL) and extracted with CH$_2$Cl$_2$ (2×30 mL). The combined organic layer was washed with citric acid solution (2×30 mL) and organic layer was dried over anhydrous of reaction (by TLC), the reaction mixture was concentrated under reduced pressure to obtained crude compound which was triturated with n-pentane/diethylether (5 mL/5 mL) to afford (2S-FNL-11) (400 mg, 75.6%) as an white solid (TFA salt).

$^1$H-NMR: (400 MHz, D$_2$O): δ 7.45-7.34 (m, 5H), 4.45 (s, 2H), 4.29-4.21 (m, 2H), 4.06-3.85 (m, 2H), 3.52-3.47 (m, 2H), 2.45-2.35 (m, 2H), 2.22-2.16 (m, 2H), 1.24-1.20 (m, 3H);

Mass (ESI): m/z 318.4 [M$^+$+1];

HPLC: 89.1% (both isomers).

Synthesis of (2S, 3R)-2-(5-acetyl-1-oxo-2, 5-diazaspiro [3.4] octan-2-yl)-N-benzyl-3-hydroxybutanamide (2S-FNL-12)

To a stirring solution of (2S-FNL-11) (240 mg, 0.75 mmol) in CH$_2$Cl$_2$ (10 mL) were added TEA (0.31 mL, 2.25 mmol) at RT. After added acetyl chloride (0.1 mL, 0.9 mmol) slowly at 0° C. and stirred to RT for 2 h. After consumption of the starting material (by TLC), the reaction mixture was diluted with water (5 mL) and extracted with CH$_2$Cl$_2$ (2×20 mL). The combined organic layer was washed with citric acid solution (1×20 mL), brine (1×20 mL). The separated organic layer was dried over anhydrous Na$_2$SO$_4$, filtered and concentrated under reduced pressure. Obtained crude material was purified by silica gel column chromatography eluting with 2% MeOH/DCM to afford (2S-FNL-12) (90 mg, 33.4%) as an off-white solid.

$^1$H-NMR: (400 MHz, CD$_3$OD): δ 7.32-7.20 (m, 5H), 4.58-4.55 (m, 1H), 4.52-4.42 (m, 2H), 4.36-4.22 (m, 1H), 4.08-3.93 (m, 1H), 3.70-3.65 (m, 2H), 3.64-3.53 (m, 2H), 2.32-2.22 (m, 2H), 2.20 (s, 3H), 2.04-1.95 (m, 2H), 1.22-1.20 (m, 3H);

Mass (ESI): m/z 360.3 [M$^+$+1];

HPLC: 97.5% (both isomers)

Synthesis of (2S, 3R)—N-benzyl-3-hydroxy-2-(5-isobutyryl-1-oxo-2, 5-diazaspiro [3.4] octan-2-yl) butanamide (NRX-2563) (2S-FNL-13)

To a stirring solution of (2S-FNL-11) (244 mg, 0.76 mmol) in CH$_2$Cl$_2$ (10 mL) was added TEA (0.37 mL, 2.66 mmol) at 0° C. After added Int-F (89 mg, 0.84 mmol) and stirred at RT for 2 h. After completion of reaction (by TLC), the reaction mixture was diluted with water (10 mL) and extracted with CH$_2$Cl$_2$ (2×20 mL). The combined organic layer was washed with citric acid solution (2×30 mL) and organic layer was dried over anhydrous Na$_2$SO$_4$, filtered and concentrated under reduced pressure. Obtained crude material was purified by silica gel column chromatography eluting 60% EtOAc/n-hexane to afford (2S-FNL-13) (150 mg, 51%) as an off-white solid.

$^1$H-NMR: (400 MHz, CD$_3$OD): δ 7.35-7.20 (m, 5H), 4.82-4.49 (m, 1H), 4.46-4.31 (m, 1H), 4.29-4.03 (m, 1H), 3.90-3.70 (m, 2H), 3.69-3.57 (m, 2H), 3.46-3.31 (m, 1H), 2.77-2.73 (m, 1H), 2.28-2.21 (m, 2H), 2.06-1.97 (m, 2H), 1.22 (d, J=6.8 Hz, 3H), 1.08-0.98 (m, 6H);

Mass (ESI): m/z 388.4 [M$^+$+1];

HPLC: 95.2% (both isomers)

Scheme 2S-6:

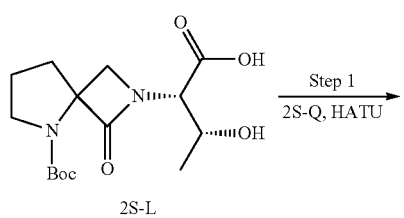

2S-L

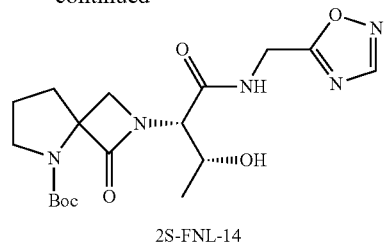

2S-FNL-14

Synthesis of tert-butyl 2-((2S, 3R)-1-(((1, 2, 4-oxadiazol-5-yl) methyl) amino)-3-hydroxy-1-oxobutan-2-yl)-1-oxo-2, 5-diazaspiro [3.4] octane-5-carboxylate (2S-FNL-14)

To a stirring solution of compound 2S-L (600 mg, 1.82 mmol) in DMF (10 mL) were added DIPEA (708 mg, 5.48 mmol), 2S-Q (290 mg, 1.82 mmol) HATU (761 mg, 2.00 mmol) at 0° C. and stirred for 16 h at RT. After consumption of the starting material (by TLC), the reaction mixture was diluted with water (50 mL) and EtOAc (100 mL). The organic layer was washed with water (2×50 mL) followed by brine solution (2×30 mL). The organic layer was dried over anhydrous Na$_2$SO$_4$, filtered and concentrated under reduced pressure. Obtained crude material was purified by silica gel column chromatography eluting 2% MeOH/DCM. The obtained solid was triturated with ether/n-pentane (5 mL/5 mL) to afford (2S-FNL-14) (100 mg, 13.5%) as white solid.

$^1$H-NMR: (400 MHz, CD$_3$OD): δ 8.61 (s, 1H), 4.85 (s, 2H), 4.78-4.63 (m, 1H), 4.59-4.55 (m, 1H), 4.30-4.25 (m, 1H), 3.52-3.46 (m, 2H), 3.43-3.29 (m, 1H), 2.31-2.23 (m, 2H), 1.96-1.88 (m, 2H), 1.45 (s, 9H), 1.26-1.20 (m, 3H);

Mass (ESI): m/z 410.4 [M$^+$+1];

HPLC: 98.14% (both isomers)

Scheme 2S-7:

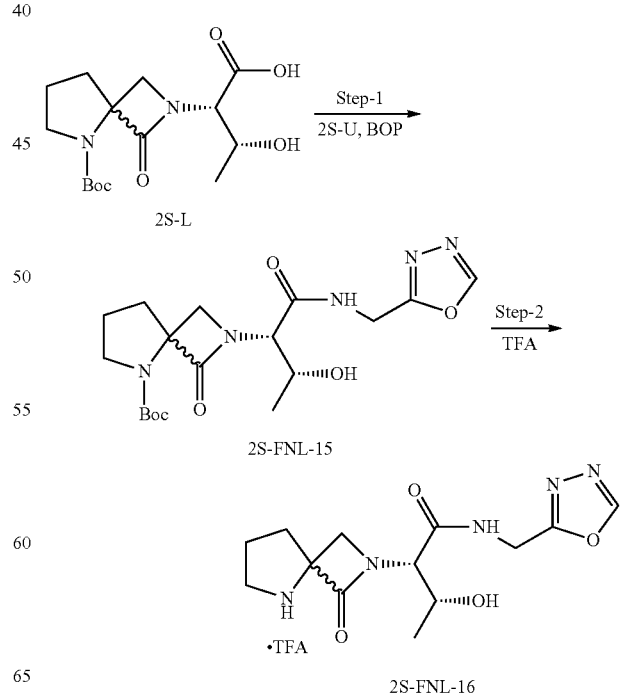

Synthesis of tert-butyl 2-((2S, 3R)-1-(((1, 3, 4-oxadiazol-2-yl) methyl) amino)-3-hydroxy-1-oxobutan-2-yl)-1-oxo-2, 5-diazaspiro [3.4] octane-5-carboxylate (2S-FNL-15)

To a stirring solution of compound 2S-L (1 g, 3.04 mmol) in DMF (10 mL) were added DIPEA (1.58 mL, 9.12 mmol), BOP reagent (2.01 g, 4.56 mmol) followed by 2S-U (496 mg, 3.64 mmol) at 0° C. and stirred for 16 h at RT. After consumption of the starting material (by TLC), the reaction mixture was diluted with water (100 mL) and extracted with EtOAc (2×30 mL). The combined organic layer was washed with brine solution (2×50 mL) and organic layer was dried over anhydrous $Na_2SO_4$, filtered and concentrated under reduced pressure. Obtained crude material was purified by silica gel column chromatography eluting 80% EtOAc/n-hexane followed by preparative HPLC purification to afford (2S-FNL-15) (67 mg, 5.4%) as an off-white solid.

$^1$H-NMR: (400 MHz, DMSO-$d_6$): δ 10.92 (s, 1H), 7.83 (s, 1H), 4.97-4.88 (m, 2H), 4.07 (d, J=7.2 Hz, 2H), 3.83-3.65 (m, 2H), 3.57-3.40 (m, 1H), 3.38-3.25 (m, 2H), 2.15-2.01 (m, 2H), 1.83-1.80 (m, 2H), 1.40 (s, 9H), 1.22 (d, J=6.4 Hz, 3H)

Mass (ESI): m/z 410.4 [M$^+$+1];

HPLC: 90.6%

Synthesis of (2S, 3R)—N-((1, 3, 4-oxadiazol-2-yl) methyl)-3-hydroxy-2-(1-oxo-2, 5-diazaspiro [3.4] octan-2-yl) butanamide (2S-FNL-16)

To a stirring solution of compound (2S-FNL-15) (70 mg, 0.71 mmol) in $CH_2Cl_2$ (5 mL) was added TFA (195 mg, 1.71 mmol) at 0° C. and stirred at RT for 1 h. After completion of reaction (by TLC), the reaction mixture was concentrated under reduced pressure to obtained crude compound which was triturated with n-pentane/diethylether (5 mL/5 mL) to afford compound (2S-FNL-16) (60 mg, 84.5%) as an off-white solid (TFA salt).

$^1$H-NMR: (400 MHz, $D_2O$): δ 7.83 (s, 1H), 5.20-5.10 (m, 1H), 4.80 (s, 1H), 4.39-4.30 (m, 2H), 4.13-4.04 (m, 2H), 3.53-3.48 (m, 2H), 2.44-2.41 (m, 2H), 2.21-2.16 (m, 2H), 1.31 (d, J=6.4 Hz, 3H); Mass (ESI): m/z 310.1 [M$^+$+1];

HPLC: 90.99%

Scheme 2S-8:

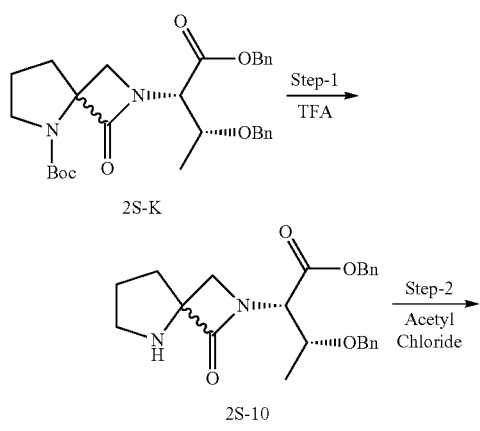

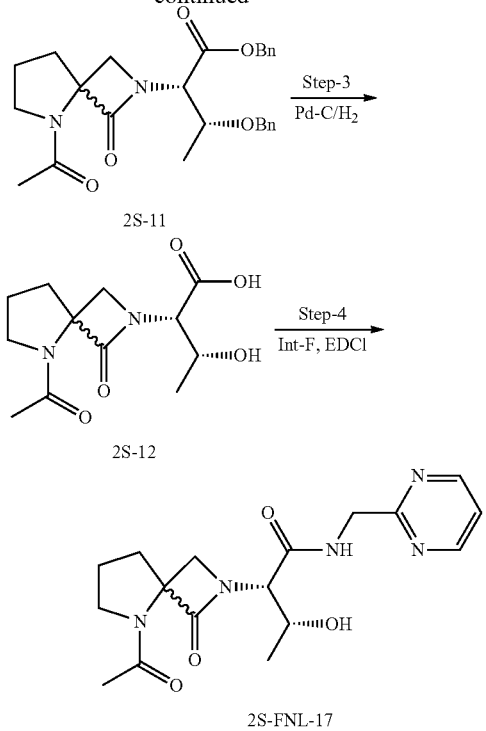

Synthesis of benzyl (2S, 3R)-3-(benzyloxy)-2-(1-oxo-2, 5-diazaspiro [3.4] octan-2-yl) butanoate (8)

To a stirring solution of compound 2S-K (800 mg, 1.57 mmol) in DCM (10 mL) was added TFA (1.2 mL) at 0° C. and stirred at RT for 2 h. After consumption of the starting material (by TLC), the reaction mixture was concentrated under reduced pressure to afford compound 2S-10 (500 mg, 78%) as an off-white solid (HCl salt) was used directly for next step.

$^1$H-NMR: (500 MHz, $D_2O$): δ 7.48 (m, 5H), 7.24-7.21 (m, 5H), 5.29 (s, 2H), 4.96 (s, 2H), 4.80-4.62 (m, 1H), 4.29-4.18 (m, 2H), 4.01-3.89 (m, 1H), 3.52-3.46 (m, 2H), 2.43-2.38 (m, 2H), 2.24-2.14 (m, 2H), 1.35-1.28 (m, 3H);

LCMS: 408 [M$^+$+1]

Synthesis of benzyl (2S, 3R)-2-(5-acetyl-1-oxo-2, 5-diazaspiro [3.4] octan-2-yl)-3-(benzyloxy) butanoate (2S-11)

To a stirring solution of compound 2S-10 (500 mg, 1.22 mmol) in DCM (5 mL) was added TEA (0.46 mL, 3.36 mmol) followed by acetyl chloride (0.1 mL, 1.47 mmol) at 0° C. and stirred at RT for 2 h. After consumption of the starting material (by TLC), reaction mixture was diluted with water (10 mL). The organic layer was dried over anhydrous $Na_2SO_4$, filtered and concentrated under reduced pressure. Obtained crude material was purified by silica gel column chromatography eluting 2% MeOH/DCM to afford compound 2S-11 (300 mg, 54.5%) as white solid.

$^1$H-NMR: (400 MHz, $CD_3OD$): 7.36-7.29 (m, 5H), 7.26-7.16 (m, 5H), 5.13 (s, 2H), 4.59 (s, 2H), 4.32-4.29 (m, 2H), 4.16-4.13 (m, 1H), 3.65-3.61 (m, 1H), 3.60-3.46 (m, 2H), 2.21-2.09 (m, 2H), 2.02 (s, 3H), 2.01-1.91 (m, 2H), 1.21 (d, J=6.4 Hz, 3H);

LCMS: 451.3 [M$^+$+1]

Synthesis of (2S, 3R)-2-(5-acetyl-1-oxo-2, 5-diazaspiro [3.4] octan-2-yl)-3-hydroxybutanoic acid (2S-12)

To a stirring solution of compound 2S-11 (1 g, 2.22 mmol) in methanol (30 mL) was added 10% Pd/C (500 mg) at RT and stirred for 24 h under $H_2$ atmosphere. After consumption of the starting material (by TLC), the reaction mixture was filtered through a pad of celite and the pad was washed with methanol (20 mL). Obtained filtrate was concentrated under reduced pressure to afford compound 2S-12 (500 mg, 83.3%) as an off-white solid.

$^1$H-NMR: (400 MHz, $CD_3OD$): δ 4.35-4.30 (m, 1H), 4.29-4.17 (m, 1H), 4.09-4.04 (m, 1H), 3.76-3.67 (m, 1H), 3.59-3.48 (m, 1H), 3.34-3.31 (m, 1H), 2.29-2.24 (m, 2H), 2.15 (s, 3H), 2.04-1.96 (m, 2H), 1.28 (d, J=6.4 Hz, 3H);
LCMS m/z: 270.4 [M$^+$+1]

Synthesis of (2S, 3R)-2-(5-acetyl-1-oxo-2, 5-diazaspiro [3.4] octan-2-yl)-3-hydroxy-N-(pyrimidin-2-ylmethyl) butanamide (2S-FNL-17)

To a stirring solution of compound 2S-12 (700 mg, 2.59 mmol) in DCM (15 mL) were added DIPEA (1.35 mL, 7.77 mmol), 2S-Y (410 mg, 2.84 mmol), EDCI (593 mg, 3.1 mmol) followed by HOBT (474 mg, 3.1 mmol) at 0° C. and stirred for 16 h at RT. After consumption of the starting material (by TLC), the reaction mixture was diluted with water (40 mL). The organic layer was dried over anhydrous $Na_2SO_4$, filtered and concentrated under reduced pressure. Obtained crude material was purified by silica gel column chromatography eluting 3% MeOH/DCM to afford (2S-FNL-17) (100 mg, 10.7%) as white solid.

$^1$H-NMR: (400 MHz, $D_2O$): δ 8.78 (d, J=5.2 Hz, 2H), 7.49 (t, J=5.2 Hz, 1H), 4.79 (s, 2H), 4.55-4.47 (m, 1H), 4.40-4.37 (m, 2H), 3.79-3.56 (m, 3H), 2.37-2.26 (m, 2H), 2.14-2.03 (m, 2H), 2.01 (s, 3H), 1.28 (d, J=6.4 Hz, 3H);
Mass (ESI): m/z 362.4 [M$^+$+1];
HPLC: 92.3% (both isomers)

Scheme 2S-9:

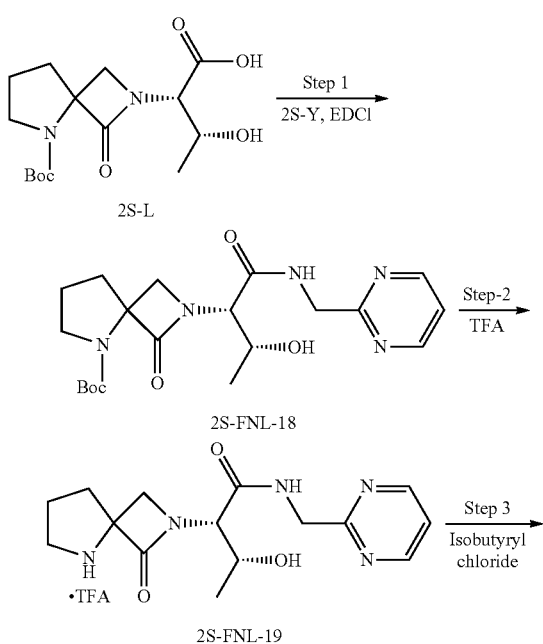

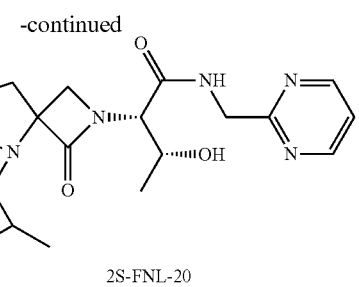

2S-FNL-20

Synthesis of tert-butyl 2-((2S, 3R)-3-hydroxy-1-oxo-1-((pyrimidin-2-ylmethyl) amino) butan-2-yl)-1-oxo-2, 5-diazaspiro [3.4] octane-5-carboxylate (2S-FNL-18)

To a stirring solution of compound 2S-L (1 g, 3.04 mmol) in $CH_2Cl_2$ (30 mL) were added DIPEA (1.63 mL, 9.14 mmol), EDCI.HCl (696 mg, 3.64 mmol) followed by HOBT (558 mg, 3.64 mmol), 2S-Y (241 mg, 3.34 mmol) at 0° C. and stirred for 16 h at RT. After consumption of the starting material (by TLC), the reaction mixture was diluted with water (30 mL). The organic layer was washed with citric acid solution (2×30 mL) followed by brine solution (2×25 mL). The organic layer was dried over anhydrous $Na_2SO_4$, filtered and concentrated under reduced pressure. Obtained crude material was purified by silica gel column chromatography eluting 5% MeOH/DCM to afford (2S-FNL-18) (800 mg, 63%) as white solid.

$^1$H-NMR: (400 MHz, $CD_3OD$): δ 8.72 (t, J=4.8 Hz, 2H), 7.36 (t, J=4.8 Hz, 1H), 4.81-4.76 (m, 1H), 4.62-4.49 (m, 1H), 4.34-4.29 (m, 1H), 4.18-4.03 (m, 2H), 3.56 (d, J=5.6 Hz, 2H), 3.52-3.46 (m, 1H), 2.30-2.25 (m, 2H), 1.97-1.88 (m, 2H), 1.46 (s, 9H), 1.31-1.28 (m, 3H);
Mass (ESI): m/z 420.4 [M$^+$+1];
HPLC: 99.6% (both isomers)

Synthesis of (2S, 3R)-3-hydroxy-2-(1-oxo-2, 5-diazaspiro [3.4] octan-2-yl)-N-(pyrimidin-2-ylmethyl) butanamide (2S-FNL-19)

To a stirring solution of (2S-FNL-18) (280 mg, 0.66 mmol) in $CH_2Cl_2$ (5 mL) was added TFA (0.3 mL, 4.0 mmol) at 0° C. and stirred at RT for 4 h. After completion of reaction (by TLC), the reaction mixture was concentrated under reduced pressure to obtained crude compound that was triturated with n-pentane/diethyl ether (5 mL/5 mL) to afford (2S-FNL-19) (95 mg, 44.6%) as an white solid (TFA salt).

$^1$H-NMR: (500 MHz, $D_2O$): δ 8.81 (d, J=4.5 Hz, 2H), 7.53 (t, J=5.0 Hz, 1H), 4.80-4.65 (m, 2H), 4.46 (d, J=6.0 Hz, 1H), 4.36-4.31 (m, 2H), 4.10 (d, J=7.5 Hz, 1H), 3.95 (t, J=8.0 Hz, 1H), 3.58-3.49 (m, 1H), 2.51-2.40 (m, 2H), 2.26-2.17 (m, 2H), 1.34 (d, J=6.0 Hz, 3H);
Mass (ESI): m/z 320.3 [M$^+$+1]

Synthesis of (2S, 3R)-3-hydroxy-2-(5-isobutyryl-1-oxo-2, 5-diazaspiro [3.4] octan-2-yl)-N-(pyrimidin-2-ylmethyl) butanamide (2S-FNL-20)

To a stirring solution of (2S-FNL-19) (300 mg, 0.94 mmol) in $CH_2Cl_2$ (5 mL) was added TEA (0.4 mL, 2.82 mmol) followed by SM-4 (120 mg, 1.12 mmol) at 0° C. and stirred at RT for 2 h. After completion of reaction (by TLC), the reaction mixture was diluted with water (10 mL) and extracted with CH$_2$Cl$_2$ (2×20 mL). The combined organic layer was dried over anhydrous Na$_2$SO$_4$, filtered and concentrated under reduced pressure. Obtained crude material was purified by silica gel column chromatography eluting 2% MeOH/DCM to afford (2S-FNL-20) (100 mg, 27.3%) as white solid.

$^1$H-NMR: (400 MHz, CD$_3$OD): δ 8.73 (t, J=5.2 Hz, 2H), 7.36 (t, J=4.8 Hz, 1H), 4.83-4.55 (m, 1H), 4.51-4.29 (m, 3H), 4.21-4.02 (m, 1H), 3.75-3.69 (m, 1H), 3.64-3.60 (m, 1H), 3.31-3.30 (m, 1H), 2.79-2.72 (m, 1H), 2.28-2.25 (m, 2H), 2.08-1.97 (m, 2H), 1.31 (d, J=6.4 Hz, 3H), 1.07-1.02 (m, 6H).

Mass (ESI): m/z 390.4 [M$^+$+1],

HPLC: 97.75%

Scheme 2S-10:

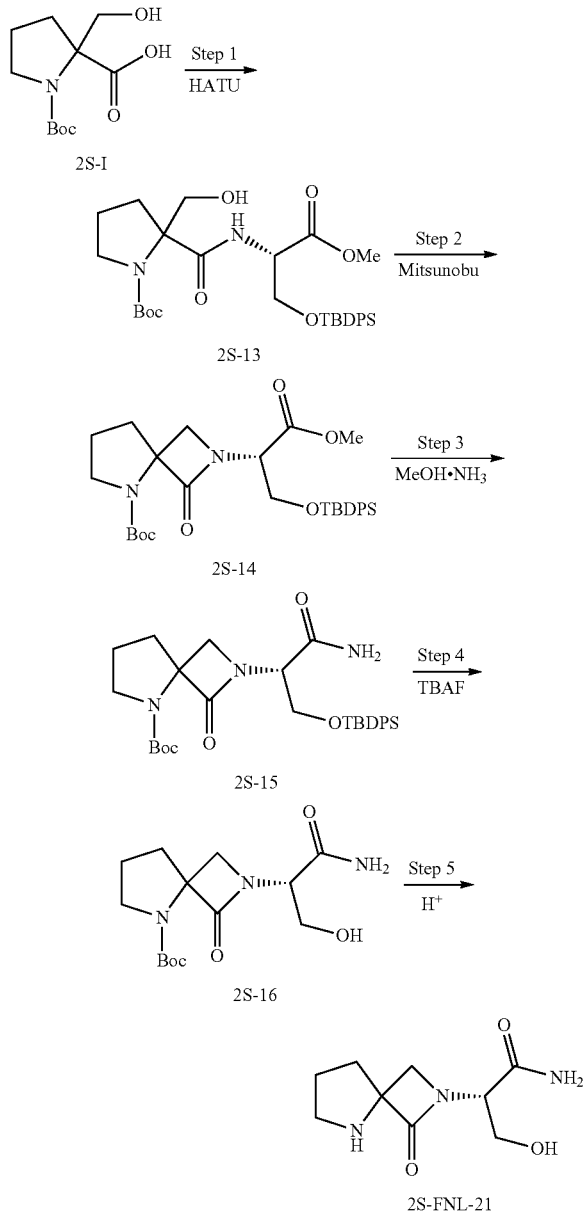

tert-Butyl 2-(((S)-3-((tert-butyldiphenylsilyl)oxy)-1-methoxy-1-oxopropan-2-yl)carbamoyl)-2-(hydroxymethyl)pyrrolidine-1-carboxylate (2S-13)

To a stirring solution of compound 2S-I (11 g, 44.89 mmol) in CH$_2$Cl$_2$ (110 mL) was added compound 2S-AJ (16.07 g, 44.89 mmol), HATU (20.4 g, 53.68 mmol) followed by DIPEA (17.37 g, 0.13 mol) at RT and stirred for 10 h. After consumption of the starting material (by TLC), the reaction mixture was diluted with water (100 mL) and extracted with CH$_2$Cl$_2$ (2×100 mL). The separated organic layer was washed with brine, dried over anhydrous Na$_2$SO$_4$, filtered and concentrated under reduced pressure. Obtained crude material was purified by silica gel column chromatography to afford compound 2S-13 (16 g, 61%) as yellow liquid.

$^1$H-NMR: (500 MHz, CDCl$_3$): δ 7.58-7.37 (m, 10H), 4.67 (s, 1H), 4.12-4.08 (m, 2H), 3.93 (s, 1H), 3.75 (s, 3H), 3.72-3.64 (m, 2H), 2.8 (s, 1H), 2.35 (s, 1H), 2.04 (s, 1H), 1.98-1.82 (m, 3H), 1.25 (s, 9H), 1.03 (s, 9H);

Mass (ESI): m/z 583.5[M$^+$−1].

Synthesis of tert-butyl 2-((S)-3-((tert-butyldiphenylsilyl)oxy)-1-methoxy-1-oxopropan-2-yl)-1-oxo-2,5-diazaspiro[3.4]octane-5-carboxylate (2S-14)

To a stirring solution of compound 2S-13 (1.6 g, 2.73 mmol) in THF (20 mL) was added triphenylphosphine (0.994 g, 4.10 mmol) and DTAD (0.788 g, 3.00 mmol). The reaction mixture was stirred at RT for 8 h. After consumption of the starting material (by TLC), the reaction mixture was diluted with water and extracted with EtOAc (2×30 mL). The separated organic layer was dried over anhydrous Na$_2$SO$_4$, filtered and concentrated under reduced pressure. The crude material was purified by silica gel column chromatography to afford compound 2S-14 (0.8 g, 51%) as yellow sticky compound.

$^1$H-NMR: (400 MHz, CDCl$_3$): δ 7.63-7.58 (m, 4H), 7.45-7.30 (m, 6H), 4.1 (s, 3H), 3.80-3.67 (m, 4H), 3.56-3.44 (m, 3H), 2.04-1.95 (m, 4H), 1.59 (s, 9H), 1.04 (s, 9H).

Mass (ESI): m/z 567.4 [M$^+$+1]

Synthesis of tert-butyl 2-((S)-1-amino-3-((tert-butyldiphenylsilyl)oxy)-1-oxopropan-2-yl)-1-oxo-2,5-diazaspiro[3.4]octane-5-carboxylate (2S-15)

To a stirring solution of compound 2S-14 (6 g) in methanol (50 mL) was added methanolic ammonia (50 mL)) at 0° C. and stirred for 12 h at RT. After consumption of the starting material (by TLC), the reaction mixture was concentrated under reduced pressure and purified the crude residue by silica gel column chromatography eluting 40% EtOAc:hexane to afford compound-2S-15 (1 g, 17%) as an pale yellow solid.

$^1$H-NMR: (400 MHz, CDCl$_3$): δ 8.27 (s, 1H), 7.67-7.63 (m, 4H), 7.45-7.36 (m, 7H), 5.37 (s, 1H), 4.56-4.54 (m, 1H), 3.82 (d, J=5.2 Hz, 1H), 3.44 (t, J=7.6 Hz, 2H), 3.35 (d, J=5.2 Hz, 1H), 3.21 (s, 1H), 2.09-2.06 (m, 2H), 2.03 (d, J=4.8 Hz, 2H), 1.44 (s, 9H), 1.08 (s, 9H).

LCMS (M/Z) m/z: 214 [M$^+$+1].

Synthesis of tert-butyl 2-((S)-1-amino-3-hydroxy-1-oxopropan-2-yl)-1-oxo-2,5-diazaspiro[3.4]octane-5-carboxylate (2S-16)

To a stirring solution of compound 2S-15 (1 g, 1.81 mmol) in THF (10 mL) was added TBAF (0.943 g, 3.62 mmol) at 0° C. and the reaction mixture was slowly warmed to RT and stirred for 2 h. After consumption of the starting material (by TLC), the reaction mixture was diluted with water (5 mL) and extracted with EtOAc (2×15 mL). The separated organic layer was washed with brine, dried over anhydrous Na₂SO₄, filtered and concentrated under reduced pressure. Obtained crude material was purified by silica gel column chromatography by eluting 3% MeOH:DCM to afford 2S-16 (0.13 g, 23%) as white solid.

¹H-NMR: (400 MHz, D₂O): δ 4.53 (t, J=6.8 Hz, 1H), 4.03 (d, J=4.8, 1H), 3.96-3.91 (m, 2H), 3.85 (t, J=5.8 Hz, 1H), 3.82 (s, 2H), 2.30 (t, J=4 Hz, 2H), 2.15-1.82 (m, 2H), 1.49 (s, 9H).
LCMS (M/Z) m/z: 314.2 [M⁺+1]

Synthesis of (2S)-3-hydroxy-2-(1-oxo-2, 5-diazaspiro[3.4]octan-2-yl)propanamide (2S-FNL-21)

To a stirring solution of 2S-16 (0.13 g, 0.415 mmol) in CH₂Cl₂ (3 mL) was added TFA (1 mL) at 0° C. and stirred at RT for 2 h. The reaction mixture was concentrated under reduced pressure to afford (2S-FNL-21) (100 mg, crude) as TFA salt.

¹H-NMR: (400 MHz, D₂O): δ 4.58 (t, J=5.8 Hz, 1H), 4.09-4.03 (m, 3H), 3.92 (d, J=7.2 Hz, 1H), 3.57-3.52 (m, 2H), 2.55-2.41 (m, 2H), 2.28-2.19 (m, 2H);
LCMS (M/Z) m/z: 214 [M⁺+1].

Scheme 2S-11:

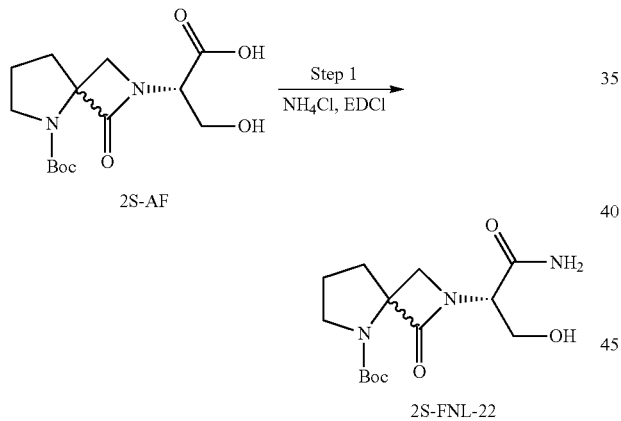

2S-AF

2S-FNL-22

Synthesis of tert-butyl 2-((S)-1-amino-3-hydroxy-1-oxopropan-2-yl)-1-oxo-2, 5-diazaspiro [3.4] octane-5-carboxylate (2S-FNL-22)

To a stirring solution of compound 2S-AF (250 mg, 0.79 mmol) in DCM (10 mL) were added DIPEA (0.5 mL, 2.38 mmol), EDCI (181 mg, 0.94 mmol), HOBT (127 mg, 0.94 mmol) followed by NH₄Cl (84.5 mg, 1.58 mmol) at 0° C. and stirred to RT for 12 h. After consumption of the starting material (by TLC), the reaction mixture was diluted with water (20 mL) and washed with citric acid (1×30 mL) followed by brine solution (1×30 mL). The organic layer was dried over anhydrous Na₂SO₄, filtered and concentrated under reduced pressure. Obtained crude material was purified by silica gel column chromatography eluting with 5% MeOH/DCM to afford (2S-FNL-22) (150 mg, 60.7%) as yellow thick syrup.

¹H-NMR: (400 MHz, CD₃OD): δ 4.13-4.07 (m, 2H), 3.96-3.88 (m, 1H), 3.87-3.77 (m, 1H), 3.63-3.47 (m, 2H), 3.44-3.30 (m, 1H), 2.31-2.26 (m, 2H), 1.97-1.88 (m, 2H), 1.47 (s, 9H);
LCMS (ESI): m/z 314.3 [M⁺+1];
HPLC: 98.38%

Scheme 2S-12:

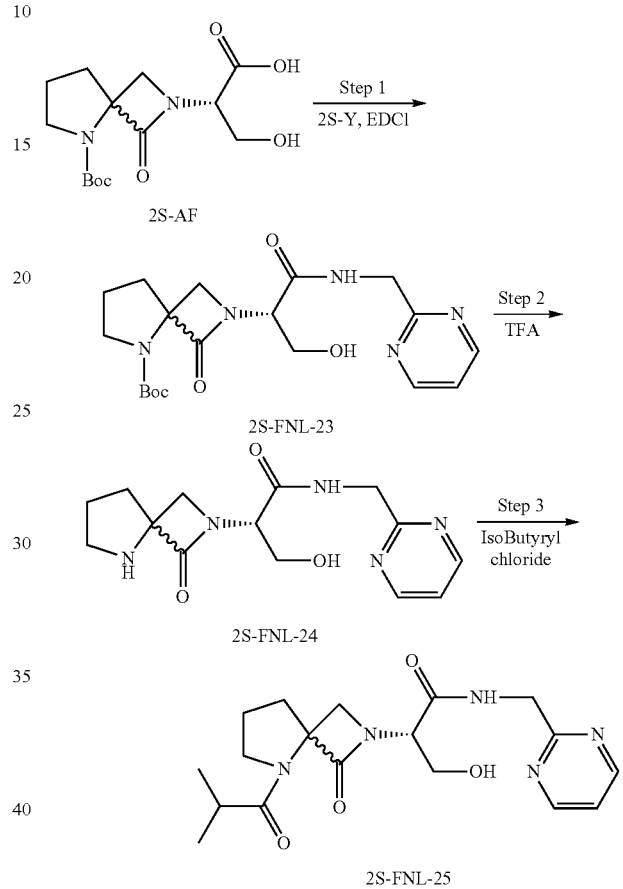

Synthesis of tert-butyl 2-((S)-3-hydroxy-1-oxo-1-((pyrimidin-2-ylmethyl) amino) propan-2-yl)-1-oxo-2, 5-diazaspiro [3.4] octane-5-carboxylate (2S-FNL-23)

To a stirring solution of compound 2S-AF (1.3 g, 4.14 mmol) in DCM (25 mL) were added DIPEA (2.15 mL, 12.42 mmol), HOBT (760 mg, 4.96 mmol), EDCI (1 g, 4.96 mmol) followed by 2S-Y (715 mg, 4.96 mmol) at 0° C. and stirred for 16 h at RT. After consumption of the starting material (by TLC), the reaction mixture was diluted with water (50 mL). The organic layer was washed with citric acid (1×30 mL) followed by bicarbonate solution (1×30 mL). The organic layer was dried over anhydrous Na₂SO₄, filtered and concentrated under reduced pressure. Obtained crude material was purified by silica gel column chromatography eluting with 2% MeOH/DCM to afford (2S-FNL-23) (800 mg, 50%) as white solid.

¹H-NMR: (400 MHz, CD₃OD): δ 8.75-8.71 (m, 2H), 7.37-7.34 (m, 1H), 4.66-4.49 (m, 2H), 4.27-4.24 (m, 1H), 4.19-4.14 (m, 1H), 4.03-3.99 (m, 1H), 3.97-3.92 (m, 1H), 3.66-3.54 (m, 1H), 3.49-3.45 (m, 1H), 3.40-3.36 (m, 1H), 2.32-2.27 (m, 2H), 1.97-1.88 (m, 2H), 1.47 (s, 9H);

Mass (ESI): m/z 406.4 [M$^+$+1].

HPLC: 97.1%

Synthesis of (2S)-3-hydroxy-2-(1-oxo-2, 5-diazaspiro [3.4] octan-2-yl)-N-(pyrimidin-2-ylmethyl) propanamide (2S-FNL-24)

To a stirring solution of compound (2S-FNL-23) (350 mg, 0.86 mmol) in DCM (5 mL) was added TFA (985 mg, 0.86 mmol) at 0° C. and stirred to RT for 3 h. The reaction mixture was brought to RT and concentrated under vacuum to afford (2S-FNL-24) (250 mg, 95.4%) as white solid.

The organic layer was dried over anhydrous Na$_2$SO$_4$, filtered and concentrated under reduced pressure. Obtained crude material was purified by silica gel column chromatography eluting with 5% MeOH/DCM to afford (2S-FNL-25) (100 mg, 16.3%) as white solid.

$^1$H-NMR: (400 MHz, CD$_3$OD): δ 8.73 (t, J=4.8 Hz, 2H), 7.37 (d, J=5.2 Hz, 1H), 4.56-4.51 (m, 2H), 4.32-4.29 (m, 1H), 4.17-4.12 (m, 1H), 4.05-3.98 (m, 2H), 3.74-3.68 (m, 1H), 3.63-3.58 (m, 1H), 3.57-3.51 (m, 1H), 2.77-2.69 (m, 1H), 2.31-2.26 (m, 2H), 2.08-1.95 (m, 2H), 1.05-0.98 (m, 6H);

LCMS: m/z 376.4 [M$^+$+1];

HPLC: 89.6% (both isomers)

Scheme 2S-13:

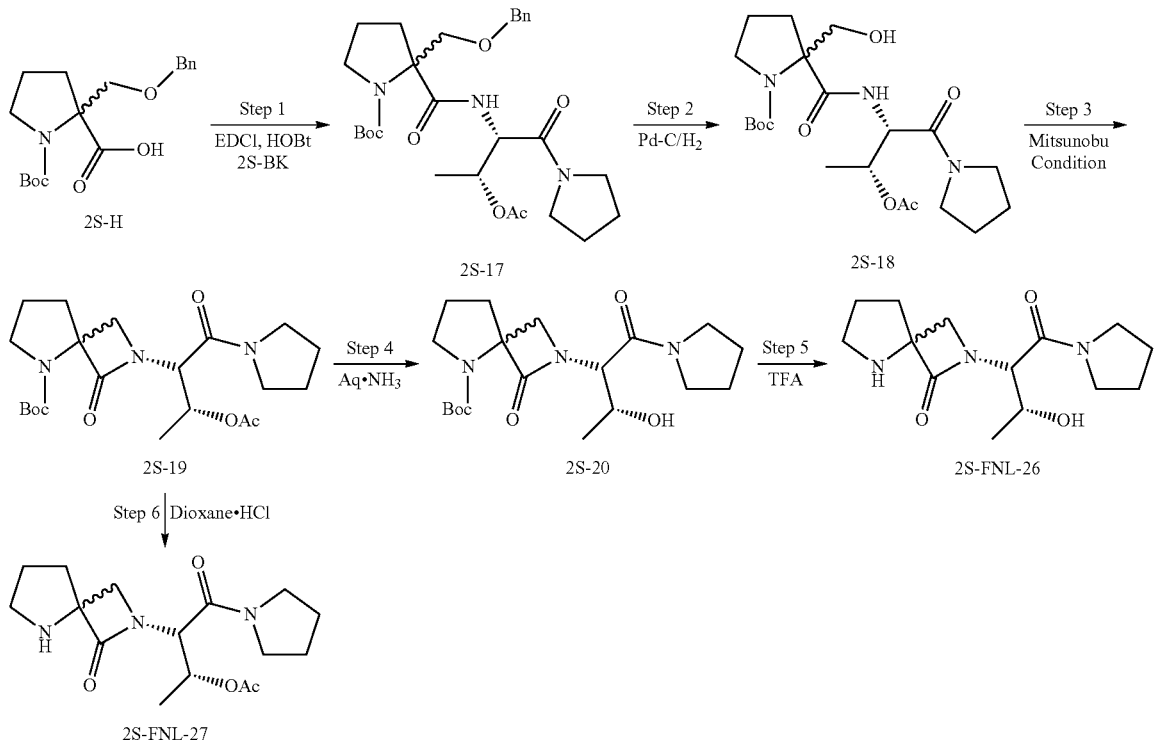

$^1$H-NMR: (400 MHz, D$_2$O): δ 8.84 (d, J=5.2 Hz, 2H), 7.55 (t, J=4.8 Hz, 1H), 4.90-4.67 (m, 3H), 4.10-4.06 (m, 3H), 3.94-3.92 (m, 1H), 3.57-3.51 (m, 2H), 2.54-2.43 (m, 2H), 2.28-2.19 (m, 2H);

LCMS: m/z 306.4 [M$^+$+1];

HPLC: 90.07%.

Synthesis of (2S)-3-hydroxy-2-(5-isobutyryl-1-oxo-2, 5-diazaspiro [3.4] octan-2-yl)-N-(pyrimidin-2-ylmethyl) propanamide (2S-FNL-25)

To a stirring solution of compound (2S-FNL-24) (500 mg, 1.63 mmol) in DCM (5 mL) was added TEA (0.7 mL, 4.91 mmol) at 0° C. After added Int-F (207 mg, 1.95 mmol) slowly and stirred to RT for 3 h. After consumption of the starting material (by TLC), the reaction mixture was diluted with water (20 mL). The organic layer was washed with citric acid (1×30 mL) followed by brine solution (1×30 mL).

Synthesis of tert-butyl 2-(((2S,3R)-3-acetoxy-1-oxo-1-(pyrrolidin-1-yl)butan-2-1)carbamoyl)-2-((benzyloxy)methyl)pyrrolidine-1-carboxylate (2S-17)

To a stirring solution of compound 2S-BK (1 g, 2.90 mmol) in DMF (8 mL) was added EDCI.HCl (0.63 g, 3.28 mmol) followed by HOBt (0.44 g, 3.28 mmol) at 0° C. After being stirred for 5 min, DIPEA (1.3 mL, 7.46 mmol) followed by compound 2S-H (0.74 g, 3.58 mmol) was added to the reaction mixture and stirring was continued for another 16 h at RT. The reaction mixture was washed with water and extracted with EtOAc (2×500 mL). The organic layer was washed with brine, dried over anhydrous Na$_2$SO$_4$ and concentrated under vacuum. The crude was purified by column chromatography to afford compound 2S-17 (0.6 g, 38%).

$^1$H-NMR: (400 MHz, CDCl$_3$) (Rotamers): δ7.34 (s, 5H), 5.37-5.34 (m, 1H), 4.84-4.80 (m, 1H), 4.72-4.65 (m, 2H), 4.09-4.02 (m, 1H), 3.91-3.87 (m, 1H), 3.65-3.61 (m, 3H), 3.52-3.46 (m, 3H), 2.41 (br s, 1H), 2.22-2.15 (m, 1H), 1.98 (d, 5H), 1.87-1.84 (m, 4H), 1.50-1.42 (m, 9H).
LCMS m/z: 532 [M⁺+1].

Synthesis of tert-butyl 2-(((2S,3R)-3-acetoxy-1-oxo-1-(pyrrolidin-1-yl)butan-2-1)carbamoyl)-2-(hydroxymethyl)pyrrolidine-1-carboxylate (2S-18)

To a stirring solution of compound 2S-17 (4.5 g, 8.40 mmol) in MeOH (40 mL) was added wet 10% Pd/C (1.5 g) under inert atmosphere and stirred for 4 h under H₂ atmosphere (balloon pressure). The reaction mixture was filtered through celite pad and concentrated under reduced pressure to afford compound 2S-18 (3.0 g, 81%).
LCMS m/z: 442.5 [M⁺+1].

Synthesis of tert-butyl 2-((2S,3R)-3-acetoxy-1-oxo-1-(pyrrolidin-1-yl)butan-2-yl)-1-oxo-2,5-diazaspiro[3.4]octane-5-carboxylate (2S-19)

To a stirring solution of compound 2S-18 (3 g, 6.70 mmol) in THF (25 mL) was added triphenylphosphine (2 g, 7.40 mmol) followed by DTAD (2.5 g, 10.2 mmol). The reaction mixture was stirred at RT for 16 h. After consumption of the starting material (by TLC), the reaction was concentrated under reduced pressure. The crude material was purified by silica gel column chromatography eluting with 10% MeOH/CH₂Cl₂ to afford compound 2S-19 (1.2 g with TPPO, 43%).
¹H-NMR: (400 MHz, DMSO-d₆): δ 5.25-5.19 (m, 1H), 4.65 (d, 1H), 3.61-3.57 (m, 3H), 3.47-3.42 (m, 2H), 3.41-3.25 (m, 4H), 2.05 (s, 4H), 1.95-1.71 (m, 7H), 1.42 (s, 10H).
LCMS m/z: 424.4 [M⁺+1].

Synthesis of tert-butyl 2-((2S, 3R)-3-hydroxy-1-oxo-1-(pyrrolidin-1-yl) butan-2-yl)-1-oxo-2, 5-diazaspiro [3.4] octane-5-carboxylate (2S-20)

A solution of compound 2S-19 (0.15 g, 0.41 mmol) in aqueous NH₃ (2 mL) was stirred at RT for 4 h. After consumption of the starting material (by TLC), the reaction diluted with CH₂Cl₂ (75 mL). The separated organic layer was dried over anhydrous Na₂SO₄ and concentrated under reduced pressure to afford compound 2S-20 (0.1 g, 76%).
LCMS m/z: 382 [M⁺+1].

Synthesis of 2-((2S,3R)-3-hydroxy-1-oxo-1-(pyrrolidin-1-yl)butan-2-yl)-2,5 diazaspiro[3.4] octan-1-one. (2S-FNL-26)

To a stirring solution of compound 2S-20 (0.2 g, 0.63 mmol) in CH₂Cl₂ (2 mL) was added TFA (0.3 mL) at 0° C. and stirred at RT for 1 h. The reaction mixture was concentrated under vacuum. Obtained residue was diluted with water and extracted with CH₂Cl₂ (2×25 mL). The separated organic layer was dried over anhydrous Na₂SO₄, filtered and concentrated under vacuum to afford (2S-FNL-26) (0.2 g, 80%) as TFA salt.
¹H-NMR: (400 MHz, D₂O): δ 4.64 (t, 1H), 4.25-4.21 (m, 1H), 4.09 (d, 1H), 3.99-3.87 (m, 1H), 3.70 (t, 2H), 3.55-3.47 (m, 5H), 2.52-2.34 (m, 2H), 2.25-2.22 (m, 2H), 2.08-1.98 (m, 5H), 1.25 (t, 3H).
LCMS (ESI) m/z: 282.4 [M⁺+1].

Synthesis of (2R, 3S)-4-oxo-3-(1-oxo-2, 5-diazaspiro [3.4] octan-2-yl)-4-(pyrrolidin-1-yl) butan-2-yl acetate (2S-FNL-27)

A stirring solution of compound 2S-19 (0.4 g, 0.94 mmol) in 1,4-dioxane/HCl (5 mL) was cooled to 0° C. and stirred at RT for 1 h. After consumption of the starting material (by TLC), the reaction mixture was concentrated under reduced pressure. Obtained crude material was washed with n-pentane followed by EtOAc to afford (2S-FNL-27) (0.22 g, 65%).
¹H-NMR: (400 MHz, D₂O): δ 4.62 (d, 1H), 4.41-4.29 (m, 2H), 4.24 (d, 1H), 3.89-3.77 (m, 3H), 3.54-3.49 (m, 3H), 2.57-2.52 (m, 1H), 2.49 (s, 3H), 2.42-2.00 (m, 8H), 1.30 (d, 3H).
LCMS m/z: 324.3 [M⁺+1].
HPLC Purity: 99.37%.

Scheme 2S-14:

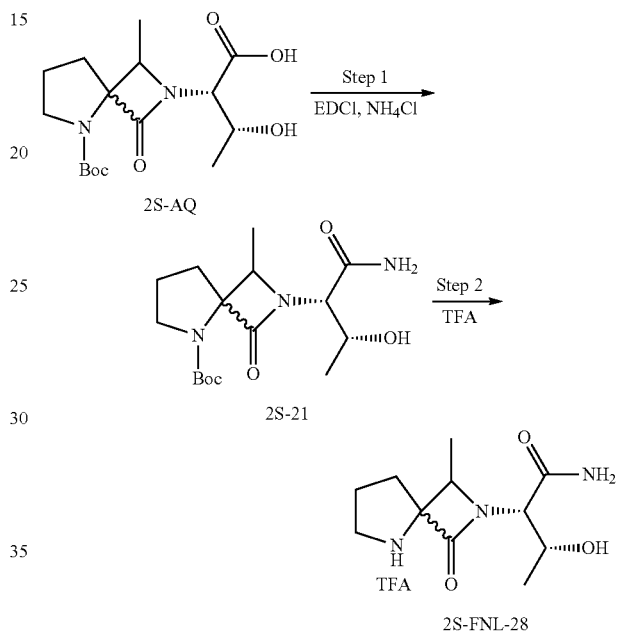

Synthesis of tert-butyl 2-((2S,3R)-1-amino-3-hydroxy-1-oxobutan-2-yl)-6-methyl-1-oxo-2,5-diazaspiro[3.4]octane-5-carboxylate (2S-21)

To a stirring solution of compound 2S-AQ (480 mg, 1.40 mmol) in CH₂Cl₂ (15 mL) were added DIPEA (543 mg, 4.20 mmol), EDCl.HCl (382 mg, 2.0 mmol) followed by HOBt (280 mg, 2.0 mmol), NH₄Cl (111 mg, 2.0 mmol) at 0° C. and stirred at RT for 16 h. After consumption of the starting material (by TLC), the reaction mixture was diluted with water (20 mL) and extracted with CH₂Cl₂ (2×30 mL). The combined organic layer was washed with brine (2×50 mL), dried over anhydrous Na₂SO₄, filtered and concentrated under reduced pressure. Obtained crude material was purified by silica gel column chromatography eluting 2% MeOH/DCM to afford compound 2S-21 (150 mg, 31%) as colorless thick syrup.
¹H-NMR: (500 MHz, DMSO-d₆): δ5.00-4.88 (m, 1H), 4.05-3.94 (m, 4H), 3.37 (t, J=10.5 Hz, 2H), 2.10-1.93 (m, 4H), 1.45 (s, 9H), 1.39-1.27 (m, 1H), 1.24-1.16 (m, 6H); Mass (ESI): m/z 364.3 [M⁺+Na]

Synthesis of (2S, 3R)-3-hydroxy-2-(1-methyl-3-oxo-2, 5-diazaspiro [3.4] octan-2-yl) butanamide (2S-FNL-28)

To a stirring solution of compound 2S-21 (150 mg, 0.43 mmol) in CH₂Cl₂ (5 mL) was added TFA (0.4 mL, 4.39 mmol) at 0° C. and stirred at RT for 2 h. After completion of reaction (by TLC), the reaction mixture was concentrated under reduced pressure to obtained crude compound which was triturated with diethylether/n-pentane (5 mL/5 mL) to afford (2S-FNL-28) (100 mg, 65.7%) as sticky solid (TFA salt). HPLC (purity): 99.7%

¹H-NMR: (400 MHz, D₂O): δ4.50-4.46 (m, 3H), 3.63-3.49 (m, 2H), 2.56-2.49 (m, 2H), 2.35-2.29 (m, 2H), 1.57 (d, J=6.8 Hz, 3H), 1.36 (d, J=6.0 Hz, 3H);

Mass (ESI): m/z 483.1 [2M⁺+1]

Scheme 2S-15:

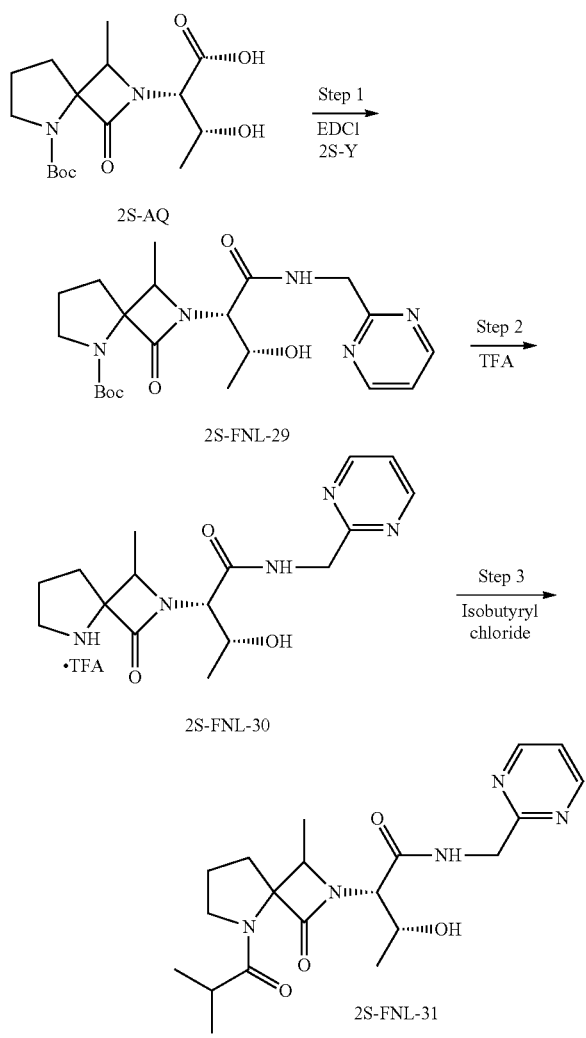

Synthesis of tert-butyl 2-((2R, 3S)-3-hydroxy-1-oxo-1-((pyrimidin-2-ylmethyl) amino) butan-2-yl)-1-methyl-3-oxo-2, 5-diazaspiro [3.4] octane-5-carboxylate (2S-FNL-29)

To a stirring solution of compound 2S-AQ (500 mg, 1.46 mmol) in CH₂Cl₂ (15 mL) were added DIPEA (0.76 mL, 4.38 mmol), EDCI.HCl (334 mg, 1.75 mmol), HOBt (334 mg, 1.75 mmol) followed by 2S-Y (252 mg, 1.75 mmol) at 0° C. and stirred at RT for 16 h. After consumption of the starting material (by TLC), the reaction mixture was diluted with water (20 mL) and extracted with CH₂Cl₂ (2×30 mL). The combined organic layer was washed with citric acid solution (20 mL), NaHCO3 (1×30 mL) followed by brine (1×50 mL). The organic layer was dried over anhydrous Na₂SO₄, filtered and concentrated under reduced pressure. Obtained crude material was purified by silica gel column chromatography eluting 2% MeOH/DCM to afford (2S-FNL-29) (200 mg, 31.6%) as white solid.

¹H-NMR: (400 MHz, CD₃OD): δ 8.74-8.70 (m, 2H), 7.37-7.32 (m, 1H), 4.72-4.43 (m, 3H), 4.24-4.14 (m, 1H), 4.10-3.88 (m, 2H), 3.52-3.36 (m, 2H), 2.22-2.19 (m, 2H), 2.01-1.94 (m, 1H), 1.88-1.79 (m, 1H), 1.45-1.41 (m, 3H), 1.40 (s, 9H), 1.29-1.26 (m, 3H),

Mass (ESI): 434.5 [M⁺+1], HPLC: 92.8%

Synthesis of (2S, 3R)-3-hydroxy-2-(1-methyl-3-oxo-2, 5-diazaspiro [3.4] octan-2-yl)-N-(pyrimidin-2-ylmethyl) butanamide (2S-FNL-30)

To a stirring solution of compound (2S-FNL-29) (250 mg, 0.57 mmol) in DCM (10 mL) was added TFA (0.44 mL) under N₂ atmosphere and stirred for 2 h at RT. After consumption of the starting material (by TLC), the reaction mixture was concentrated under reduced pressure. The obtained crude material was triturated with diethylether/n-pentane (5 mL/5 mL) and dried under reduced pressure to afford (2S-FNL-30) (180 mg, 94.7%) as semi solid (TFA salt).

¹H-NMR: (400 MHz, D₂O): δ 8.82 (d, J=2.0 Hz, 2H), 7.53 (t, J=4.8 Hz, 1H), 4.67-4.62 (m, 2H), 4.44-4.40 (m, 1H), 4.34-4.32 (m, 2H), 3.61-3.56 (m, 2H), 2.51-2.20 (m, 4H), 1.55-1.46 (m, 3H), 1.32-1.29 (m, 3H)

LCMS (ESI): m/z 333.3

HPLC: 90.7%

Synthesis of (2S, 3R)-3-hydroxy-2-(5-isobutyryl-1-methyl-3-oxo-2, 5-diazaspiro [3.4] octan-2-yl)-N-(pyrimidin-2-ylmethyl) butanamide (2S-FNL-31)

To a stirring solution of compound (2S-FNL-30) (150 mg, 0.45 mmol) in DCM (5 mL) was added TEA (0.18 mL, 1.35 mmol) followed by isobutyryl chloride (57 mg, 0.54 mmol) at 0° C. under N₂ atmosphere and stirred for 2 h at RT. After consumption of the starting material (by TLC), the reaction mixture was diluted with water (5 mL) and extracted with CH₂Cl₂ (2×10 mL). The combined organic layer was dried over anhydrous Na₂SO₄, filtered and concentrated under reduced pressure. Obtained crude material was purified by silica gel column chromatography eluting 2% MeOH/DCM to afford (2S-FNL-31) (85 mg, 47%) as semi solid.

¹H-NMR: (400 MHz, CD₃OD): δ 8.73 (d, J=4.8 Hz, 2H), 7.36 (t, J=4.8 Hz, 1H), 4.83-4.54 (m, 3H), 4.35-4.32 (m, 1H), 4.22-4.11 (m, 1H), 3.93-3.88 (m, 1H), 3.76-3.71 (m, 1H), 3.67-3.60 (m, 2H), 2.81-2.76 (m, 1H), 2.21-2.07 (m, 3H), 1.96-1.91 (m, 1H), 1.29-1.26 (m, 6H), 1.05-1.02 (m, 6H)

LCMS (ESI): m/z 404.4

HPLC: 93.57%

Scheme 2S-16:

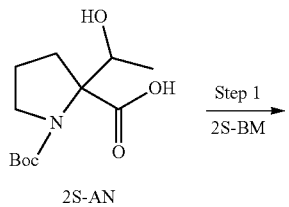

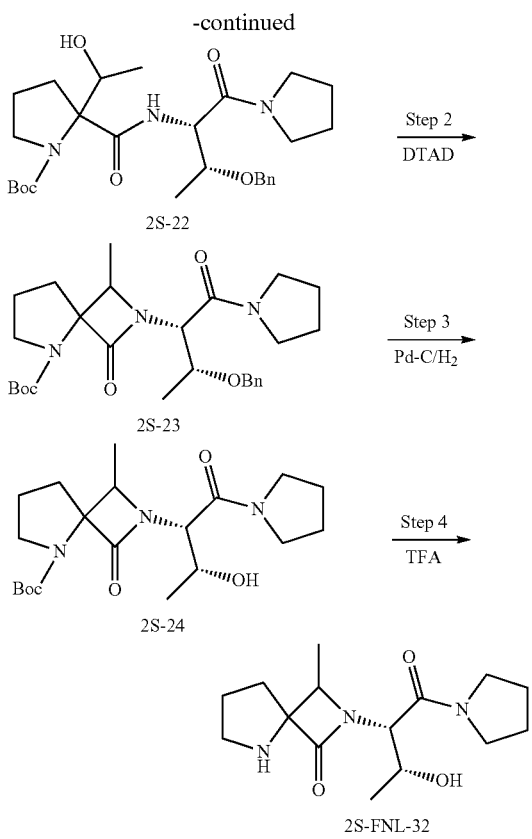

Synthesis of tert-butyl 2-(((2S, 3R)-3-(benzyloxy)-1-oxo-1-(pyrrolidin-1-yl) butan-2-yl) carbamoyl)-2-(1-hydroxyethyl) pyrrolidine-1-carboxylate (2S-22)

To a stirring solution of compound 2S-AN (2.5 g, 9.65 mmol) in CH$_2$Cl$_2$ (50 mL) were added compound 2S-BM (2.7 g, 10.6 mmol), EDCI.HCl (2.7 g, 14.4 mmol) followed by HOBt (1.9 g, 14.4 mmol) and DIPEA (5.3 mL, 28.9 mmol) at 0° C. and stirred for 12 h. After consumption of the starting material (by TLC), the reaction mixture was diluted with water (30 mL) and extracted with CH$_2$Cl$_2$ (2×50 mL). The separated organic layer was washed with brine, dried over anhydrous Na$_2$SO$_4$, filtered and concentrated under reduced pressure. Obtained crude material was purified by silica gel column chromatography eluting 2% MeOH/DCM to afford compound 2S-22 (3.5 g, 73%) as colorless liquid.

$^1$H-NMR: (500 MHz, DMSO-d$_6$): δ 8.11 (d, J=9.0 Hz, 1H), 7.82 (d, J=8.5 Hz, 1H), 7.33-7.26 (m, 5H), 6.56 (s, 1H), 4.68-4.63 (m, 1H), 4.56 (s, 2H), 3.80-3.74 (m, 1H), 3.55-3.33 (m, 5H), 1.76-1.66 (m, 7H), 1.40 (s, 9H), 1.37-1.24 (m, 2H), 1.08-0.97 (m, 6H).

Mass (ESI): m/z 504 [M$^+$+1].

Synthesis of tert-butyl 2-((2S, 3R)-3-(benzyloxy)-1-oxo-1-(pyrrolidin-1-yl) butan-2-yl)-1-methyl-3-oxo-2, 5-diazaspiro [3.4] octane-5-carboxylate (2S-23)

To a stirring solution of compound 2S-22 (3.5 g, 6.95 mmol) in THF (50 mL) was added triphenylphosphine (3.6 g, 13.9 mmol) and DTAD (3.2 g, 13.9 mmol). The reaction mixture was stirred at RT for 16 h. After consumption of the starting material (by TLC), the reaction was concentrated under reduced pressure. The crude material was purified by silica gel column chromatography eluting 30% EtOAc/hexane to afford compound 2S-23 (1.0 g, 30%) as pale yellow liquid.

$^1$H-NMR: (500 MHz, DMSO-d$_6$): δ 7.63-7.54 (m, 1H), 7.41-7.24 (m, 4H), 4.60-4.37 (m, 3H), 3.98 (d, J=10.0 Hz, 1H), 3.91 (d, J=7.0 Hz, 1H), 3.77 (d, J=7.0 Hz, 2H), 3.44-3.34 (m, 4H), 2.01-1.91 (m, 2H), 1.85-1.68 (m, 6H), 1.40 (s, 9H), 1.20-1.11 (m, 6H).

Mass (ESI): m/z 486.6 [M$^+$+1].

Synthesis of (2S, 3R)-2-(5-(tert-butoxycarbonyl)-1-oxo-2, 5-diazaspiro [3.4] octan-2-yl)-3-hydroxybutanoic acid (2S-24)

To a stirring solution of compound 2S-23 (1 g) in methanol (30 mL) was added 10% Pd/C (400 mg) at RT and stirred for 12 h under H$_2$ atmosphere (balloon pressure). After consumption of the starting material (by TLC), the reaction mixture was filtered through a pad of celite and the pad was washed with methanol. Obtained filtrate was concentrated under reduced pressure to afford compound 2S-24 (230 mg, 28%) as white solid.

$^1$H-NMR: (500 MHz, DMSO-d$_6$): δ 4.79 (br s, 1H), 4.34 (br s, 1H), 4.27 (d, J=8.5 Hz, 1H), 4.03-3.95 (m, 1H), 3.78 (d, J=6.5 Hz, 1H), 3.67-3.63 (m, 1H), 3.53-3.49 (m, 2H), 3.39 (t, J=9.0 Hz, 2H), 2.04-1.67 (m, 8H), 1.36 (s, 9H), 1.26 (d, J=6.0 Hz, 3H), 1.08, 1.06 (dd, J=6.5 Hz, 3H).

LCMS: 396.4 [M$^+$+1].

Synthesis of 2-((2S, 3R)-3-hydroxy-1-oxo-1-(pyrrolidin-1-yl) butan-2-yl)-3-methyl-2, 5-diazaspiro [3.4] octan-1-one (2S-FNL-32)

To a stirring solution of compound 2S-24 (230 mg, 0.58 mmol) in CH$_2$Cl$_2$ (2 mL) was added TFA (0.44 mL, 5.82 mmol) at 0° C. and stirred at RT for 2 h. After completion of reaction (by TLC), the reaction mixture was concentrated under reduced pressure to afford (2S-FNL-32) was triturated with pentane and diethyl ether (5 mL/5 mL) (210 mg, 92%) as sticky solid (TFA salt).

$^1$H-NMR: (400 MHz, D$_2$O): δ 4.27 (d, J=8.0 Hz, 1H), 4.07-4.03 (m, 1H), 4.01-3.97 (m, 1H), 3.52-3.48 (m, 1H), 3.39-3.35 (m, 2H), 3.32-3.20 (m, 3H), 2.16 (t, J=7.6 Hz, 2H), 2.06-1.96 (m, 2H), 1.89-1.80 (m, 2H), 1.78-1.74 (m, 2H), 1.43 (d, J=6.4 Hz, 3H), 1.06 (d, J=6.0 Hz, 3H);

Scheme 2S-17:

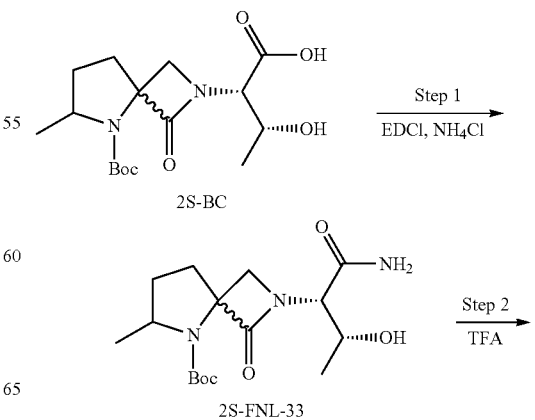

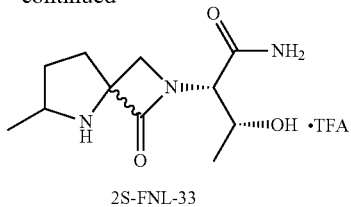

2S-FNL-33

Synthesis of tert-butyl 2-((2S, 3R)-1-amino-3-hydroxy-1-oxobutan-2-yl)-6-methyl-1-oxo-2, 5-diazaspiro [3.4] octane-5-carboxylate (2S-FNL-33)

To a stirring solution of compound 2S-BC (1.5 g, 4.38 mmol) in DCM (25 mL) were added N, N-diisopropylethylamine (2.35 mL, 13.14 mmol), NH$_4$Cl (310 mg, 8.76 mmol), followed by EDCI (1 g, 5.25 mmol), HOBT (793 mg, 5.25 mmol) at 0° C. and stirred at RT for 16 h. After consumption of the starting material (by TLC), the reaction mixture was diluted with water (20 mL). The separated organic layer was washed with citric acid solution (1×30 mL) followed by brine solution (1×30 mL). The organic layer was dried over anhydrous Na$_2$SO$_4$ and concentrated under reduced pressure to afford crude compound which was purified by column chromatography by eluting 5% MeOH/DCM to obtained compound (2S-FNL-33) (600 mg, 41%) as white solid.

$^1$H-NMR: (400 MHz, CD$_3$OD): δ 4.24-4.17 (m, 1H), 4.03-3.99 (m, 3H), 3.67-3.46 (m, 1H), 2.40-1.99 (m, 3H), 1.68-1.62 (m, 1H), 1.46 (s, 9H), 1.24-1.18 (m, 6H);

LCMS (ESI): m/z 342.5 [M$^+$+1]

Synthesis of (2S, 3R)-3-hydroxy-2-(6-methyl-1-oxo-2, 5-diazaspiro [3.4] octan-2-yl) butanamide (2S-FNL-34)

To a stirring solution of compound (2S-FNL-33) (200 mg, 0.58 mmol) in DCM (10 mL) was added trifluoroacetic acid (0.5 mL), at 0° C. under N$_2$ atmosphere. The reaction mixture was stirred at RT for 2 h. After consumption of the starting material (by TLC), the reaction mixture was concentrated under reduced pressure to afford crude, which was triturated with n-pentane (10 mL) to afford (2S-FNL-34) (100 mg, 71%) as white solid.

$^1$H-NMR: (400 MHz, D$_2$O): δ 4.35-4.27 (m, 2H), 4.08-3.93 (m, 3H), 2.58-2.52 (m, 1H), 2.48-2.44 (m, 2H), 1.92-1.86 (m, 1H), 1.51, 1.48 (dd, J=6.8 Hz, 6.4 Hz, 3H), 1.31, 1.28 (dd, J=6.0 Hz, 6.4 Hz, 3H);

LCMS (ESI): 241.3 [M$^+$+1]

Scheme 2S-18:

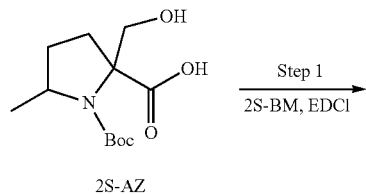

2S-AZ

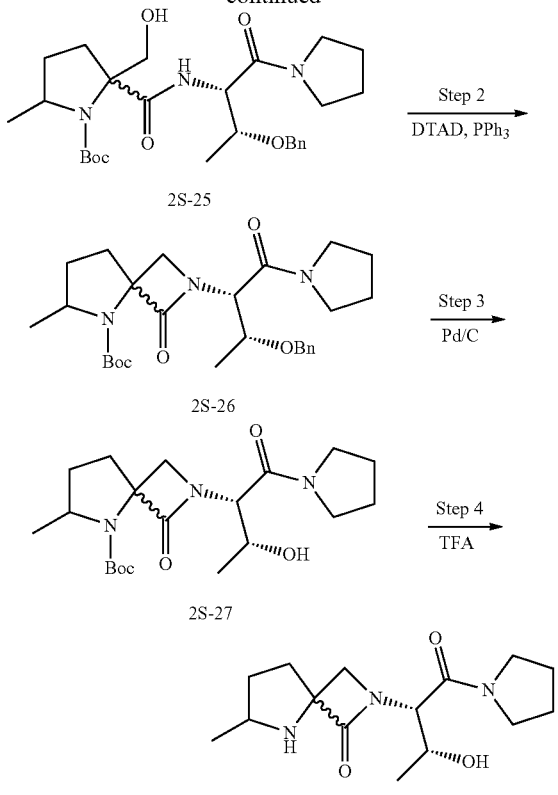

Synthesis of tert-butyl 2-(((2S, 3R)-3-(benzyloxy)-1-oxo-1-(pyrrolidin-1-yl) butan-2-yl) carbamoyl)-2-(hydroxymethyl)-5-methylpyrrolidine-1-carboxylate (2S-25)

To a stirring solution of compound 2S-AZ (1.1 g, 4.28 mmol) in DCM (20 mL) were added N, N-diisopropylethylamine (2.2 mL, 12.8 mmol), 2S-BM (1.2 g, 4.78 mmol), followed by EDCI (2.45 g, 12.8 mmol), HOBT (1.7 g, 12.8 mmol) at 0° C. and stirred at RT for 12 h. After consumption of the starting material (by TLC), the reaction mixture was diluted with water (10 mL). The separated organic layer was washed with saturated NaHCO$_3$ solution (1×25 mL), followed by brine solution (1×30 mL). The separated organic layer was dried over anhydrous Na$_2$SO$_4$ and concentrated under reduced pressure to afford crude compound which was purified by column chromatography eluting 5% MeOH/DCM to obtained compound 2S-25 (1.2 g, 57%) as a thick white syrup.

$^1$H-NMR: (400 MHz, DMSO-d$_6$): δ 7.93 (t, J=7.6 Hz, 1H), 7.71-7.26 (m, 5H), 5.30 (br s, 1H), 4.65-4.61 (m, 1H), 4.57 (s, 2H), 3.93-3.85 (m, 2H), 3.57-3.34 (m, 2H), 3.17-3.09 (m, 2H), 2.07-1.94 (m, 2H), 1.77-1.73 (m, 4H), 1.36-1.28 (m, 10H), 1.20 (s, 9H);

LCMS: m/z 504.7 [M$^+$+1].

Synthesis of tert-butyl 2-((2S, 3R)-3-(benzyloxy)-1-oxo-1-(pyrrolidin-1-yl) butan-2-yl)-6-methyl-1-oxo-2, 5-diazaspiro [3.4] octane-5-carboxylate (2S-26)

To a stirring solution of compound 2S-25 (0.6 g, 1.19 mmol) in THF (10 mL) was added triphenylphosphine (0.46 g, 1.78 mmol) and DTAD (0.4 g, 1.78 mmol). The reaction mixture was stirred at RT for 16 h. After consumption of the starting material (by TLC), the reaction mixture was diluted with water (10 mL). The separated organic layer was washed with brine solution (1×30 mL). The separated organic layer was dried over anhydrous $Na_2SO_4$ and concentrated under reduced pressure to afford crude compound which was purified by column chromatography eluting 2% MeOH/DCM to obtained compound 2S-26 (0.2 g, 35%) as white solid.

$^1$H-NMR: (500 MHz, DMSO-d6): δ 7.63-7.26 (m, 5H), 4.52 (s, 2H), 3.91-3.77 (m, 3H), 3.56-3.36 (m, 4H), 2.35-2.11 (m, 4H), 1.94-1.68 (m, 6H), 1.39 (s, 9H), 1.13, 1.09 (dd, J=6.0 Hz, 5.5 Hz, 3H), 1.04 (d, J=6.5 Hz, 3H);

LCMS: m/z 486.6 [M$^+$+1].

Synthesis of tert-butyl 2-((2S, 3R)-3-(benzyloxy)-1-oxo-1-(pyrrolidin-1-yl) butan-2-yl)-6-methyl-1-oxo-2, 5-diazaspiro [3.4] octane-5-carboxylate (2S-27)

To a stirring solution of compound 2S-26 (1.5 g, 3.09 mmol) in methanol (20 mL) was added 10% Pd/C (200 mg) under $N_2$ atmosphere. The reaction mixture was stirred under $H_2$ atmosphere (balloon pressure) at RT for 4 h. After consumption of the starting material (by TLC), the reaction mixture was filtered through a pad of celite and the pad was washed with methanol. Obtained filtrate was concentrated under reduced pressure to afford crude compound which was purified by column chromatography to obtained compound 2S-27 (0.9 g, 90.9%) as white solid.

$^1$H-NMR: (500 MHz, CDCl$_3$): δ 4.11 (d, J=7.0 Hz, 1H), 3.96-3.90 (m, 1H), 3.73 (s, 2H), 3.49 (d, J=13.0 Hz, 2H), 3.40-3.34 (m, 2H), 2.50-2.28 (m, 4H), 2.17-1.82 (m, 6H), 1.53 (s, 9H), 1.52-1.41 (m, 3H), 1.36-1.18 (m, 3H);

LCMS: 396.5 [M$^+$+1].

Synthesis of 2-((2S, 3R)-3-hydroxy-1-oxo-1-(pyrrolidin-1-yl) butan-2-yl)-6-methyl-2, 5-diazaspiro [3.4] octan-1-one (2S-FNL-35)

To a stirring solution of compound 2S-27 (0.18 g, 0.45 mmol) in methanol (10 mL) was added TFA (3 mL) under $N_2$ atmosphere at 0° C. After consumption of the starting material (by TLC), the reaction mixture was concentrated under reduced pressure to afford crude compound which was triturated with n-pentane (10 mL) to obtained (2S-FNL-35) (0.1 g, 74.6%) as white solid.

$^1$H-NMR: (400 MHz, DMSO-d$_6$): δ 9.99 (br s, 1H), 9.57 (br s, 1H), 4.32 (d, J=7.6 Hz, 1H), 3.93 (t, J=6.0 Hz, 1H), 3.81-3.75 (m, 3H), 3.51-3.46 (m, 2H), 3.30 (t, J=6.8 Hz, 2H), 2.29-2.20 (m, 3H), 1.93-1.75 (m, 4H), 1.68-1.63 (m, 1H), 1.34 (d, J=6.8 Hz, 3H), 1.13 (d, J=6.4 Hz, 3H);

Mass (ESI): m/z 296.3 [M$^+$+1]

Scheme 2S-19:

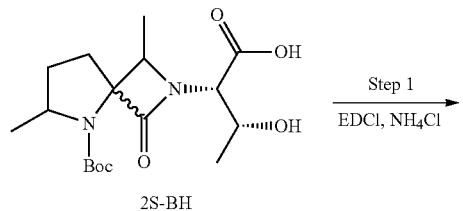

2S-BH

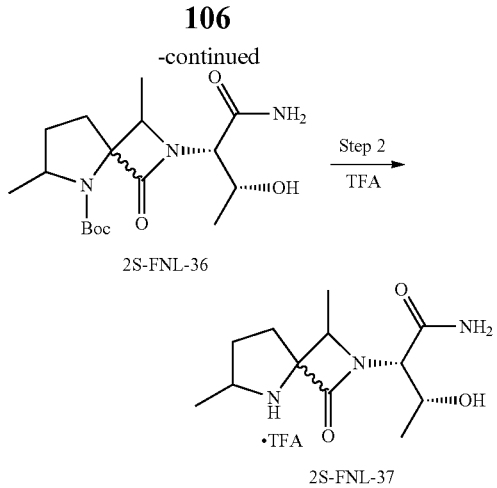

Synthesis of tert-butyl 2-((2S,3R)-1-amino-3-hydroxy-1-oxobutan-2-yl)-1,6-dimethyl-3-oxo-2,5-diazaspiro[3.4]octane-5-carboxylate (2S-FNL-36)

To a stirring solution of compound 2S-BH (1.8 g, 5.05 mmol) in $CH_2Cl_2$ (50 mL) were added DIPEA (2.62 mL, 15.15 mmol), EDCI (1.92 g, 10.1 mmol), HOBt (1.36 g, 10.1 mmol) followed by $NH_4Cl$ (803 mg, 15.15 mmol) at 0° C. and stirred for 12 h at RT. After consumption of the starting material (by TLC), the reaction mixture was diluted with water (30 mL). The separated organic layer was washed with citric acid solution (1×50 mL) followed by brine solution (1×50 mL). The organic layer was dried over anhydrous $Na_2SO_4$ and concentrated under reduced pressure to afford crude compound which was purified by column chromatography by eluting 4% MeOH/DCM to afford (2S-FNL-36) (468 mg, 26%) as white solid.

$^1$H-NMR: (400 MHz, DMSO-d$_6$): δ7.25 (s, 2H), 4.92-4.48 (m, 1H), 4.34-4.01 (m, 1H), 3.97-3.72 (m, 3H), 2.32-1.88 (m, 3H), 1.58-1.51 (m, 1H), 1.41 (s, 9H), 1.36-1.20 (m, 6H), 1.16-1.07 (m, 3H);

LCMS (ESI): 356.4 [M$^+$+1];

HPLC: 99.19%

Synthesis of (2S,3R)-2-(1,6-dimethyl-3-oxo-2,5-diazaspiro[3.4]octan-2-yl)-3-hydroxy butanamide (2S-FNL-37)

To a stilling solution of (2S-FNL-36) (200 mg, 0.56 mmol) in DCM (5 mL) was added TFA (0.45 mL, 5.63 mmol) at 0° C. and stirred at RT for 2 h. After consumption of the starting material (by TLC), the reaction mixture was concentrated under reduced pressure. The crude material was triturated with diethyl ether/n-pentane (50 mL/50 mL) and dried under reduced pressure to afford (2S-FNL-37) (140 mg, 98%) as hygroscopic white solid (TFA salt).

$^1$H-NMR: (400 MHz, D$_2$O): δ4.42-4.36 (m, 1H), 4.34-4.28 (m, 1H), 4.27-4.15 (m, 1H), 4.07-4.01 (m, 1H), 2.57-2.49 (m, 1H), 2.46-2.36 (m, 2H), 2.01-1.90 (m, 1H), 1.56-1.50 (m, 6H), 1.32-1.29 (m, 3H);

LCMS (ESI): 256.4 [M$^+$+1];

HPLC (ELSD): 93.86%.

Scheme 2S-20:

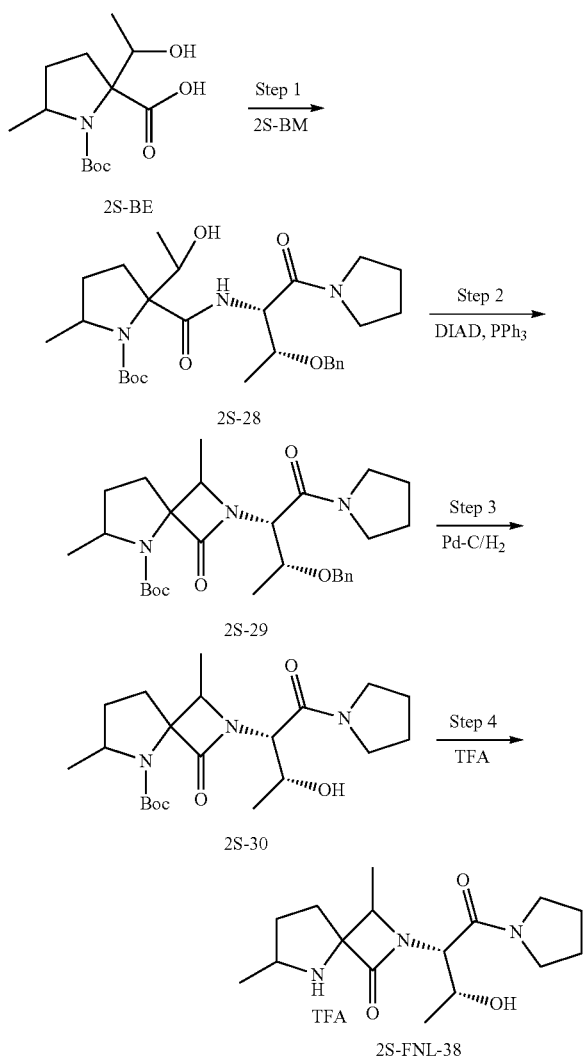

Synthesis of tert-butyl2-(((2S,3R)-3-(benzyloxy)-1-oxo-1-(pyrrolidin-1-yl)butan-2-yl) carbamoyl)-2-(1-hydroxyethyl)-5-methylpyrrolidine-1-carboxylate (2S-28)

To a stirring solution of compound 2S-BE (2 g, 7.32 mmol) in DMF (20 mL) were added N,N-diisopropylethylamine (6.7 mL, 36.5 mmol), 2S-BM (2.6 g, 8.7 mmol), followed by HATU (3.3 g, 8.7 mmol) at 0° C. and stirred at RT for 16 h. After consumption of the starting material (by TLC), the reaction mixture was diluted with water (100 mL) and EtOAc (200 mL). The separated organic layer was washed with sodium bicarbonate solution (2×75 mL), citric acid solution (2×50 mL) followed by brine solution (1×50 mL). The separated organic layer was dried over anhydrous $Na_2SO_4$ and concentrated under reduced pressure to afford crude compound which was purified by column chromatography by eluting 40% EtOAc/n-hexane to obtain compound 25-28 (1 g, 27%) as pale yellow liquid;

LCMS (ESI): 518 [M$^+$+1]

Synthesis of tert-butyl 2-((2S,3R)-3-(benzyloxy)-1-oxo-1-(pyrrolidin-1-yl)butan-2-yl)-1,6-dimethyl-3-oxo-2,5-diazaspiro [3.4] octane-5-carboxylate (2S-29)

To a stirring solution of triphenylphosphine (1.5 g, 5.7 mmol) in THF (10 mL) was added DIAD (976 mg, 4.8 mmol) as portion-wise and stirred for 20 min at RT. To this was added compound 2S-28 (1 g, 1.93 mmol) in THF (10 mL) slowly at RT and stirred for 4 h. After consumption of the starting material (by LCMS), the reaction mixture was concentrated under reduced pressure. The crude material was purified by silica gel column chromatography eluting 30% EtOAc/hexane to afford compound 2S-29 (500 mg, 63%) as yellow liquid.

$^1$H-NMR: (400 MHz, CDCl3): δ7.69-7.66 (m, 1H), 7.48-7.43 (m, 1H), 7.32-7.29 (m, 3H), 4.68 (s, 2H), 4.46-4.40 (m, 1H), 4.26-4.05 (m, 2H), 3.97-3.91 (m, 0.5H), 3.87-3.81 (m, 0.5H), 3.58-3.53 (m, 1H), 3.40-3.32 (m, 2H), 2.16-2.11 (m, 1H), 2.04-1.90 (m, 2H), 1.80-1.71 (m, 2H), 1.41 (s, 9H), 1.32-1.21 (m, 10H), 1.17-1.15 (m, 3H).

LCMS (ESI): 500 [M$^+$+1].

Synthesis of tert-butyl2-((2S 3 R)-3-hydroxy-1-oxo-1-(pyrrolidin-1-yl) butan-2-yl)-1, 6-dimethyl-3-oxo-2, 5-diazaspiro [3.4] octane-5-carboxylate (2S-30)

To a stirring solution of compound 2S-29 (200 mg, 0.40 mmol) in methanol (5 mL) was added 10% Pd/C (50 mg) under $N_2$ atmosphere. The reaction mixture was stirred under $H_2$ atmosphere at RT for 4 h. After consumption of the starting material (by TLC), the reaction mixture was filtered through a pad of celite and the pad was washed with methanol (10 mL). Obtained filtrate was concentrated under reduced pressure to obtained crude compound, which was purified by column chromatography eluting 1% MeOH/DCM to afford compound 2S-30 (100 g, 61%) as yellow syrup.

$^1$H-NMR: (400 MHz, DMSO-d$_6$): δ 4.93 (d, J=5.6 Hz, 1H), 4.26 (d, J=9.2 Hz, 0.5H), 4.17 (d, J=7.2 Hz, 0.5H), 4.02-3.99 (m, 1H), 3.91-3.66 (m, 3H), 3.33-3.30 (m, 1H), 3.55-3.50 (m, 1H), 3.19-3.16 (m, 1H), 2.69 (s, 1H), 2.13-2.03 (m, 1H), 1.99-1.87 (m, 3H), 1.81-1.75 (m, 2H), 1.56-1.50 (m, 1H), 1.39 (s, 9H), 1.19 (d, J=5.6 Hz, 3H), 1.13 (d, J=6.4 Hz, 6H).

LCMS: 410.5 [M$^+$+1].

Synthesis of 2-((2S,3R)-3-hydroxy-1-oxo-1-(pyrrolidin-1-yl)butan-2-yl)-3,6-dimethyl-2,5-diazaspiro [3.4]octan-1-one (2S-FNL-38)

To a stirring solution of compound 2S-30 (300 mg, 0.73 mmol) in DCM (20 mL) was added TFA (418 mg, 3.66 mmol) at 0° C. under $N_2$ atmosphere. The reaction mixture was stirred at RT for 4 h. After consumption of the starting material (by TLC), the reaction mixture was evaporated under reduced pressure to afford crude, which was purified by preparative HPLC method to afford (2S-FNL-38) (140 mg, 46%) as thick syrup.

$^1$H-NMR: (400 MHz, D$_2$O): δ4.53-4.46 (m, 1H), 4.34-4.22 (m, 2H), 4.03 (d, J=6.4 Hz, 1H), 3.68 (s, 2H), 3.52-3.41 (m, 2H), 2.44-2.37 (m, 3H), 2.03-1.94 (m, 5H), 1.56 (d, J=6.4 Hz, 6H), 1.27 (d, J=6.0 Hz, 3H).

LCMS (ESI): 310 [M$^+$+1].

Scheme 2S-I-15:

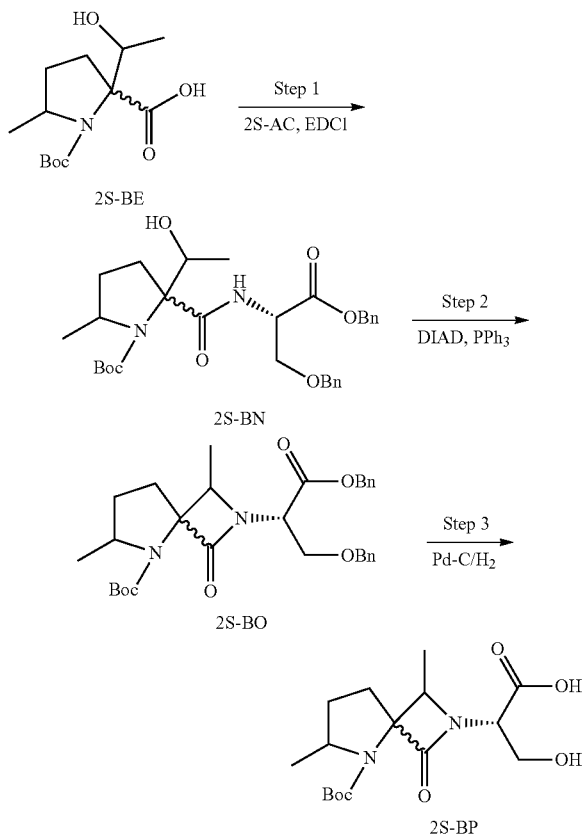

Synthesis of tert-butyl 2-(((S)-1, 3-bis (benzyloxy)-1-oxopropan-2-yl) carbamoyl)-2-(1-hydroxyethyl)-5-methylpyrrolidine-1-carboxylate (2S-BN)

To a stirring solution of 2S-BE (3 g, 10.98 mmol) in DCM (30 mL) were added N, N-diisopropylethylamine (5.73 mL, 32.96 mmol), 2S-AC (3.75 g, 13.17 mmol) followed by HATU (5 g, 13.17 mmol) at 0° C. and stirred at RT for 16 h. After consumption of the starting material (by TLC), the reaction mixture was diluted with water (20 mL). The separated organic layer was washed with brine solution (30 mL). The organic layer was dried over anhydrous $Na_2SO_4$ and concentrated under reduced pressure to afford crude compound which was purified by column chromatography by eluting 20% EtOAc/n-hexane to obtained compound 2S-BN (2.9 g, 49%) as brown thick syrup.
$^1$H-NMR: (500 MHz, DMSO-$d_6$): δ 8.50 (m, 1H), 7.33-7.27 (m, 10H), 5.68-5.60 (m, 1H), 5.22-5.09 (m, 2H), 4.72-4.43 (m, 3H), 3.89-3.63 (m, 3H), 2.28-1.78 (m, 3H), 1.45-1.42 (m, 1H), 1.36 (s, 9H), 1.26-1.04 (m, 6H);
LCMS (ESI): m/z 541.6 [M$^+$+1]

Synthesis of tert-butyl 2-((S)-1,3-bis(benzyloxy)-1-oxopropan-2-yl)-1,6-dimethyl-3-oxo-2,5-diazaspiro [3.4]octane-5-carboxylate (2S-BO)

To a stirring solution of triphenylphosphine (3.51 g, 13.42 mmol) in dry THF (30 mL) was added DIAD (2.21 g, 10.74 mmol) as portionwise and stirred for 15 min at RT. To this precipitated solution added 2S-BN (2.9 g, 5.37 mmol) in dry THF (15 mL) slowly at RT and stirred for 16 h. After consumption of the starting material (by TLC), the reaction mixture was concentrated under reduced pressure. The crude material was triturated with 30% di ehylether/n-pentane. The filtrate was concentrated under reduced pressure to obtained crude compound which was purified by silica gel column chromatography eluting 30% EtOAc/hexane to afford 2S-BO (2.5 g, 89.2%) as brown thick syrup.
$^1$H-NMR: (500 MHz, DMSO-$d_6$): δ 7.38-7.25 (m, 10H), 5.22-5.15 (m, 2H), 4.80-4.73 (m, 2H), 4.56-4.43 (m, 2H), 3.92-3.60 (m, 3H), 1.89-1.83 (m, 3H), 1.50-1.44 (m, 1H), 1.40 (s, 9H), 1.22-1.18 (s, 3H), 1.16-1.13 (m, 3H);
LCMS (ESI): m/z 523.6 [M$^+$+1]

Synthesis of (2S)-2-(5-(tert-butoxycarbonyl)-1,6-dimethyl-3-oxo-2, 5-diazaspiro [3.4] octan-2-yl)-3-hydroxypropanoic acid (2S-BP)

To a stirring solution of 2S-BO (2.5 g, 4.78 mmol) in methanol (50 mL) was added 10% Pd/C (800 mg) under $N_2$ atmosphere. The reaction mixture was stirred under $H_2$ atmosphere at RT for 16 h. After consumption of the starting material (by TLC), the reaction mixture was filtered through a pad of celite and the pad was washed with methanol (30 mL). Obtained filtrate was concentrated under reduced pressure to afford crude which was triturated with n-pentane (30 mL) to afford 2S-BP (900 mg, 56.2%) as sticky solid.
$^1$H-NMR: (400 MHz, DMSO-$d_6$): δ 4.78-4.75 (m, 1H), 4.24-4.18 (m, 1H), 3.86-3.81 (m, 1H), 3.80-3.72 (m, 2H), 3.64-3.59 (m, 1H), 2.15-1.93 (m, 3H), 1.55-1.50 (m, 1H), 1.39 (s, 9H), 1.24-1.10 (m, 6H);
LCMS (ESI): m/z 343.3 [M$^+$+1]

Scheme 2S-21:

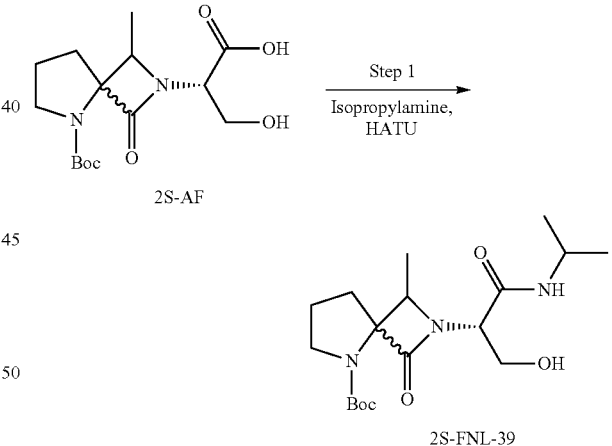

Synthesis of tert-butyl 2-((S)-3-hydroxy-1-(isopropylamino)-1-oxopropan-2-yl)-1-oxo-2, 5-diazaspiro [3.4] octane-5-carboxylate (2S-FNL-39)

To a stirring solution of 2S-AF (200 mg, 0.63 mmol) in $CH_2Cl_2$ (10 mL) were added DIPEA (0.32 mL, 1.90 mmol), isopropyl amine (0.08 mL, 0.94 mmol), HATU (287 mg, 0.75 mmol) at 0° C. and stirred to RT for 5 h. After consumption of the starting material (by TLC), the reaction mixture was diluted with water (10 mL). The separated organic layer was washed with citric acid (1×20 mL) followed by brine solution (1×20 mL). The organic layer was dried over anhydrous Na₂SO₄, filtered and concentrated under reduced pressure. Obtained crude material was purified by preparative HPLC purification to afford (2S-FNL-39) (150 mg, 67.2%) as white solid.

¹H-NMR: (400 MHz, DMSO-d₆): δ 7.76 (d, J=8.4 Hz, 1H), 5.01-4.91 (m, 1H), 4.70 (t, J=6.0 Hz, 1H), 4.14-4.07 (m, 1H), 3.99-3.80 (m, 2H), 3.78-3.61 (m, 2H), 3.58-3.35 (m, 2H), 2.20-2.05 (m, 2H), 1.85-1.77 (m, 2H), 1.43 (s, 9H), 1.10-1.00 (m, 6H)

Mass (ESI): m/z 356.6 [M⁺+1]
HPLC: 99.27%

Scheme 2S-22:

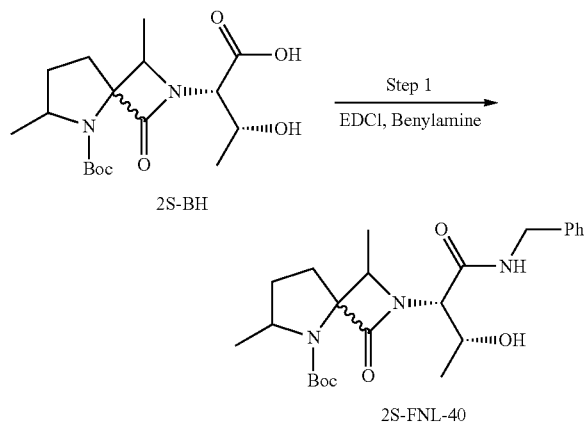

Synthesis of tert-butyl 2-((2S,3R)-1-(benzylamino)-3-hydroxy-1-oxobutan-2-yl)-1,6-dimethyl-3-oxo-2,5-diazaspiro[3.4]octane-5-carboxylate (2S-FNL-40)

To a stirring solution of 2S-BH (250 mg, 0.70 mmol) in CH₂Cl₂ (10 mL) were added DIPEA (0.36 mL, 2.11 mmol), EDCI (161 mg, 0.84 mmol), HOBt (129 mg, 0.84 mmol) followed by benzylamine (82 mg, 0.77 mmol) at 0° C. and stirred for 12 h at RT. After consumption of the starting material (by TLC), the reaction mixture was diluted with water (10 mL). The separated organic layer was dried over anhydrous Na₂SO₄ and concentrated under reduced pressure to afford crude compound which was purified by column chromatography by eluting 5% MeOH/DCM to afford (2S-FNL-40) (55 mg, 16%) as an off-white solid.

¹H-NMR: (400 MHz, DMSO-d₆): δ 7.31-7.20 (m, 5H), 4.92-4.87 (m, 1H), 4.64-4.55 (m, 1H), 4.46-4.37 (m, 2H), 4.22-4.10 (m, 1H), 4.02-3.90 (m, 2H), 2.39-1.95 (m, 3H), 1.70-1.60 (m, 1H), 1.37 (s, 9H), 1.30-1.22 (m, 9H);

LCMS (ESI): m/z 446.56 [M⁺+1];
HPLC: 89.54%

Scheme 2S-23:

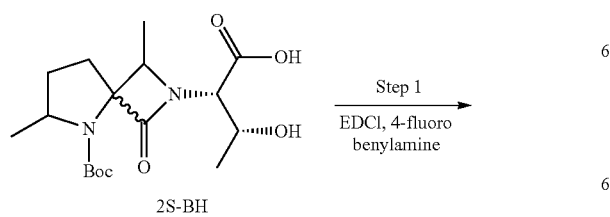

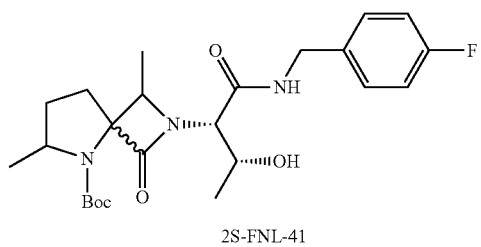

Synthesis of tert-butyl 2-((2S,3R)-1-((4-fluorobenzyl)amino)-3-hydroxy-1-oxobutan-2-yl)-1,6-dimethyl-3-oxo-2,5-diazaspiro[3.4]octane-5-carboxylate (2S-FNL-41)

To a stirring solution of 2S-BH (500 mg, 1.40 mmol) in CH₂Cl₂ (10 mL) were added DIPEA (0.73 mL, 4.21 mmol), EDCI (321 mg, 1.68 mmol), HOBt (257 mg, 1.68 mmol) followed by 4-fluoro benzylamine (175 mg, 1.40 mmol) at 0° C. and stirred for 12 h at RT. After consumption of the starting material (by TLC), the reaction mixture was diluted with water (15 mL). The separated organic layer was washed with citric acid solution (1×25 mL) followed by brine solution (1×25 mL). The organic layer was dried over anhydrous Na₂SO₄ and concentrated under reduced pressure to afford crude compound which was purified by column chromatography by eluting 5% MeOH/DCM followed by preparative HPLC purification to afford (2S-FNL-41) (150 mg, 23.07%) as white solid.

¹H-NMR: (400 MHz, CD₃OD): δ 7.34-7.30 (m, 2H), 7.02-6.98 (m, 2H), 4.65-4.59 (m, 1H), 4.55-4.36 (m, 2H), 4.34-4.20 (m, 1H), 4.12-3.99 (m, 2H), 2.39-2.31 (m, 1H), 2.19-2.01 (m, 2H), 1.71-1.62 (m, 1H), 1.40 (s, 9H), 1.29-1.13 (m, 9H);

LCMS (ESI): m/z 464.5 [M⁺+1];
HPLC: 96.32%

Scheme 2S-24:

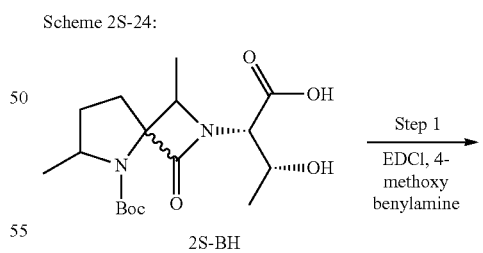

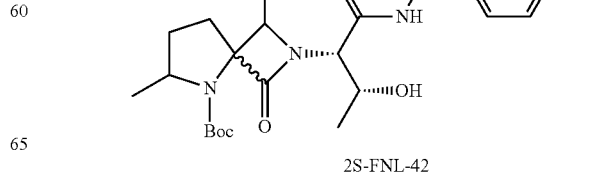

Synthesis of tert-butyl 2-((2S, 3R)-3-hydroxy-1-((4-methoxybenzyl)amino)-1-oxobutan-2-yl-1, 6-dimethyl-3-oxo-2, 5-diazaspiro [3.4] octane-5-carboxylate (2S-FNL-42)

To a stirring solution of 2S-BH (250 mg, 0.70 mmol) in CH$_2$Cl$_2$ (10 mL) were added DIPEA (0.36 mL, 2.11 mmol), EDCI (161 mg, 0.84 mmol), HOBt (129 mg, 0.84 mmol) followed by 4-methoxy benzylamine (106 mg, 0.77 mmol) at 0° C. and stirred for 12 h at RT. After consumption of the starting material (by TLC), the reaction mixture was diluted with water (10 mL). The separated organic layer was washed with citric acid solution (1×20 mL) followed by brine solution (1×25 mL). The organic layer was dried over anhydrous Na$_2$SO$_4$ and concentrated under reduced pressure to afford crude compound which was purified by column chromatography by eluting 5% MeOH/DCM to afford (2S-FNL-42) (60 mg, 17.9%) as an off-white solid.

$^1$H-NMR: (400 MHz, CD$_3$OD): δ 7.24 (d, J=1.6 Hz, 2H), 6.85 (d, J=1.6 Hz, 2H), 4.64-4.58 (m, 1H), 4.39-4.28 (m, 1H), 4.21-4.08 (m, 2H), 4.06-3.99 (m, 1H), 3.98-3.88 (m, 1H), 3.83 (s, 3H), 2.39-2.28 (m, 1H), 2.22-2.13 (m, 1H), 2.09-1.97 (m, 1H), 1.71-1.61 (m, 1H), 1.40 (s, 9H), 1.31-1.22 (m, 9H);

LCMS (ESI): m/z 476.6 [M$^+$+1];
HPLC: 90.29%

Scheme 2S-25:

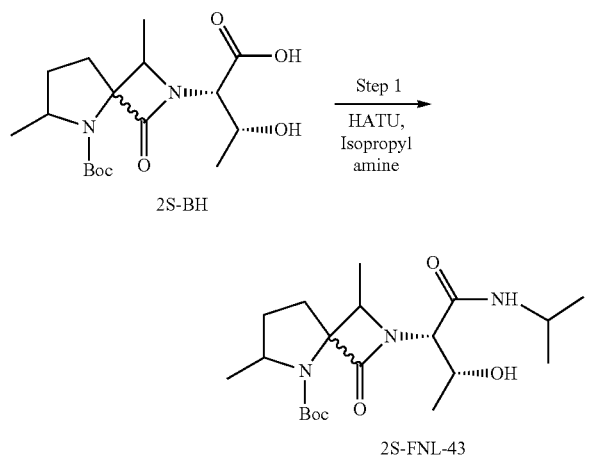

2S-BH

2S-FNL-43

Synthesis of tert-butyl 2-((2S,3R)-3-hydroxy-1-(isopropylamino)-1-oxobutan-2-yl)-1,6-dimethyl-3-oxo-2,5-diazaspiro[3.4]octane-5-carboxylate (2S-FNL-43)

To a stirring solution of 2S-BH (500 mg, 1.40 mmol) in CH$_2$Cl$_2$ (10 mL) were added DIPEA (0.73 mL, 4.21 mmol), isopropyl amine (100 mg, 1.68 mmol), HATU (798 mg, 2.1 mmol) at 0° C. and stirred for 12 h at RT. After consumption of the starting material (by TLC), the reaction mixture was diluted with water (10 mL). The separated organic layer was washed with citric acid solution (15 mL) followed by brine solution (15 mL). The organic layer was dried over anhydrous Na$_2$SO$_4$ and concentrated under reduced pressure to afford crude compound which was purified by column chromatography by eluting 2% MeOH/DCM followed by preparative HPLC purification to afford (2S-FNL-43) (100 mg, 18%) as white solid.

$^1$H-NMR: (400 MHz, D$_2$O): δ 4.42-3.89 (m, 5H), 2.38-2.04 (m, 3H), 1.77-1.72 (m, 1H), 1.40 (s, 9H), 1.36-1.17 (m, 15H)

LCMS (ESI): m/z 398.5 [M$^+$+1];
HPLC: 93.36%

Scheme 2S-26:

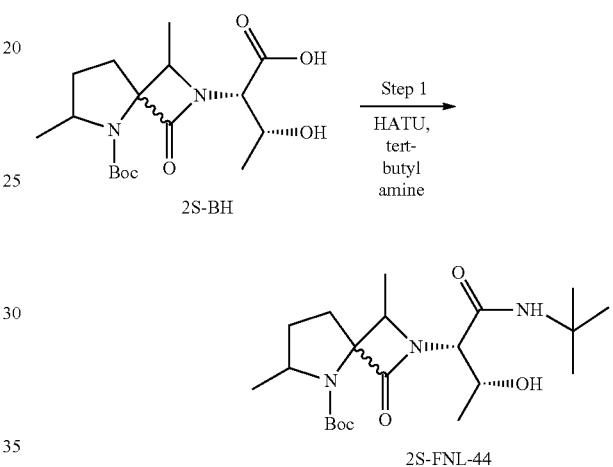

2S-BH

2S-FNL-44

Synthesis of tert-butyl 2-((2S,3R)-1-(tert-butylamino)-3-hydroxy-1-oxobutan-2-yl)-1,6-dimethyl-3-oxo-2,5-diazaspiro[3.4]octane-5-carboxylate (2S-FNL-44)

To a stirring solution of 2S-BH (500 mg, 1.40 mmol) in CH$_2$Cl$_2$ (10 mL) were added DIPEA (0.62 mL, 3.51 mmol), tert-butyl amine (125 mg, 1.68 mmol), HATU (798 mg, 2.1 mmol) at 0° C. and stirred for 12 h at RT. After consumption of the starting material (by TLC), the reaction mixture was diluted with water (10 mL). The separated organic layer was washed with citric acid solution (15 mL) followed by brine solution (15 mL). The organic layer was dried over anhydrous Na$_2$SO$_4$ and concentrated under reduced pressure to afford crude compound which was purified by column chromatography by eluting 2% MeOH/DCM followed by preparative HPLC purification to afford (2S-FNL-44) (100 mg, 17.3%) as white solid.

$^1$H-NMR: (500 MHz, CD$_3$OD): δ 4.53-4.50 (m, 1H), 4.08-3.99 (m, 2H), 3.82-3.79 (m, 1H), 2.38-2.34 (m, 1H), 2.20-2.17 (m, 2H), 2.09-2.01 (m, 1H), 1.71-1.67 (m, 1H), 1.40 (s, 9H), 1.38 (s, 9H), 1.33-1.21 (n, 9H);

LCMS (ESI): m/z 412.5 [M$^+$+1];
HPLC: 93.91%

Scheme 2S-27:

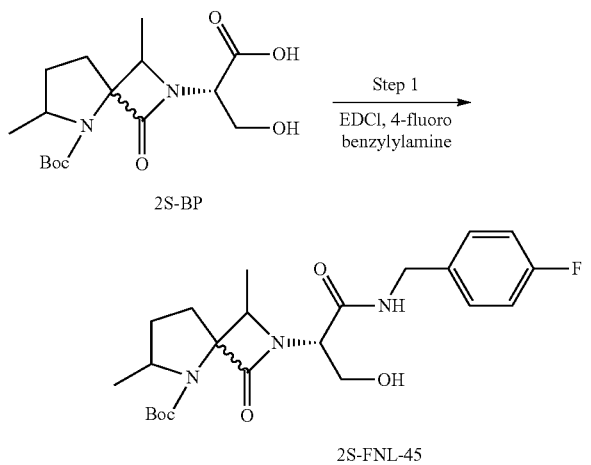

2S-BP

Step 1
EDCl, 4-fluoro
benzylylamine

2S-FNL-45

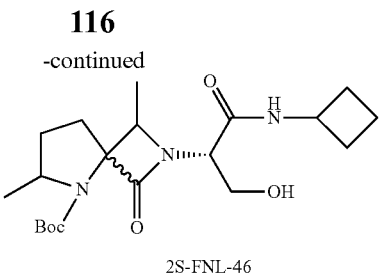

2S-FNL-46

Synthesis of tert-butyl 2-((S)-1-((4-fluorobenzyl)amino)-3-hydroxy-1-oxopropan-2-yl)-1, 6-dimethyl-3-oxo-2, 5-diazaspiro [3.4] octane-5-carboxylate (2S-FNL-45)

To a stirring solution of 2S-BP (200 mg, 0.58 mmol) in DCM (10 mL) were added N, N-diisopropylethylamine (0.3 mL, 1.75 mmol), EDCI (133 mg, 0.69 mmol), HOBT (93 mg, 0.69 mmol) followed by 4-fluoro benzylamine (79.7 mg, 0.63 mmol) at 0° C. and stirred at RT for 16 h, After consumption of the starting material (by TLC), the reaction mixture was diluted with water (20 mL). The separated organic layer was washed with citric acid (20 mL) followed by brine solution (30 mL). The separated organic layer was dried over anhydrous $Na_2SO_4$ and concentrated under reduced pressure to afford crude compound which was purified by column chromatography by eluting 3% MeOH/DCM to obtained (2S-FNL-45) (46 mg, 17.7%) as thick syrup.

$^1$H-NMR: (500 MHz, DMSO-$d_6$): δ 8.63-8.59 (m, 1H), 7.30-7.26 (m, 2H), 7.15-7.07 (m, 2H), 5.07-5.00 (m, 1H), 4.31-4.21 (m, 3H), 3.89-3.62 (m, 4H), 2.13-1.84 (m, 3H), 1.58-1.52 (m, 1H), 1.36 (s, 9H), 1.32-1.20 (m, 3H), 1.18-1.13 (m, 3H);

LCMS (ESI): m/z 450.5 [M$^+$+1]

HPLC: 93%

Scheme 2S-28:

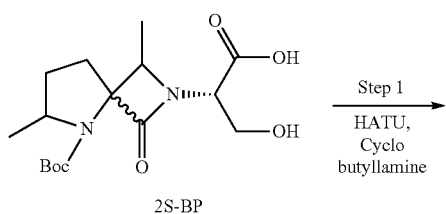

2S-BP

Step 1
HATU,
Cyclo
butyllamine

Synthesis of tert-butyl 2-((S)-1-((4-fluorobenzyl)amino)-3-hydroxy-1-oxopropan-2-yl)-1, 6-dimethyl-3-oxo-2, 5-diazaspiro [3.4] octane-5-carboxylate (2S-FNL-46)

To a stirring solution of 2S-BP (500 mg, 1.46 mmol) in DCM (15 mL) were added N, N-diisopropylethylamine (0.76 mL, 4.38 mmol), cyclobutylamine (124 mg, 1.75 mmol) followed by HATU (665 mg, 1.75 mmol) at 0° C. and stirred at RT for 16 h. After consumption of the starting material (by TLC), the reaction mixture was diluted with water (20 mL). The separated organic layer was washed with citric acid (20 mL) followed by brine solution (30 mL). The organic layer was dried over anhydrous $Na_2SO_4$, filtered and concentrated under reduced pressure to afford crude compound which was purified by column chromatography by eluting 3% MeOH/DCM to obtained (2S-FNL-46) (110 mg, 19%) as an off-white solid.

$^1$H-NMR: (400 MHz, DMSO-$d_6$): δ 8.23 (d, J=8.0 Hz, 1H), 4.98-4.83 (m, 1H), 4.30-4.13 (m, 2H), 3.95-3.76 (m, 2H), 3.72-3.66 (m, 2H), 2.49-1.89 (m, 3H), 1.64-1.54 (m, 3H), 1.48 (s, 9H), 1.19-1.12 (m, 10H);

LCMS (ESI): m/z 396.5 [M$^+$+1]

HPLC: 96.6%

Example 3

[$^3$H] MK-801 Binding Assay

Methods

Assays were conducted as described in Moskal et al. (Moskal, J. R., Kuo, A. G., Weiss, C., Wood, P. L., O'Connor Hanson, A., Kelso, S., Harris, R. B., Disterhoft, J. F., 2005. GLYX-13: a monoclonal antibody-derived peptide that acts as an N-methyl-D-aspartate receptor modulator. Neuropharmacology. 49, 1077-87) The potentiation of [$^3$H]MK-801 binding (5 nM; 22.5 Ci/mmol) to well washed rat cortical membranes (200 μg) was measured under non-equilibrium conditions (15 min @ 25° C.) in the presence of increasing concentrations of test compounds and 50 μM glutamate. Zero levels were determined in the absence of any glycine ligand and in the presence of 30 μM 5,7 DCKA. Maximal stimulation was measured in the presence of 1 mM glycine, and 50 μM glutamate was present in all samples. The facilitation of [$^3$H]MK-801 binding by tests compounds was calculated by using a 3 parameter log agonist vs. response equation (Graph pad Prism, USA) and potency (EC$_{50}$, expressed in pM) and maximal activity (% maximal stimulation) were calculated for the test compound.

Results

As shown in Table 2 and FIG. 1, the pEC50 and maximal activity for Compound X are −7.4 and 38%.

TABLE 2

| Compound | pEC50 | Activity (%) |
|---|---|---|
| X | −7.4 | 38 |

TABLE 3

Additional Biological Data

| Compound | [3H] MK-801 binding assay: EC50 (M) | Unified Activity Data: LTP Augmentation (Percent) | Unified Activity Data: LTP Concentration (uM) | Unified Activity Data: LTP, Significant (S) or Non-significant (NS) | Unified Activity Data: Porsolt Floating Time Inhibition (Percent) | Unified Activity Data: Porsolt Dose (mg/kg) | Unified Activity Data: Porsolt Dose, route | Unified Activity Data: Porsolt Time Post Dose (Hours) |
|---|---|---|---|---|---|---|---|---|
| 25-FNL-3 | 5.43E−08 | 130 | 1 | S | 80 | 3 | IV | 1 |
| 25-FNL-21 | | 80 | 0.1 | NS | | | | |
| 25-FNL-7 | 1.1E−08 | | | | | | | |
| 25-FNL-27 | 3.49E−12 | | | | | | | |
| 25-FNL-34 | | 100 | 0.1 | S | 73 | 1 | PO | 1 |

Example 4

Long Term Potentiation in Hippocampal Slices

Methods

Assays were conducted as described in Zhang et al. (Zhang, X. L., Sullivan, J. A., Moskal, J. R., Stanton, P. K., 2008. A NMDA receptor glycine site partial agonist, GLYX-13, simultaneously enhances LTP and reduces LTD at Schaffer collateral-CA1 synapses in hippocampus. Neuropharmacology. 55, 1238-50) Sprague-Dawley rats (12-18 days old; Taconic Farms) were deeply anesthetized with isoflurane and decapitated. Rat brains were removed rapidly, submerged in ice-cold artificial cerebrospinal fluid (ACSF, 2-4° C.), which contained (in mM): 124 NaCl, 4 KCl, 2 MgSO4, 2 CaCl2, 1.25 NaH2PO4, 26 NaHCO3, 10 glucose; at pH 7.4, gassed continuously with 95% O2/5% CO2). The rat brains were hemisected, the frontal lobes cut off, and individual hemispheres glued using cyanoacrylate adhesive onto a stage immersed in ice-cold ACSF gassed continuously with 95% O2/5% CO2 during slicing. Coronal slices (400 μm thick) were cut using a Vibratome (Leica VT1200S), and transferred to an interface holding chamber for incubation at room temperature for a minimum of one hour before transferring to a Haas-style interface recording chamber continuously perfused at 3 ml/min with oxygenated ACSF at 32±0.5° C. Low resistance recording electrodes were made from thin-walled borosilicate glass (1-2 MΩ after filling with ACSF) and inserted into the apical dendritic region of the Schaffer collateral termination field in stratum radiatum of field CA1 region to record field excitatory postsynaptic potentials (fEPSPs). A bipolar stainless steel stimulating electrode (FHC Co.) was placed on Schaffer collateral-commissural fibers in CA3 stratum radiatum, and constant current stimulus intensity adjusted to evoke approximately half-maximal fEPSPs once each 30 s (50-100 pA; 100 μs duration). fEPSP slope was measured before and after induction of LTP by linear interpolation from 20 to 80% of maximum negative deflection, and slopes confirmed to be stable to within ±10% for at least 15 min before commencing an experiment. Bath application of the test compound (1 μM) was applied 30 min prior to application of Schaffer collateral stimulus trains to elicit LTP. LTP was induced by stimulation of Schaffer collateral axons with four high frequency theta burst stimulus trains of 10×100 Hz/5 pulse bursts each, applied at an inter-burst interval of 200 ms. Each train was 2 seconds in duration, and trains were applied 15 seconds apart. The signals were recorded using a Multiclamp 700B amplifier and digitized with a Digidata 1322 (Axon Instruments, USA), Data were analyzed using pClamp software (version 9, Axon Instruments) on an IBM-compatible personal computer.

Results

Figure 2:
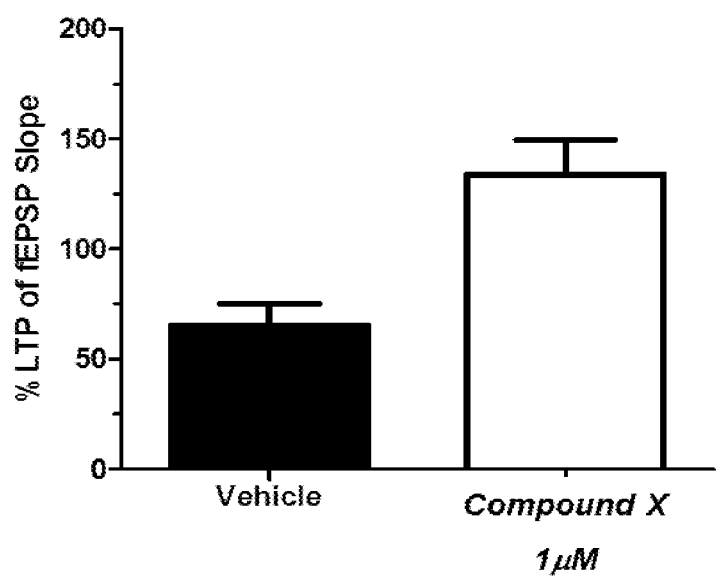
FIG. 2 shows results of long term potentiation in hippocampal slices using Compound X.

As shown in FIG. 2, Compound X tested at 1 μM increased long-term potentiation after high frequency stimulation of rat Schaffer collateral-evoked NMDA e.p.s.c.s recorded in CA1 pyramidal neurons.

TABLE 4

Additional Biological Data

| Compound | MK-801 Glycine Site Binding Assay: Rat Cortex EC50 (M) | LTP: LTP Augmentation (%) | LTP: LTP Concentration (μM) | LTP: LTP Significance, S or NS |
|---|---|---|---|---|
| 25-FNL-38 | 3.313E−09 | | | |
| 25-FNL-2 | 2.002E−08 | | | |
| 25-FNL-10 | 1.038E−12 | 90 | 1 | NS |
| 25-FNL-14 | 6.133E−11 | 120 | 1 | NS |
| 25-FNL-33 | 1.89E−08 | 140 | 1 | S |

EQUIVALENTS

Those skilled in the art will recognize, or be able to ascertain using no more than routine experimentation, many equivalents to the specific embodiments of the invention described herein. Such equivalents are intended to be encompassed by the following claims.

INCORPORATION BY REFERENCE

The entire contents of all patents, published patent applications, websites, and other references cited herein are hereby expressly incorporated herein in their entireties by reference.

What is claimed is:

1. A compound represented by:

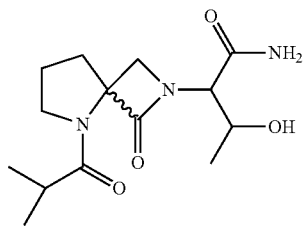 [SMILES: CC(C)C(=O)N1CCCC12CN(C(C(N)=O)C(C)O)C2=O]

and stereoisomers and pharmaceutically acceptable salts thereof.

2. A pharmaceutical composition comprising the compound of claim 1, and a pharmaceutically acceptable excipient.

3. The pharmaceutical composition of claim 2, suitable for oral administration.

4. The pharmaceutical composition of claim 2, suitable for intravenous administration.

5. A method of treating a migraine in a patient in need thereof, comprising administering to said patient a pharmaceutically effective amount of a compound of claim 1.

6. A method of treating neuropathic pain in a patient in need thereof, comprising administering to said patient a pharmaceutically effective amount of a compound of claim 1.

7. A method of treating traumatic brain injury in a patient in need thereof, comprising administering to said patient a pharmaceutically effective amount of a compound of claim 1.

8. A compound selected from:

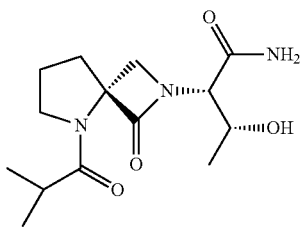 [SMILES: CC(C)C(=O)N1CCC[C@]12CN([C@H](C(N)=O)[C@@H](C)O)C2=O]

and

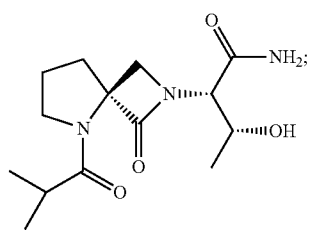 [SMILES: CC(C)C(=O)N1CCC[C@@]12CN([C@H](C(N)=O)[C@@H](C)O)C2=O]

and
pharmaceutically acceptable salts thereof.

* * * * *